US009722182B2

(12) United States Patent
Lee et al.

(10) Patent No.: US 9,722,182 B2
(45) Date of Patent: *Aug. 1, 2017

(54) HETEROCYCLIC COMPOUND AND ORGANIC LIGHT-EMITTING DEVICE INCLUDING THE SAME

(71) Applicant: SAMSUNG DISPLAY CO., LTD., Yongin (KR)

(72) Inventors: Sun-Young Lee, Yongin (KR); Yoon-Hyun Kwak, Yongin (KR); Bum-Woo Park, Yongin (KR); Jong-Won Choi, Yongin (KR); Wha-Il Choi, Yongin (KR); So-Yeon Kim, Yongin (KR); Ji-Youn Lee, Yongin (KR)

(73) Assignee: SAMSUNG DISPLAY CO., LTD., Yongin, Gyeonggi-Do (KR)

(*) Notice: Subject to any disclaimer, the term of this patent is extended or adjusted under 35 U.S.C. 154(b) by 951 days.

This patent is subject to a terminal disclaimer.

(21) Appl. No.: 13/939,342

(22) Filed: Jul. 11, 2013

(65) Prior Publication Data
US 2014/0117326 A1    May 1, 2014

(30) Foreign Application Priority Data

Oct. 30, 2012  (KR) .................. 10-2012-0121523

(51) Int. Cl.
H01L 51/50    (2006.01)
H01L 51/00    (2006.01)
(Continued)

(52) U.S. Cl.
CPC ........ *H01L 51/0052* (2013.01); *C07D 209/80* (2013.01); *C07D 403/14* (2013.01);
(Continued)

(58) Field of Classification Search
CPC .... C09K 11/06; C07D 209/80; C07D 403/14; C07D 405/04; C07D 491/048;
(Continued)

(56) References Cited

U.S. PATENT DOCUMENTS 3,620,748 A * 11/1971 Fichter, Jr. ............ G03F 7/0295
                                                    430/270.1
4,092,161 A *  5/1978 Radler, Jr. ............ G03G 5/047
                                                    430/57.3
(Continued)

FOREIGN PATENT DOCUMENTS

JP       8-12600      1/1996
JP    2000-003782     1/2000
(Continued)

OTHER PUBLICATIONS

Machine translation for KP 1020120116879 (publication date Oct. 2012).*

(Continued)

*Primary Examiner* — Dawn Garrett
(74) *Attorney, Agent, or Firm* — Lee & Morse, P.C.

(57) ABSTRACT

A heterocyclic compound represented by Formula 1 below, and an organic light-emitting device including the heterocyclic compound:

(Continued)

US 9,722,182 B2

Page 2

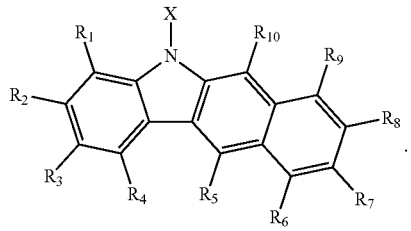

<Formula 1>

20 Claims, 1 Drawing Sheet

(51) Int. Cl.
C09K 11/06 (2006.01)
C07D 403/14 (2006.01)
C07D 405/04 (2006.01)
C07D 491/048 (2006.01)
C07D 209/80 (2006.01)

(52) U.S. Cl.
CPC ....... C07D 405/04 (2013.01); C07D 491/048 (2013.01); C09K 11/06 (2013.01); H01L 51/0059 (2013.01); H01L 51/0061 (2013.01); H01L 51/0065 (2013.01); H01L 51/0071 (2013.01); H01L 51/0072 (2013.01); H01L 51/0073 (2013.01); H01L 51/0074 (2013.01); H01L 51/006 (2013.01); H01L 51/0055 (2013.01); H01L 51/0081 (2013.01); H01L 51/0085 (2013.01); H01L 51/0087 (2013.01); H01L 51/0088 (2013.01); H01L 51/5016 (2013.01); H01L 51/5056 (2013.01)

(58) Field of Classification Search
CPC ............. H01L 51/0052; H01L 51/0055; H01L 51/0059; H01L 51/006; H01L 51/0061; H01L 51/0065; H01L 51/0071; H01L 51/0072; H01L 51/0073; H01L 51/0074; H01L 51/0081
See application file for complete search history.

(56) References Cited

U.S. PATENT DOCUMENTS

| | | | |
|---|---|---|---|
| 5,635,308 A | 6/1997 | Inoue et al. | |
| 5,645,948 A | 7/1997 | Shi et al. | |
| 5,972,247 A | 10/1999 | Shi et al. | |
| 6,465,115 B2 | 10/2002 | Shi et al. | |
| 6,596,415 B2 | 7/2003 | Shi et al. | |
| 8,999,528 B2* | 4/2015 | Kim | H01L 51/0072 257/40 |
| 9,006,721 B2* | 4/2015 | Lee | H01L 51/0061 257/40 |
| 9,118,021 B2* | 8/2015 | Lee | H05B 33/14 |
| 9,255,084 B2* | 2/2016 | Lee | C07D 403/10 |
| 9,425,410 B2* | 8/2016 | Kim | H01L 51/0072 |
| 2005/0221124 A1 | 10/2005 | Hwang et al. | |
| 2011/0031484 A1* | 2/2011 | Lee | C07D 209/90 257/40 |
| 2011/0210318 A1 | 9/2011 | Bae et al. | |
| 2013/0048955 A1* | 2/2013 | Lee | C07D 403/10 257/40 |
| 2013/0270524 A1* | 10/2013 | Park | C07D 403/12 257/40 |
| 2014/0209880 A1* | 7/2014 | Choi | H01L 51/0067 257/40 |
| 2014/0225072 A1* | 8/2014 | Kim | H01L 51/0072 257/40 |
| 2014/0225079 A1* | 8/2014 | Lee | H01L 51/0072 257/40 |
| 2014/0319494 A1* | 10/2014 | Miyashita | H01L 51/0058 257/40 |

FOREIGN PATENT DOCUMENTS

| | | | |
|---|---|---|---|
| KR | 10-0573137 | | 4/2006 |
| KR | 10-2010-0023783 | | 3/2010 |
| KR | 10-2010-0108924 | | 10/2010 |
| KR | 10-2011-0217784 | | 11/2011 |
| WO | WO 2010/114264 A2 | | 10/2010 |
| WO | WO-2011/145876 A2 | | 11/2011 |
| WO | KR 10-2012-0081539 | * | 7/2012 |
| WO | KR 10-2012-0104067 | * | 9/2012 |
| WO | KR 10-2012-0116879 | * | 10/2012 |
| WO | KR 10-2012-0116881 | * | 10/2012 |
| WO | WO 2012141109 | * | 10/2012 |
| WO | KR 10-2012-0122897 | * | 11/2012 |

OTHER PUBLICATIONS

Machine translation for KR 1020120081539 (publication date Jul. 2012).*
Machine translation for KR 1020120104067 (publication date Sep. 2012).*
Machine translation for KR 10-2012-0116881 (publication date Oct. 2012).*
Shi et al., Chem. Eur. J., 2012, vol. 18, pp. 8092-8099.*
Yamaguchi et al. "Diphenylamino-Substituted 2,5-Diarylsiloles for Single-Layer Organic Electroluminescent Devices", Chemical Society of Japan, Chemistry Letters, 2001, pp. 98-99.
Adachi et al. "Confinement of Charge Carriers and Molecular Excitons Within 5-nm-thick Emitter Layer in Organic Electroluminescent Devices with a Double Heterostructure", Appl. Phys. Lett 57(6), Aug. 6, 1990, pp. 531-533.
Sakamoto et al. "Synthesis, Characterization, and Electron-Transport Property of Perfluorinated Phenylene Dendrimers", American Chemical Society, J. Am Chem. Soc., 2000 pp. 1832-1833.
Tang et al. "Organic Electroluminescent Diodes", Appl. Phys. Lett, 51 (12), Sep. 21, 1987, pp. 913-915.

* cited by examiner

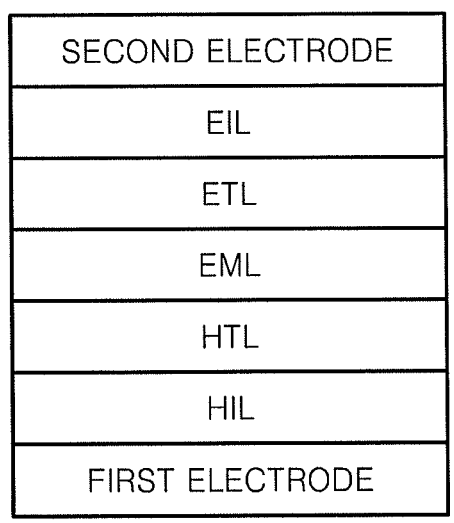

HETEROCYCLIC COMPOUND AND ORGANIC LIGHT-EMITTING DEVICE INCLUDING THE SAME

CROSS-REFERENCE TO RELATED PATENT APPLICATION

This application claims priority under 35 U.S.C. §119 to Korean Patent Application No. 10-2012-0121523 filed on Oct. 30, 2012, in the Korean Intellectual Property Office, and entitled: "HETEROCYCLIC COMPOUND AND ORGANIC LIGHT-EMITTING DEVICE INCLUDING THE SAME," the disclosure of which is incorporated herein in its entirety by reference.

BACKGROUND

1. Field

The embodiments relate to a heterocyclic compound and an organic light-emitting device including the heterocyclic compound.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A OLED may have a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An exemplary operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

Embodiments are directed to a heterocyclic compound represented by Formula 1 below:

<Formula 1>

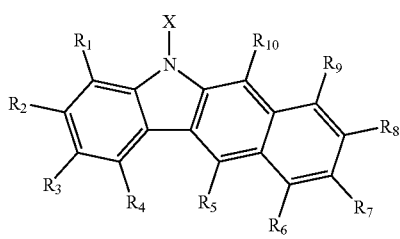

In Formula 1, $R_1$ to $R_{10}$ each independently may be a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group, $R_8$ and $R_9$ may be linked to each other to form a first ring or $R_6$ and $R_7$ may be linked to each other to form a second ring, and X may be a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

The heterocyclic compound may be represented by Formula 2 below:

<Formula 2>

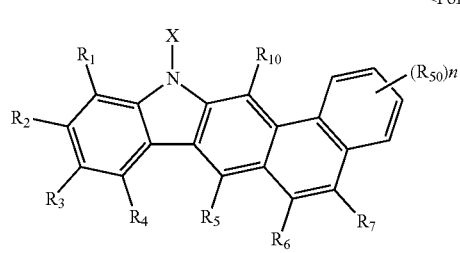

In Formula 2, $R_1$ to $R_7$, $R_{10}$, and $R_{50}$ each independently may be a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group, n may be an integer from 1 to 4, when n>1, a plurality of $(R_{50})_n$ moieties may be optionally linked to each other to form a ring, and X may be a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

$R_7$ in Formula 2 may be a group represented by one of Formulae 2a to 2d below:

2a

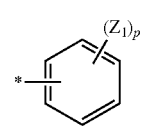

2b

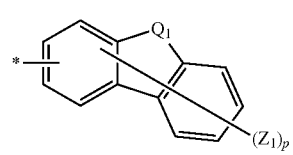

2c

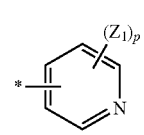

2d

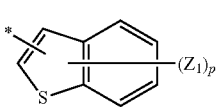

In Formulae 2a to 2d, $Q_1$ may be a linker represented by —$C(R_{30})(R_{31})$—, —O—, —S—, or —$N(R_{32})$—, $Z_1$, $R_{30}$, $R_{31}$, and $R_{32}$ each independently may be a hydrogen atom, a deuterium atom, a substituted or unsubstituted C1-C20 alkyl group, a substituted or unsubstituted C6-C20 aryl group, a substituted or unsubstituted C3-C20 heteroaryl group, an amino group substituted with a C6-C20 aryl group, a substituted or unsubstituted C6-C20 condensed polycyclic group, a halogen group, a cyano group, a nitro group, a hydroxy group, or a carboxy group, p may be an integer from 1 to 7, and * may indicate a binding site of $R_7$ in Formula 2.

X in Formula 2 may be a group represented by one of Formulae 3a to 3c below:

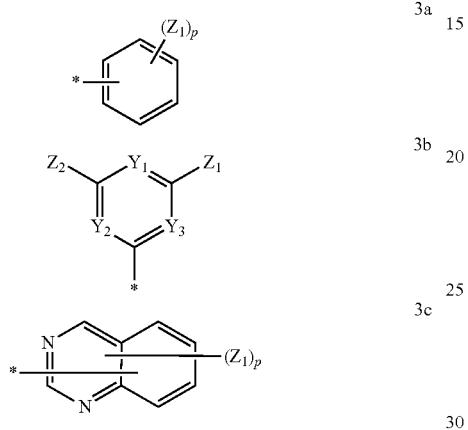

In Formulae 3a to 3c, $Z_1$ and $Z_2$ each independently may be a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group, a cyano group, a nitro group, a hydroxyl group, or a carboxy group, $Y_1$ to $Y_3$ may be each independently C or N, p may be an integer from 1 to 5, and * may indicate a binding site of X in Formula 2.

The heterocyclic compound may be represented by Formula 3 below:

<Formula 3>

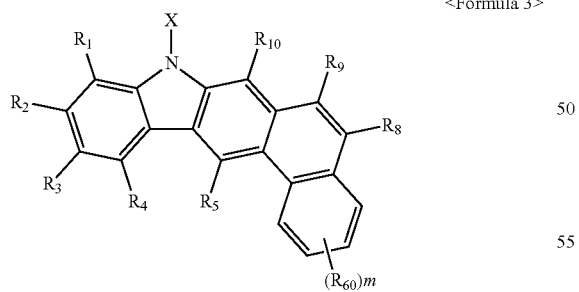

In Formula 3, $R_1$ to $R_5$, $R_9$ to $R_{10}$, and $R_{60}$ each independently may be a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group, m may be an integer from 1 to 4, when m>1, a plurality of $(R_{60})_m$ moieties may be optionally linked together to form a ring, and X may be a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

$R_8$ in Formula 3 may be a group represented by one of Formulae 2a to 2d below:

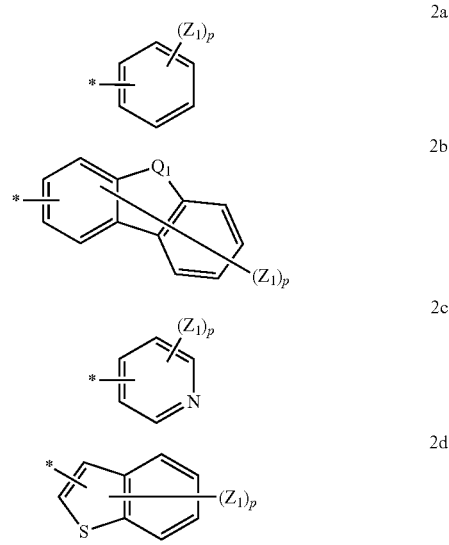

In Formulae 2a to 2d, $Q_1$ may be a linker represented by $-C(R_{30})(R_{31})-$, $-O-$, $-S-$, or $-N(R_{32})-$, $Z_1$, $R_{30}$, $R_{31}$, and $R_{32}$ each independently may be a hydrogen atom, a deuterium atom, a substituted or unsubstituted C1-C20 alkyl group, a substituted or unsubstituted C6-C20 aryl group, a substituted or unsubstituted C3-C20 heteroaryl group, an amino group substituted with a C6-C20 aryl group, a substituted or unsubstituted C6-C20 condensed polycyclic group, a halogen group, a cyano group, a nitro group, a hydroxy group, or a carboxy group, p may be an integer from 1 to 7, and * may indicate a binding site of $R_8$ in Formula 3.

X in Formula 3 may be a group represented by one of Formulae 3a to 3c:

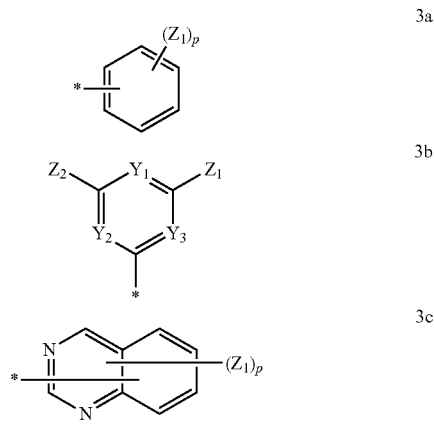

In Formulae 3a to 3c, $Z_1$ and $Z_2$ each independently may be a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group, a cyano group, a nitro group, a hydroxyl group, or a carboxy group, $Y_1$ to $Y_3$ each independently may be C or N, p may be an integer from 1 to 5, and * may indicate a binding site of X in Formula 3.

The compound of Formula 1 may be one of the compounds below:

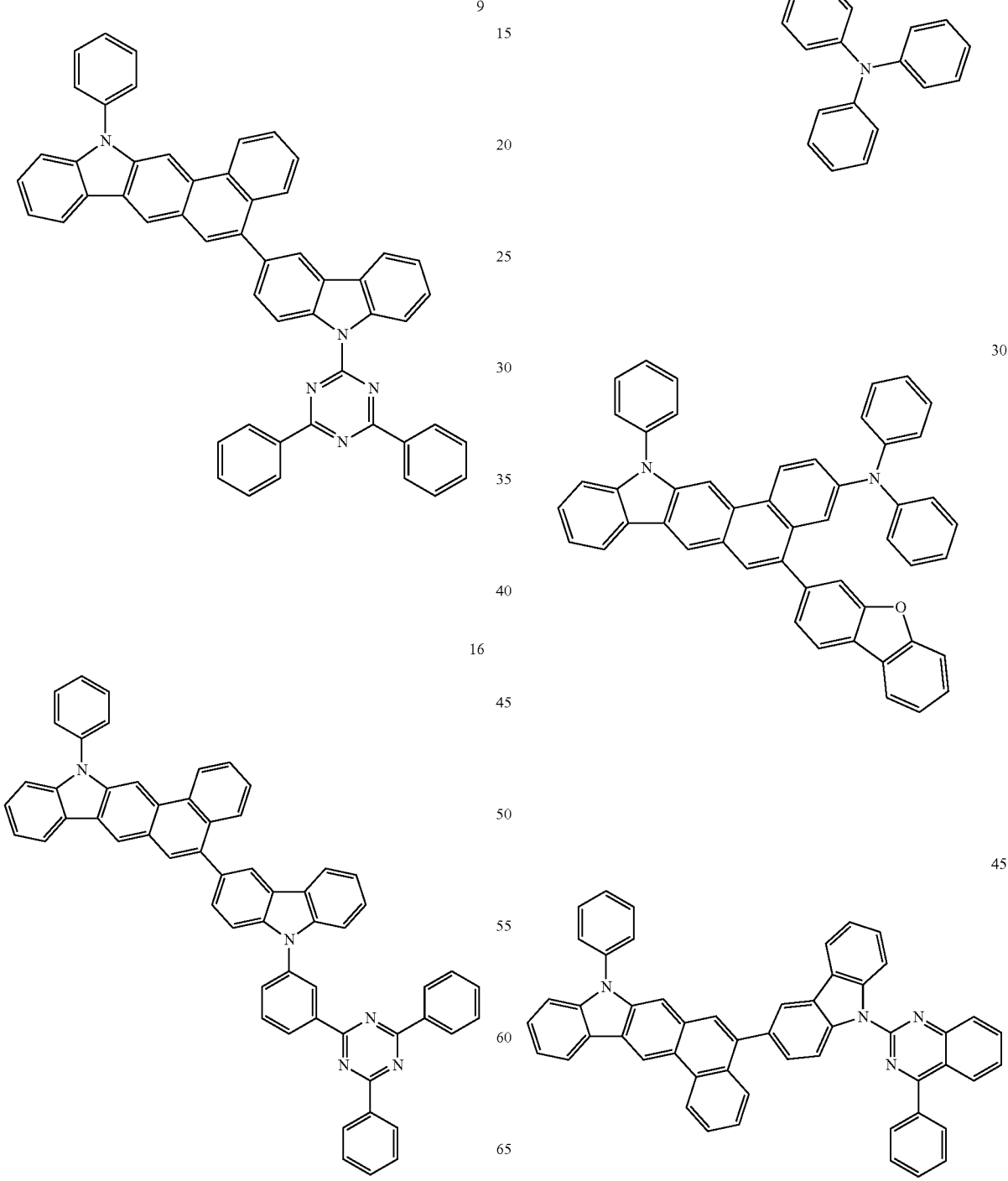
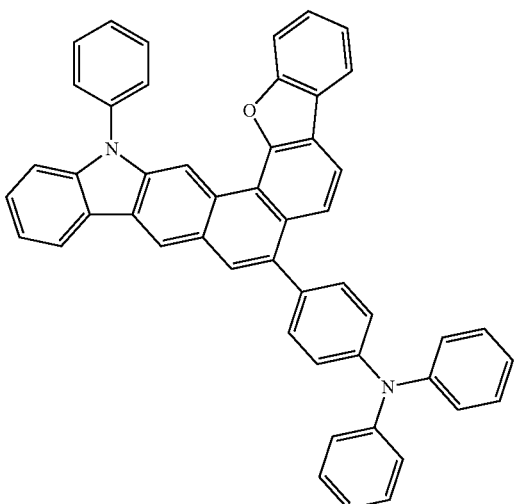

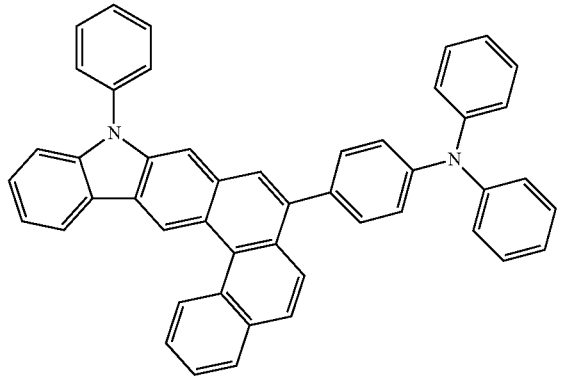

Embodiments are also directed to an organic light-emitting device, including a first electrode, a second electrode, and an organic layer between the first electrode and the second electrode, wherein the organic layer may include the heterocyclic compound.

The organic layer may include an emission layer, and the heterocyclic compound may be included as a host or a dopant for a fluorescent or phosphorescent device.

The organic layer may be a hole injection layer, a hole transport layer, or a functional layer having both hole injection and hole transport capabilities.

The organic light-emitting device may include an emission layer, an electron injection layer, an electron transport layer, or a functional layer having both electron injection and transport capabilities, and a hole injection layer, a hole transport layer, or a functional layer having both hole injection and transport capabilities, at least one of the hole injection layer, the hole transport layer, and the functional layer having both hole injection and hole transport capabilities may include the heterocyclic compound, and the emission layer may include an anthracene-based compound, an arylamine-based compound, or a styryl-based compound.

The organic light-emitting device may include an emission layer, an electron injection layer, an electron transport layer, or a functional layer having both electron injection and transport capabilities, and a hole injection layer, a hole transport layer, or a functional layer having both hole injection and transport capabilities, at least one of the hole injection layer, the hole transport layer, and the functional layer having both hole injection and hole transport capabilities may include the heterocyclic compound; and the emission layer may include at least one of a red, green, blue, or white emission layer, one of which may include a phosphorescent compound.

The at least one of the hole injection layer, the hole transport layer, and the functional layer having both hole injection and hole transport capabilities may further include a charge-generating material.

The charge-generating material may be a p-dopant.

The p-dopant may be a quinine derivative, a metal oxide, or a cyano group-containing compound.

The organic layer may include an electron transport layer, and the electron transport layer includes a metal complex.

The metal complex may be a Li complex.

The organic layer may be formed from the heterocyclic compound using a wet process.

Embodiments are also directed to a flat panel display device comprising the organic light-emitting, wherein the first electrode of the organic light-emitting device may be electrically connected to a source electrode or a drain electrode of a thin-film transistor.

BRIEF DESCRIPTION OF THE DRAWING

Features will become apparent to those of skill in the art by describing in detail exemplary embodiments with reference to the attached drawing in which FIG. 1 illustrates a schematic view of a structure of an organic light-emitting device according to an embodiment.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an embodiment, there is provided a heterocyclic compound represented by Formula 1 below:

<Formula 1>

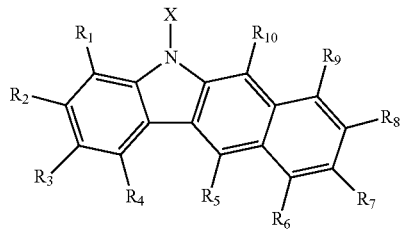

In Formula 1, $R_1$ to $R_{10}$ are each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group;

$R_8$ and $R_9$ are linked to each other to form a ring, or $R_6$ and $R_7$ are linked to each other to form a ring; and X is a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

The heterocyclic compound of Formula 1 above may be used as a hole injection/hole transport material for organic light-emitting devices or a host material for an emission layer of organic light-emitting devices. The heterocyclic compound of Formula 1 above has high thermal stability. Lowest unoccupied molecular orbital (LUMO) energy level and a highest occupied molecular orbital (HOMO) energy level of the heterocyclic compound may be suitable for an emission layer for organic light-emitting devices. Due to a large highest occupied molecular orbital (HOMO)-lowest unoccupied molecular orbital (LUMO) energy gap of the heterocyclic compound of Formula 1, the energy level of the heterocyclic compound may be easily controlled by varying substituents of the heterocyclic compound. Accordingly, the heterocyclic compound of Formula 1 may be effectively used as a phosphorescent host.

Substituents in the heterocyclic compound of Formula 1 will now be described in detail.

In some embodiments, Formula 1 may be represented by Formula 2 below:

<Formula 2>

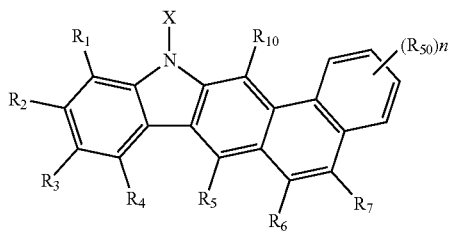

In Formula 2, $R_1$ to $R_7$, $R_{10}$, and $R_{50}$ may be each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group;

n may be an integer from 1 to 4;

a plurality of $R_{50}$s may be optionally linked together to form a ring; and

X may be a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

In some embodiments, $R_7$ in Formula 2 may be a group represented by one of Formulae 2a to 2d below:

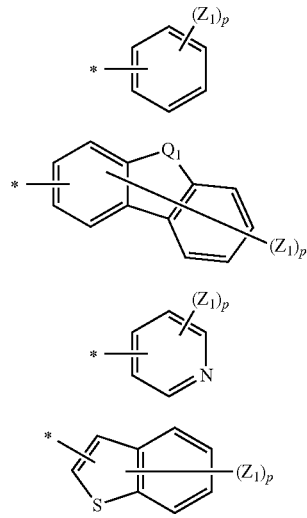

In Formulae 2a to 2d, $Q_1$ may be a linker represented by —C($R_{30}$)($R_{31}$)—, —O—, —S—, or —N($R_{32}$)—;

$Z_1$, $R_{30}$, $R_{31}$, and $R_{32}$ may be each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, an amino group substituted with a C6-C20 aryl group, a substituted or unsubstituted C6-C20 condensed polycyclic group, a halogen group (e.g., a halogen), a cyano group, a nitro group, a hydroxy group, or a carboxy group;

p may be an integer from 1 to 7; and

* indicates a binding site.

Additionally, in Formulae 2b and 2d above, the line corresponding to $(Z_1)_p$ that extends across multiple rings indicates that the $(Z_1)_p$ moiety may be a substituent at one or more location of one or more of the rings that the line crosses. This interpretation of a line crossing multiple rings also applies to the other formulas in this disclosure.

In some embodiments, X in Formula 2 may be a group represented by one of Formulae 3a to 3c:

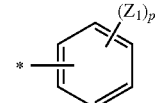

3a

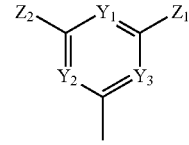

3b

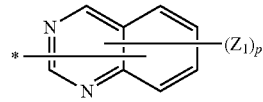

3c

In Formulae 3a to 3c, $Z_1$ and $Z_2$ may be each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group (e.g., a halogen), a cyano group, a nitro group, a hydroxyl group, or a carboxy group; and $Y_1$ to $Y_3$ may be each independently C or N;

p may be an integer from 1 to 5; and

* may indicate a binding site.

In some embodiments, Formula 1 may be represented by Formula 3 below:

<Formula 3>

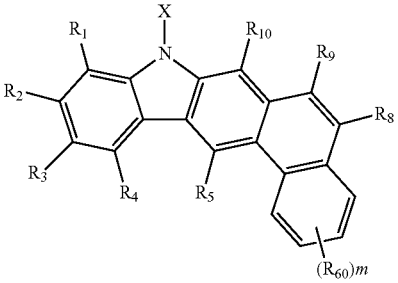

In Formula 3, $R_1$ to $R_5$, $R_8$ to $R_{10}$, and $R_{60}$ may be each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with a C6-C60 aryl group, a substituted or unsubstituted C3-C60 heteroaryl group, or a substituted or unsubstituted C6-C60 condensed polycyclic group;

m may be an integer from 1 to 4;

a plurality of $R_{60}$s may be optionally linked together to form a ring; and

X may be a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

In some embodiments, $R_8$ in Formula 3 may be a group represented by one of Formulas 2a to 2d below:

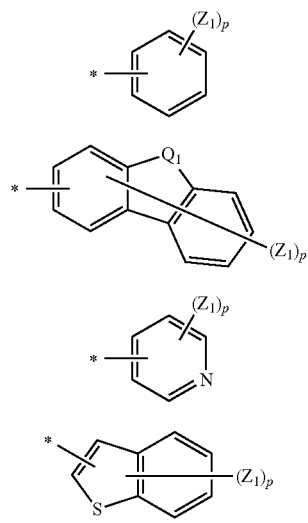

In Formulae 2a to 2d, $Q_1$ may be a linker represented by —C($R_{30}$)($R_{31}$)—, —O—, —S—, or —N($R_{32}$)—;

$Z_1$, $R_{30}$, $R_{31}$, and $R_{32}$ may be each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, an amino group substituted with a C6-C20 aryl group, a substituted or unsubstituted C6-C20 condensed polycyclic group, a halogen group (e.g., a halogen), a cyano group, a nitro group, a hydroxy group, or a carboxy group;

p may be an integer from 1 to 7; and

* may indicate a binding site.

In some embodiments, X in Formula 3 may be a group represented by one of Formulae 3a to 3c:

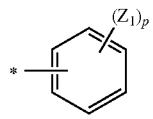

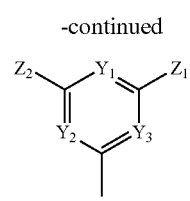

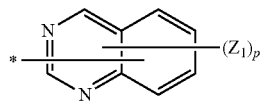

In Formulae 3a to 3c, $Z_1$ and $Z_2$ may be each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group), a cyano group, a nitro group, a hydroxyl group, or a carboxy group; and $Y_1$ to $Y_3$ may be each independently C or N;

p may be an integer from 1 to 5; and

* may indicate a binding site.

Hereinafter, substituents described with reference to the formulae above will now be described in detail. In this regard, the numbers of carbons in substituents are presented only for illustrative purposes and do not limit the characteristics of the substituents. The term "substituted" or "substitution" will be defined in conjunction with a substituent of an alkyl group (see below), and will not be repeated with respect to each of the other described groups.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The unsubstituted C2-C60 alkenyl group indicates an unsaturated alkyl groups having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the substituted or unsubstituted C6-C60 aryl group are a phenyl group, a C1-C10 alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, a o-, m-, and p-tolyl group, an o-, m-, and p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from N, O, P and S. At least two rings may be fused to each other or linked to each other by a single bond. Non-limiting examples of the unsubstituted C4-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —OA1 wherein A1 may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA1 wherein A1 may be a C6-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

The heterocyclic compound of Formula 1 may be one of the following compounds, but is not limited thereto:

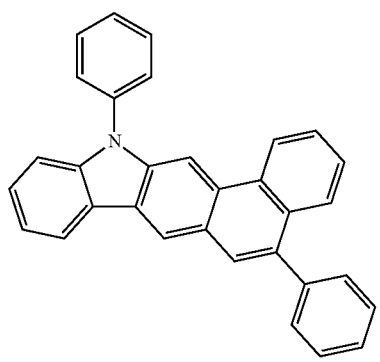

1

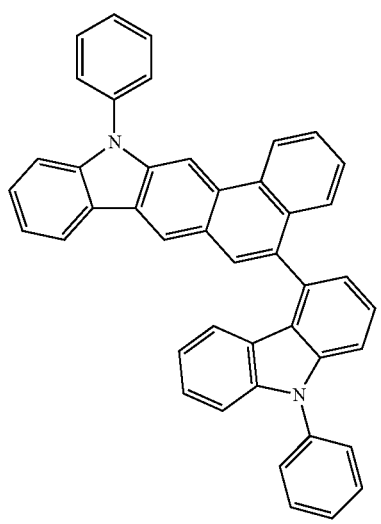

2

3
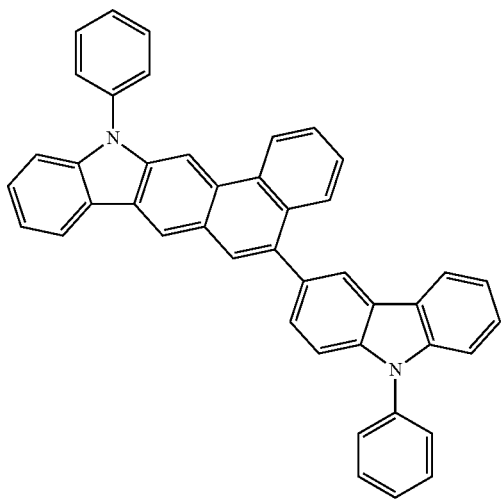
4
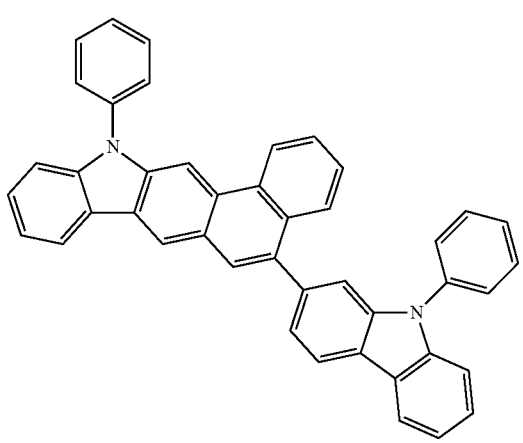
5
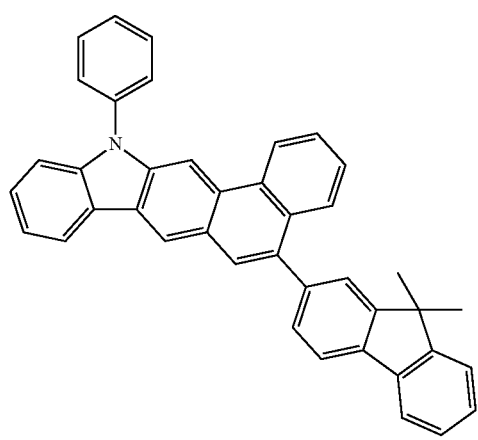
6
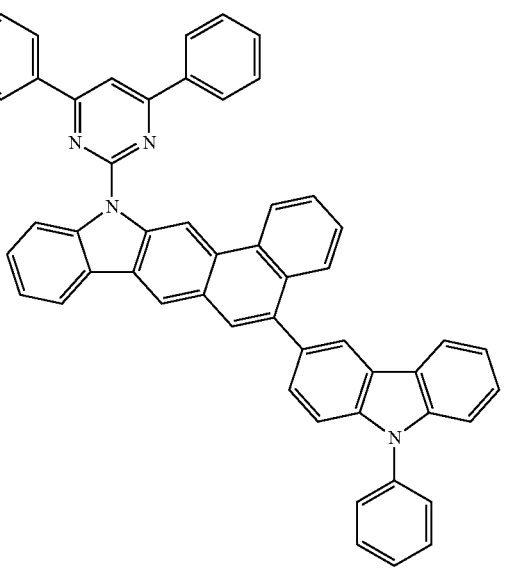
7
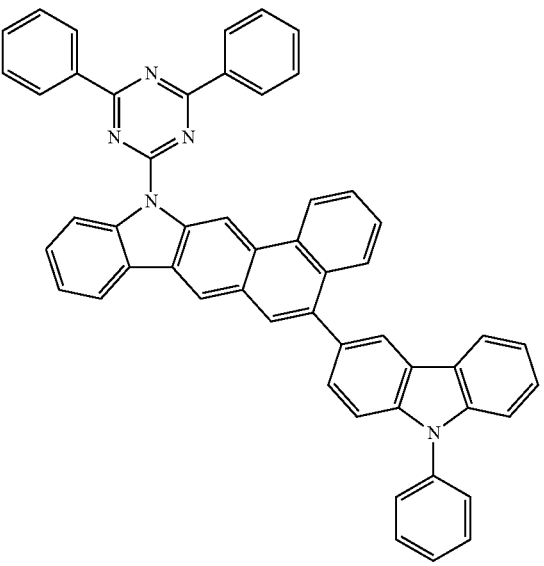

8
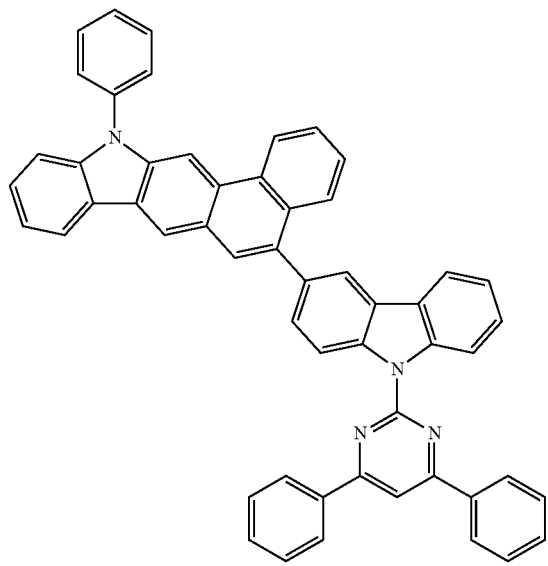
9
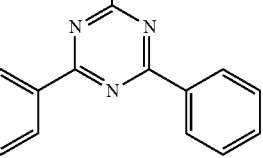
10
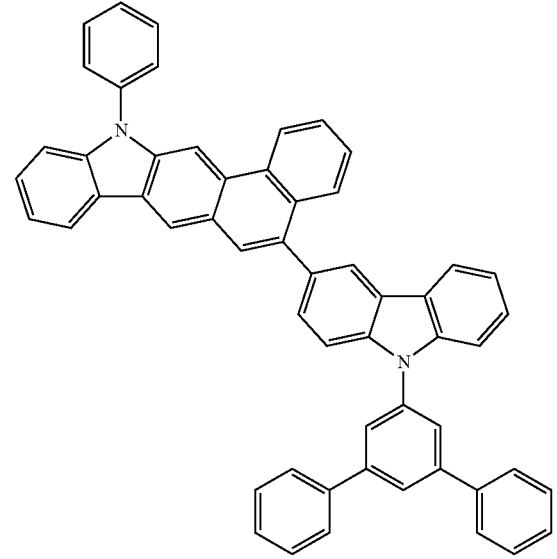
11
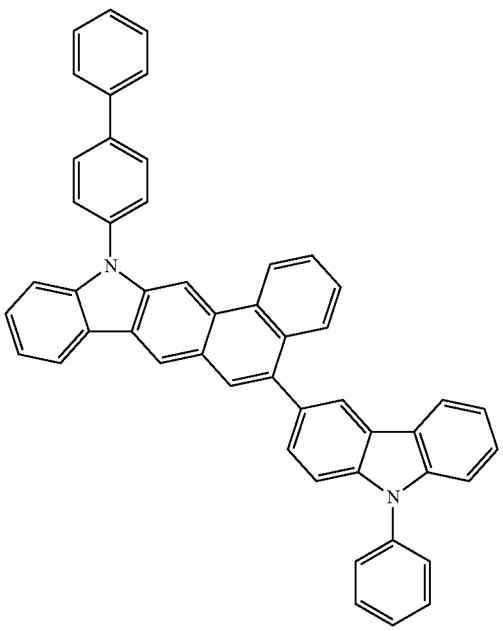

12
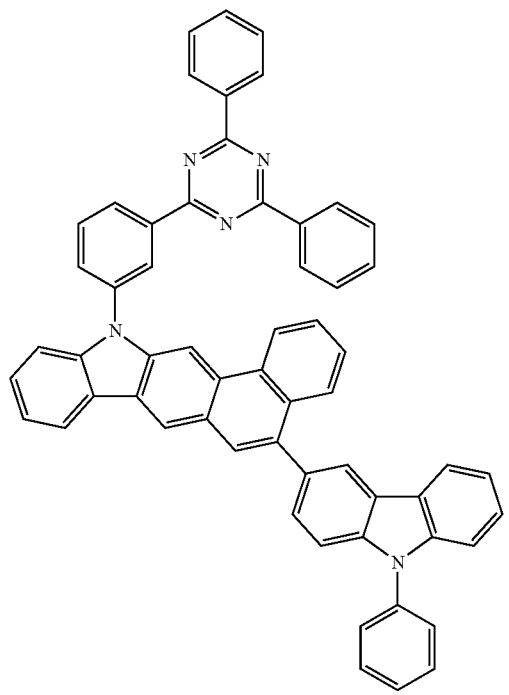
14
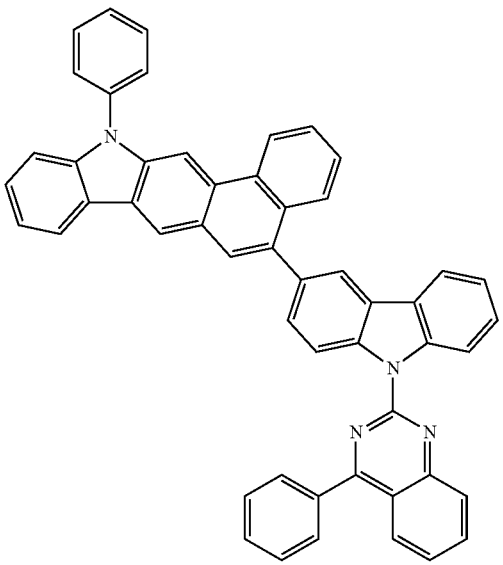
13
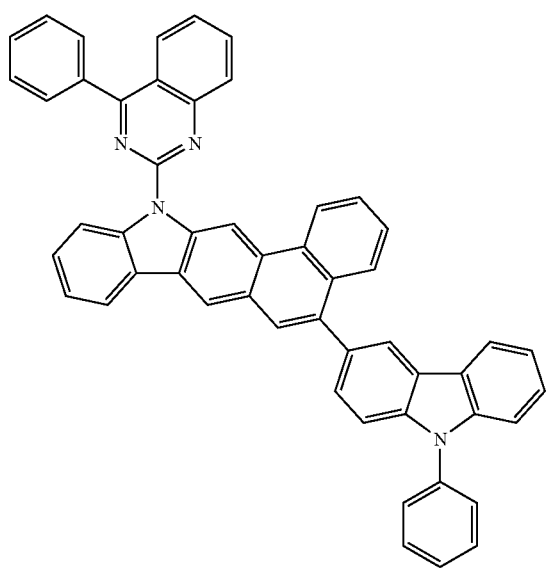
15

-continued
16
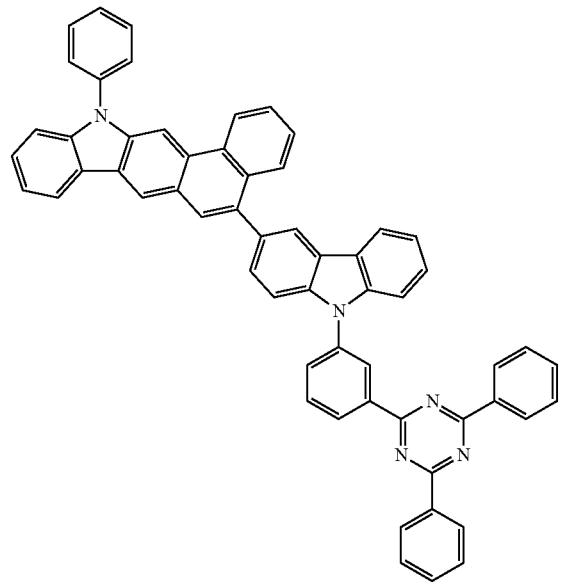
17
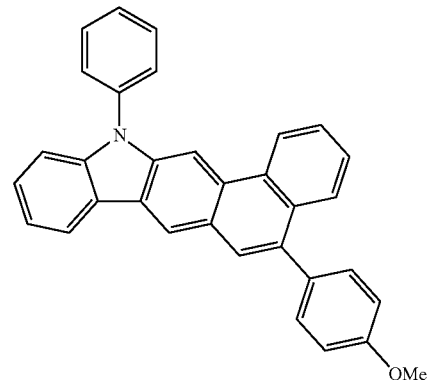
18
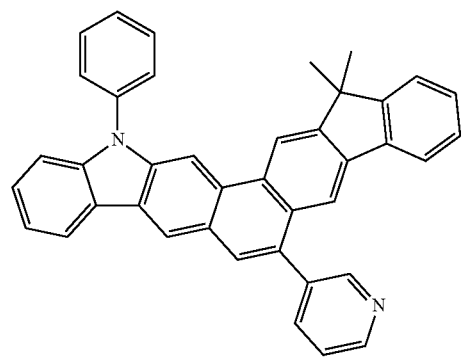
-continued
19
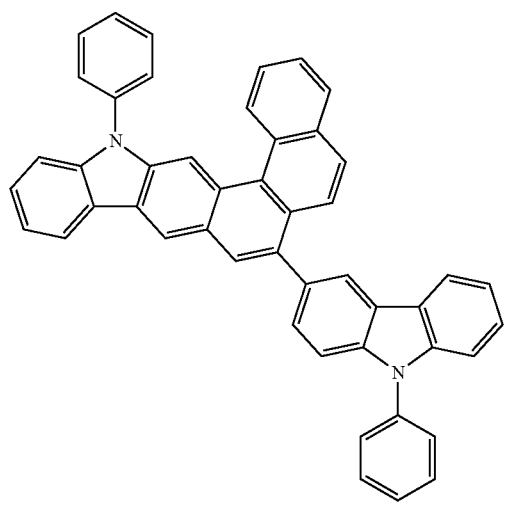
20
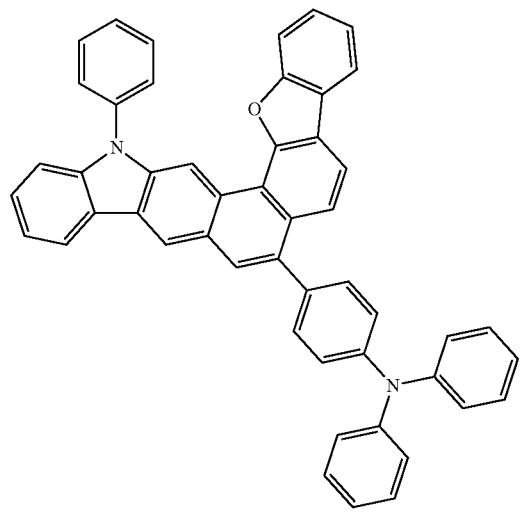
21
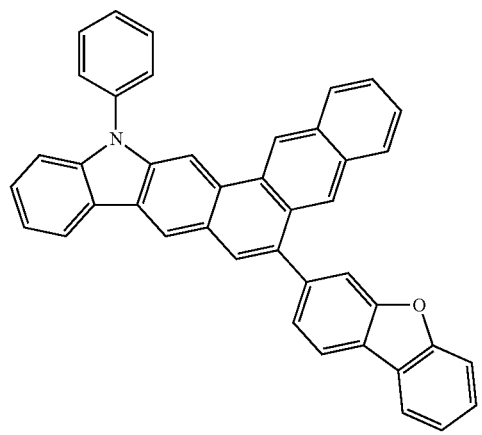

22
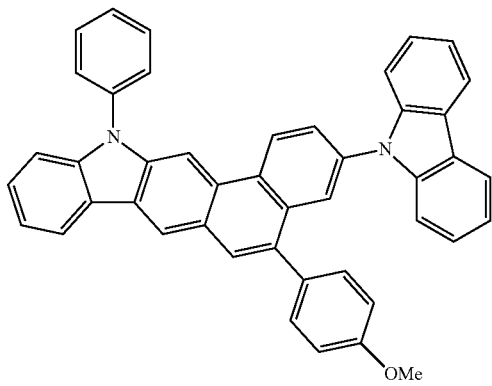
23
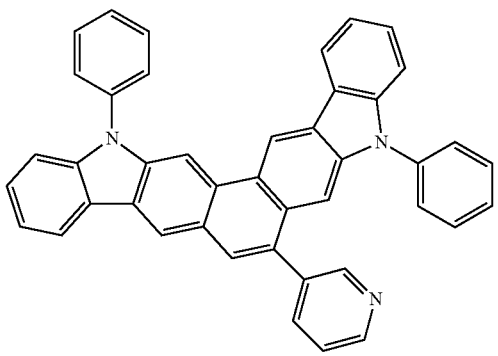
24
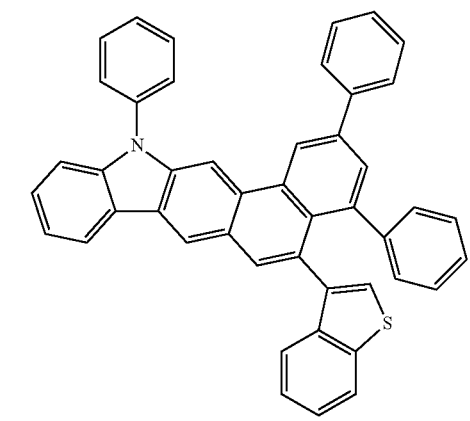
25
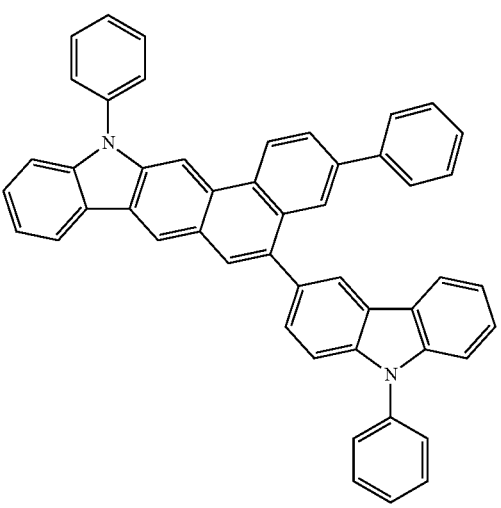
26
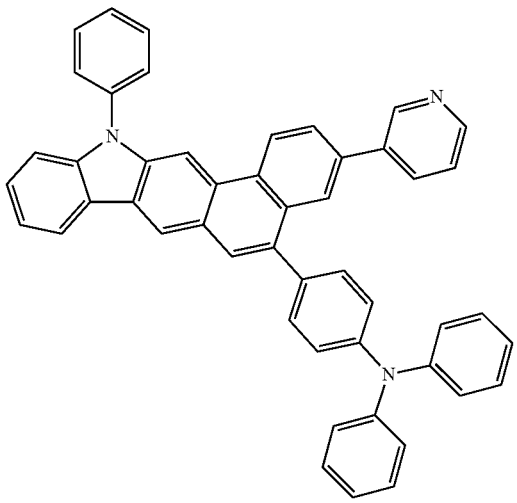
27
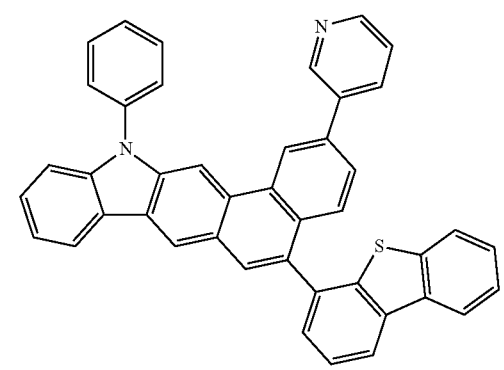
28

29
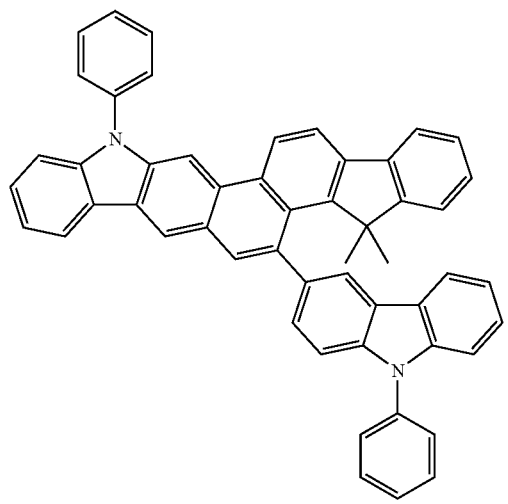
30
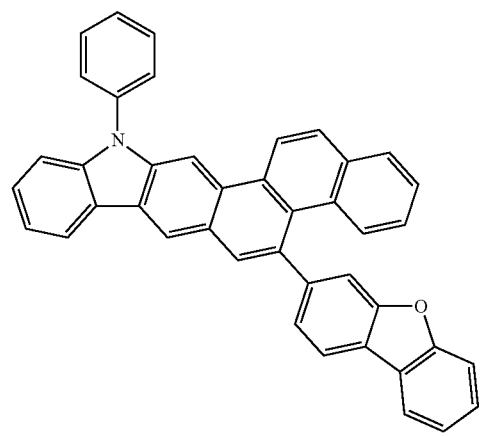
31
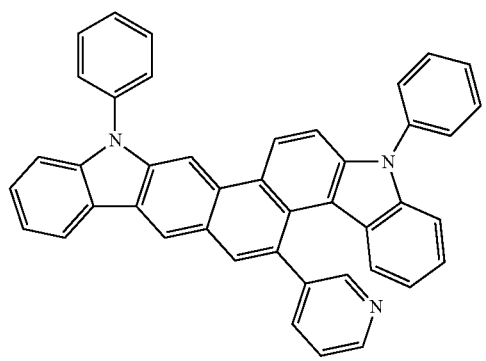
32
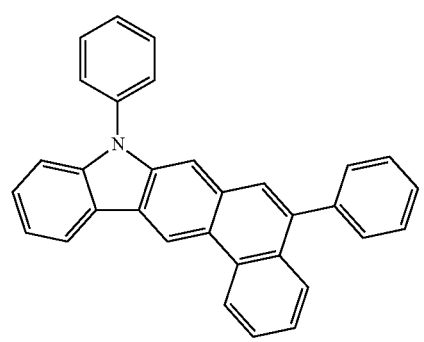
33
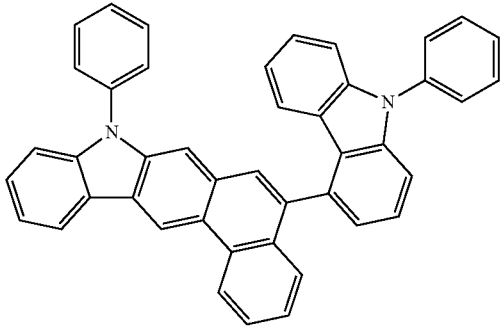
34
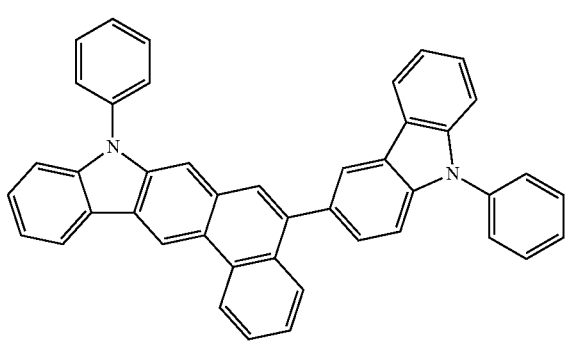
35
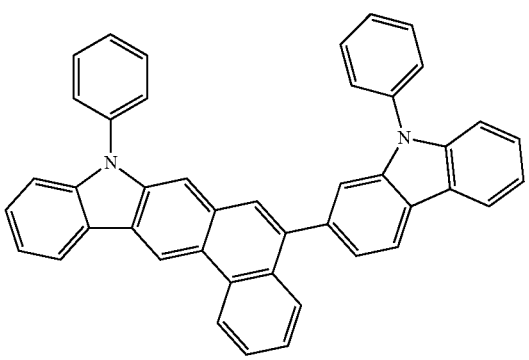
36
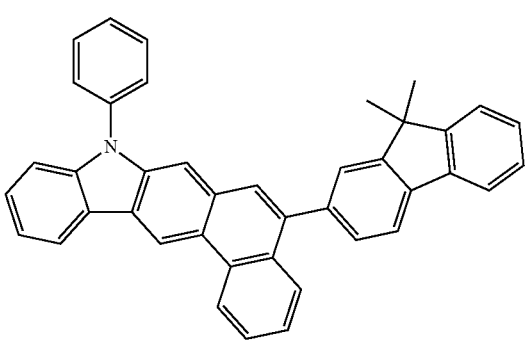

-continued
37
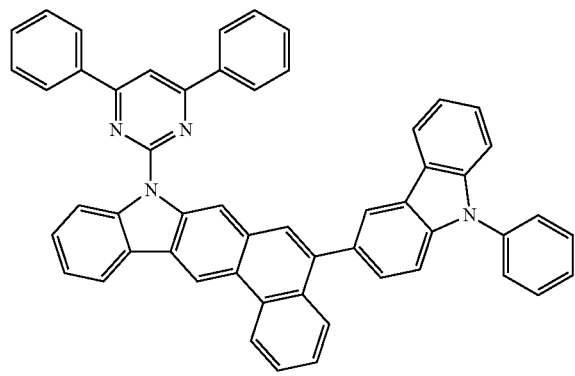
38
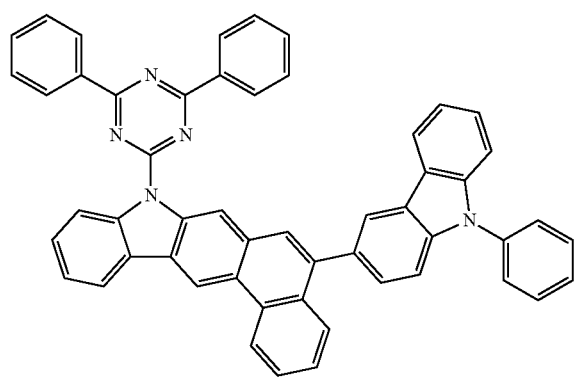
39
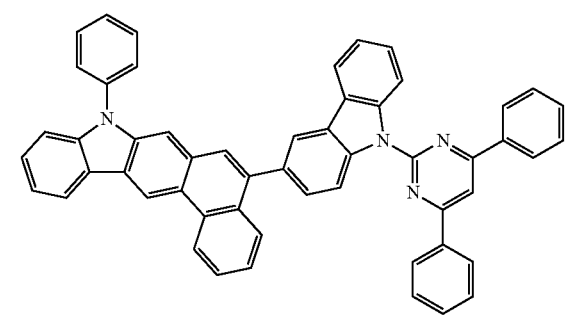
40
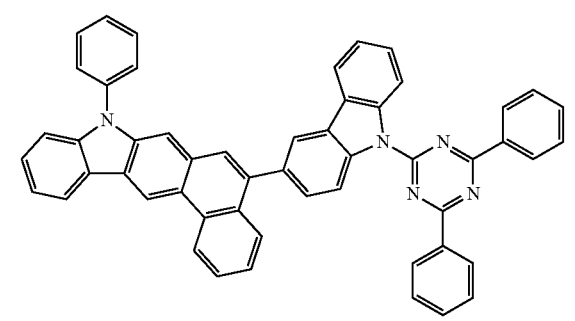
-continued
41
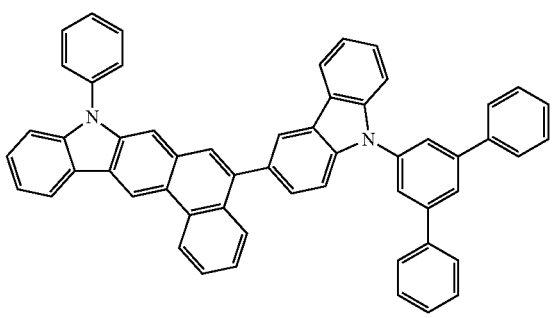
42
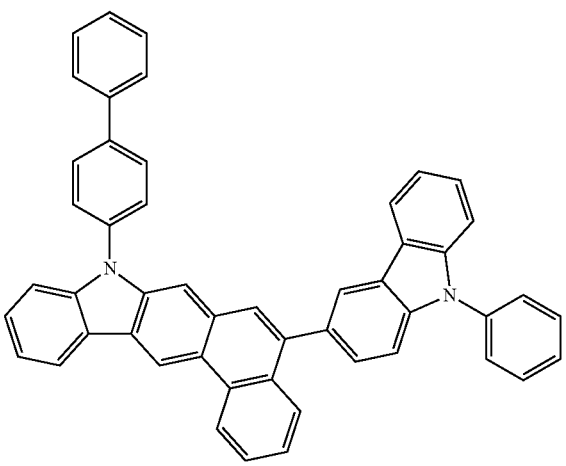
43
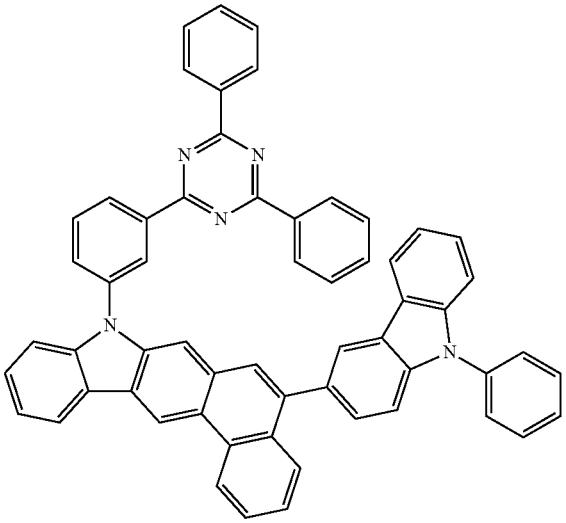

44
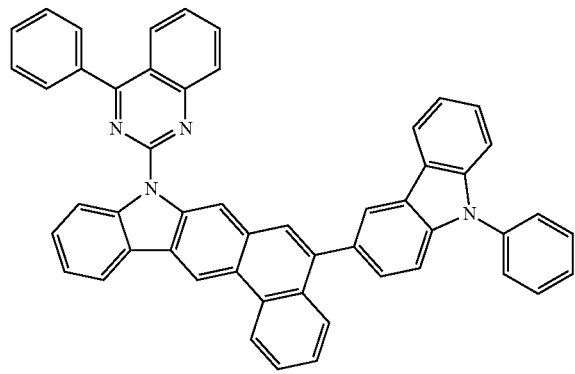
45
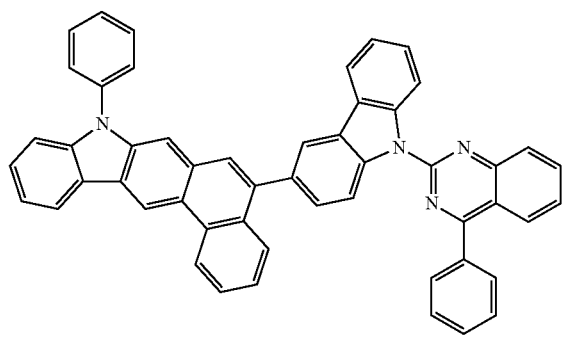
46
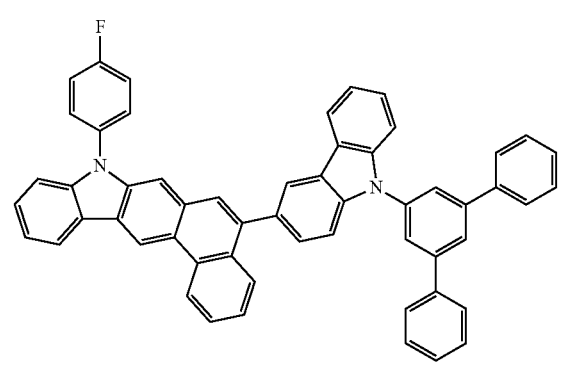
47
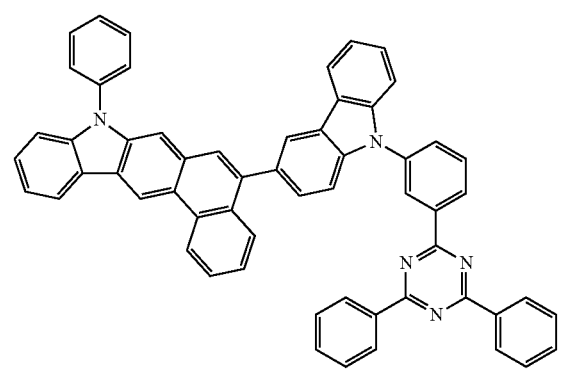
48
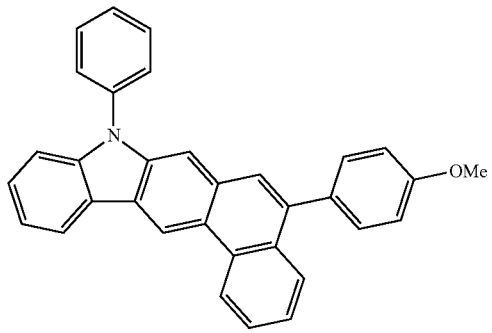
49
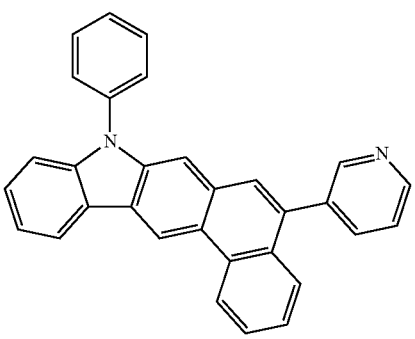
50
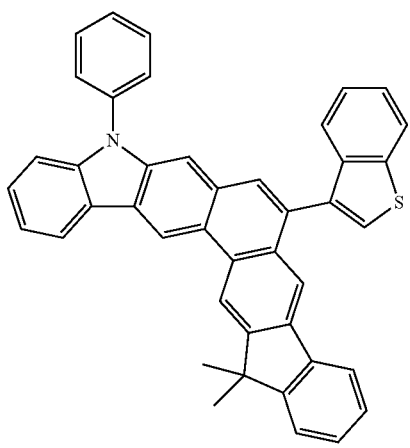
51
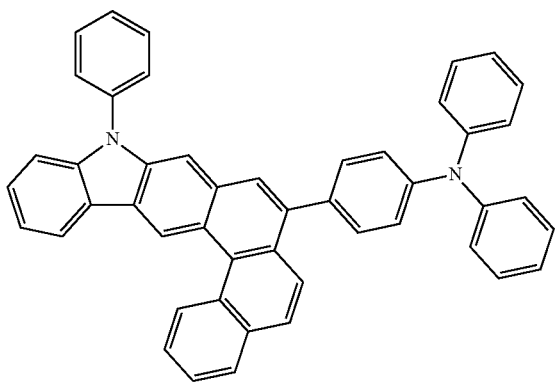

52
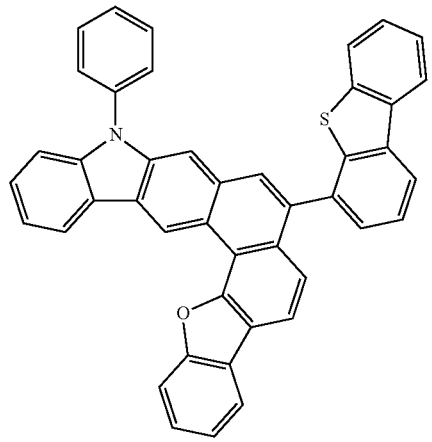
55
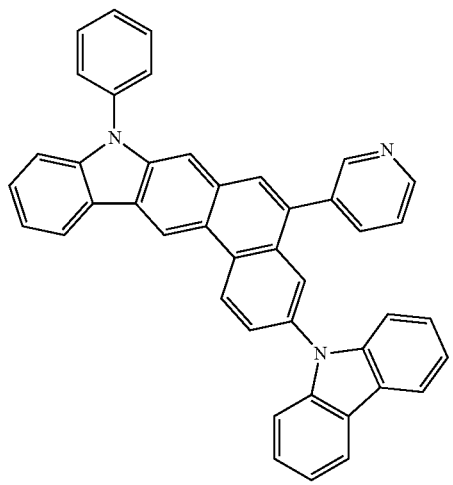
53
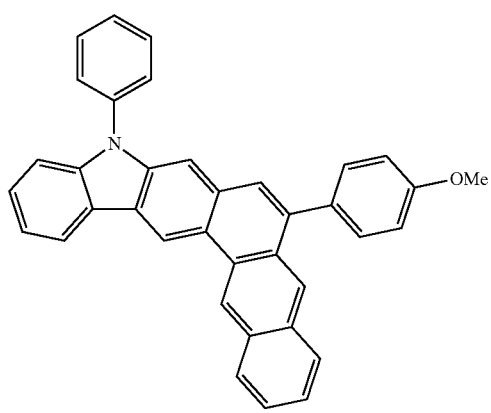
56
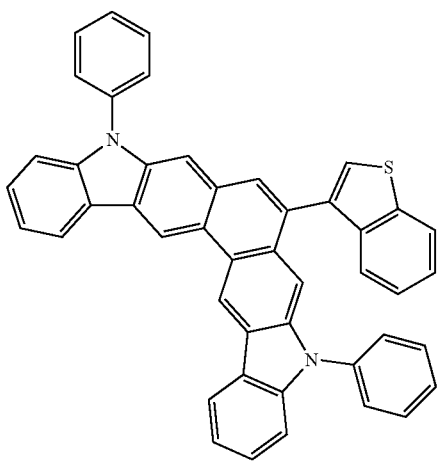
54
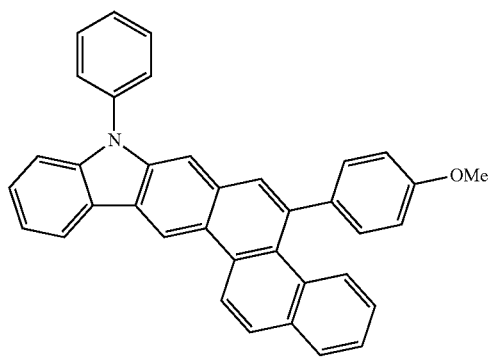
57
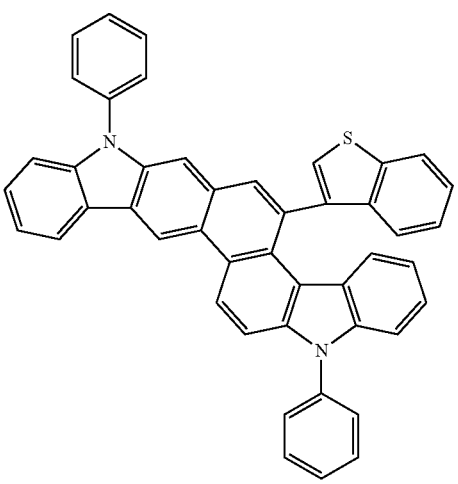

58
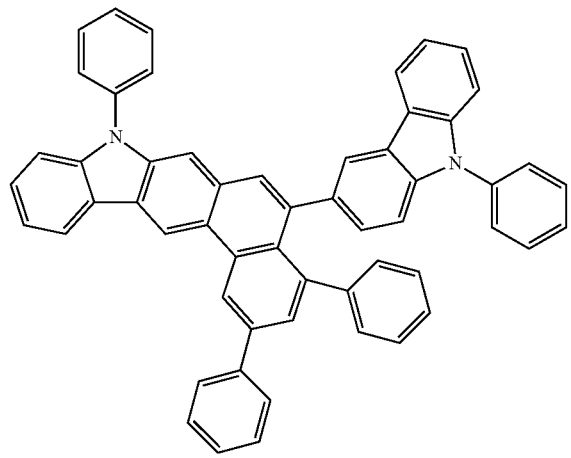
59
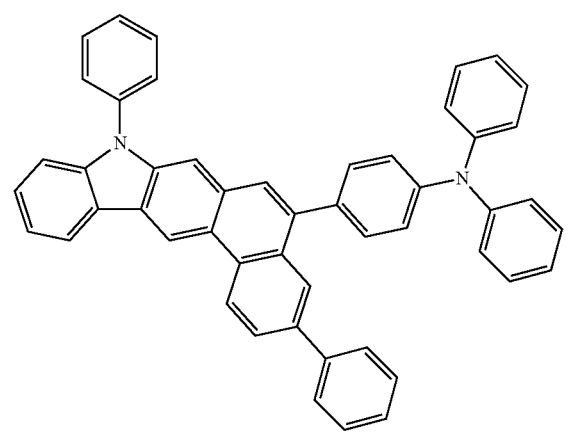
60
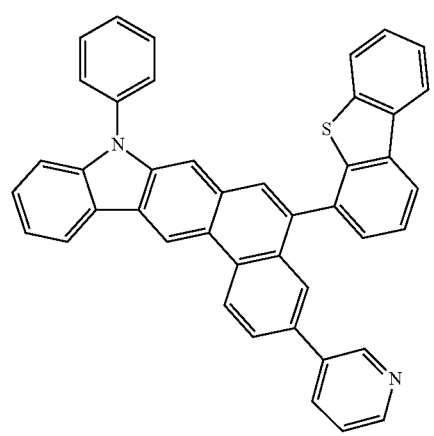
61
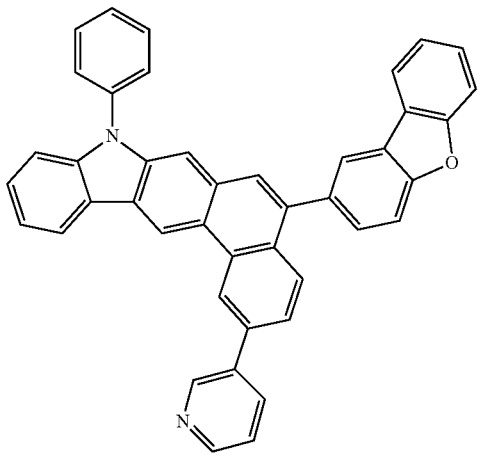
62
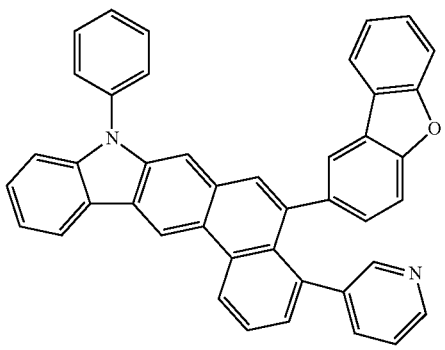
63
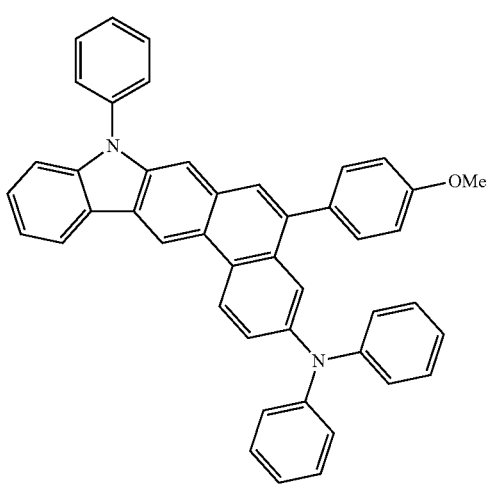

-continued

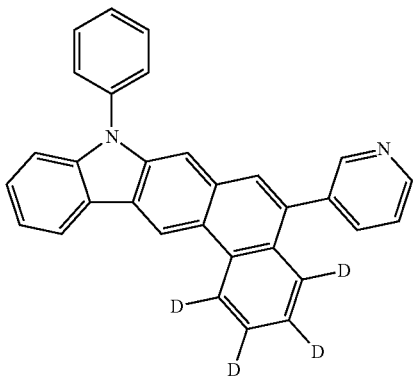

64

The heterocyclic compound of Formula 1 may be synthesized using a known organic synthesis method. A synthesis method of the heterocyclic compound of Formula 1 may be understood by those of ordinary skill in the art from the examples that will be described below.

An embodiment provides an organic light-emitting device including a first electrode, a second electrode, and an organic layer disposed between the first electrode and the second electrode, wherein the organic layer includes the compound of Formula 1 described above.

The organic layer may include at least one layer selected from among a hole injection layer, a hole transport layer, a functional layer having both hole injection and hole transport capabilities (e.g., properties) (hereinafter, "H-functional layer"), a buffer layer, an electron blocking layer, an emission layer, a hole blocking layer, an electron transport layer, an electron injection layer, and a functional layer having both electron injection and electron transport capabilities (e.g., properties) (hereinafter, "E-functional layer").

In some embodiments, the organic layer may be an emission layer, and the compound may be used as a host or a dopant in a fluorescent or phosphorescent device.

In some embodiments, the organic light-emitting device may include an electron injection layer, an electron transport layer, an emission layer, a hole injection layer, a hole transport layer, or a functional layer having both hole injection and transport capabilities; and the emission layer may further include the compound of Formula 1 above, and an anthracene-based compound, an arylamine-based compound or a styryl-based compound.

In some other embodiments, the organic light-emitting device may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include the heterocyclic compound of Formula 1 and a charge-generating material. In some embodiments, the charge-generating material may be a p-dopant, and the p-dopant may be a quinine derivative, a metal oxide, or a cyano group-containing compound.

In some embodiments, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include the compound of Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

The compound in the EML (emission layer) may serve as a host. For example, the compound of Formula 1 may serve as a green phosphorescent host emitting green light. The compound of Formula 1 in the emission layer may serve as a fluorescent or phosphorescent dopant emitting red light, green light, or blue light.

FIG. 1 is a schematic sectional view of an organic light-emitting device according to an embodiment. Hereinafter, a structure of an organic light-emitting device according to an embodiment and a method of manufacturing the same will now be described with reference to FIG. 1.

A substrate (not shown) may be a suitable substrate that is used in existing organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer(s) is disposed on the first electrode.

The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about 10-8 torr to about 10-3 torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of the heterocyclic compound of Formula 1 or a suitable material that is commonly used to form a HIL. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copper-phthalocyanine, 4,4',4''-tris (3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrene sulfonate) (PEDOT/PSS), polyaniline/camphor sulfonic acid (Pani/CSA), and polyaniline)/poly(4-styrenesulfonate (PANI/PSS).

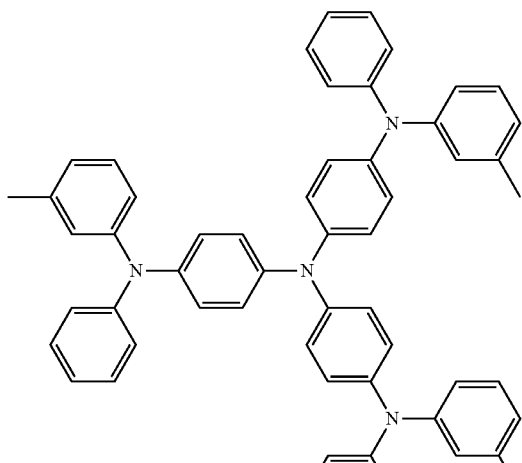

m-MTDATA

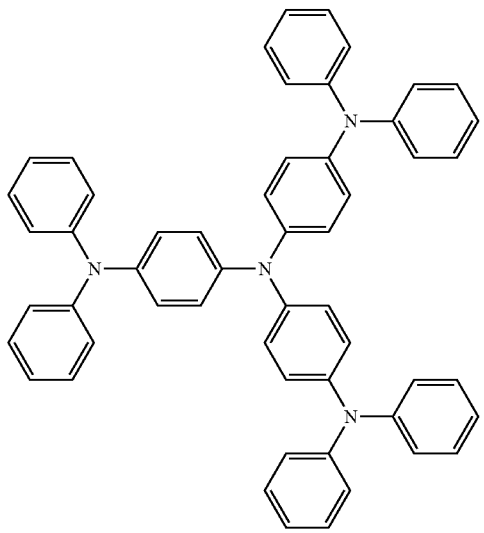

TDATA

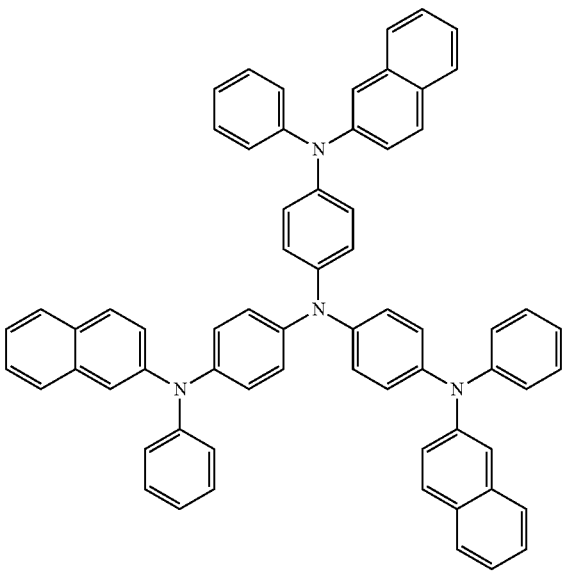

2-TNATA

The thickness of the HIL may be from about 100 Å to about 10000 Å, and in some embodiments, from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of the heterocyclic compound of Formula 1 or a suitable hole transporting material. Non-limiting examples of suitable known HTL forming materials are carbazole derivatives, such as N-phenylcarbazole or polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine) (NPB).

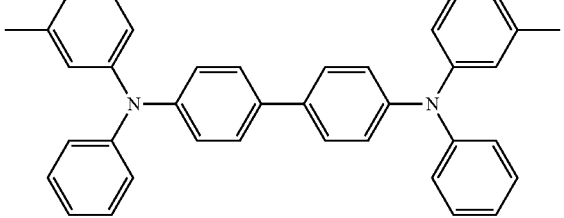

TPD

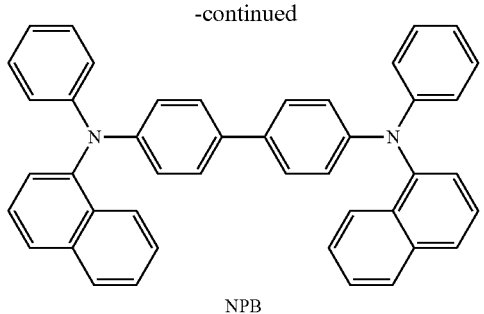

NPB

The thickness of the HTL may be from about 50 Å to about 2000 Å, and in some embodiments, from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 350 below:

<Formula 350>

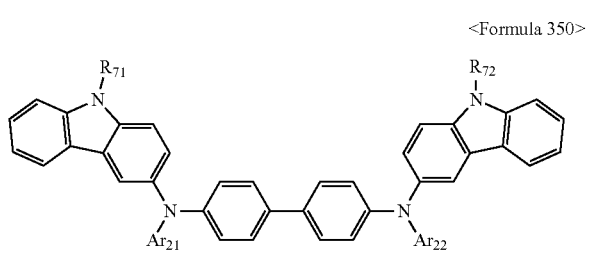

In Formula 350, $Ar_{21}$ and $Ar_{22}$ may be each independently a substituted or unsubstituted C5-C60 alkyl group.

In Formulae 350, $R_{71}$ and $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. In some embodiments, $R_{71}$ and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In some non-limiting embodiments, at least one of the HIL, HTL, and H-functional layer may include at least one of the following compounds, but not limited thereto:

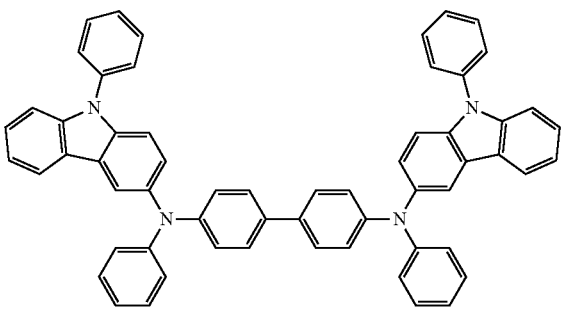

301

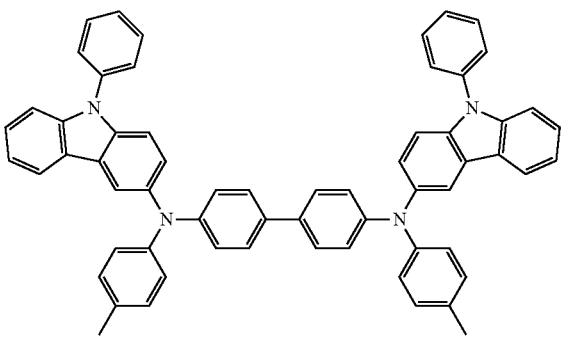

302

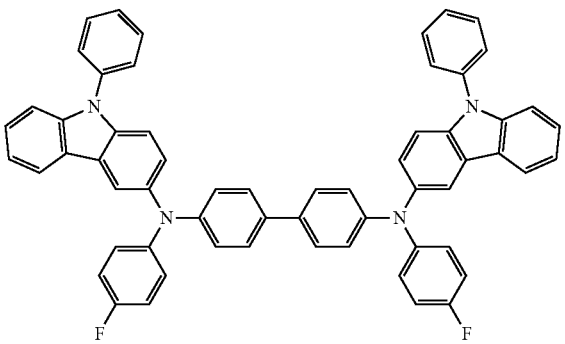

303

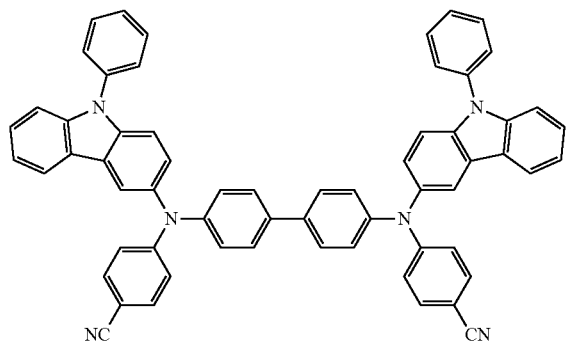

304

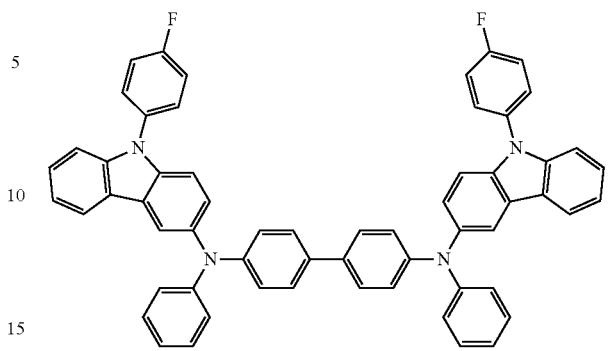

308

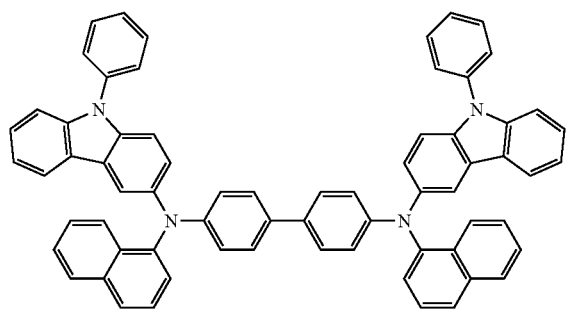

305

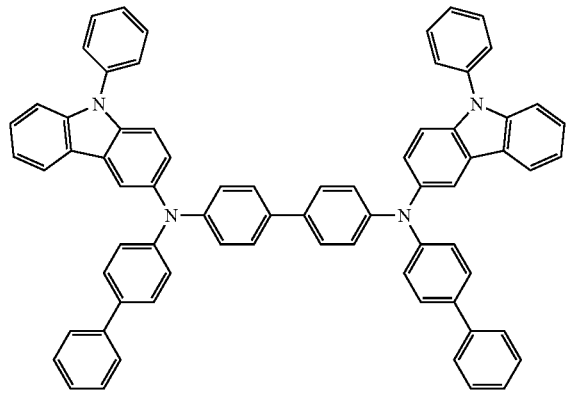

306

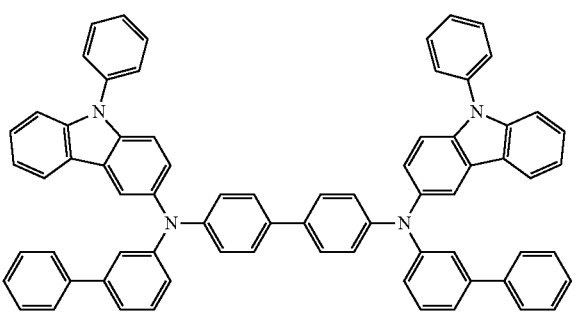

307

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

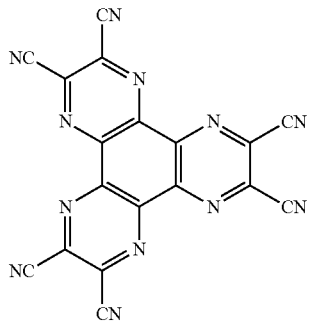

<Compound 200>

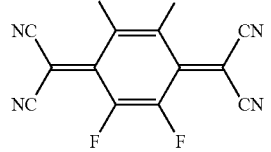

<F4-CTNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include a suitable hole injecting material or hole transporting material that are widely known. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the heterocyclic compound of Formula 1. For example, the compound of Formula 1 may be used as a host or a dopant. The EML may be formed using a variety of known light-emitting materials, in addition to the compound of Formula 1. In some embodiments, the EML may also be formed using a known host and a dopant. Dopants that may be used to form the EML may include either a fluorescent dopant or a phosphorescent dopant which are widely known in the art.

Non-limiting example of known hosts are Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

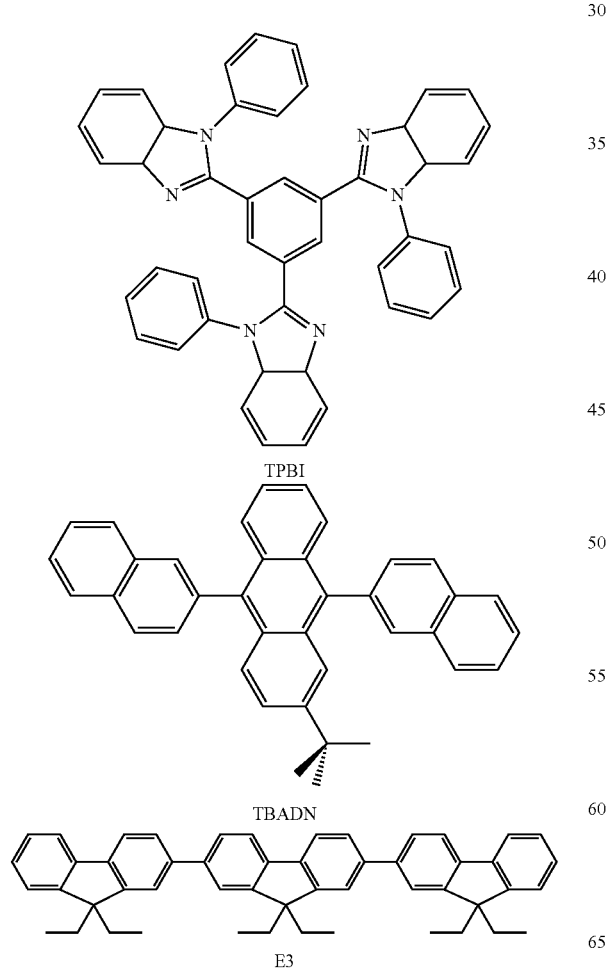

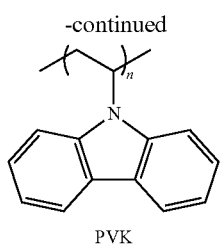

PVK

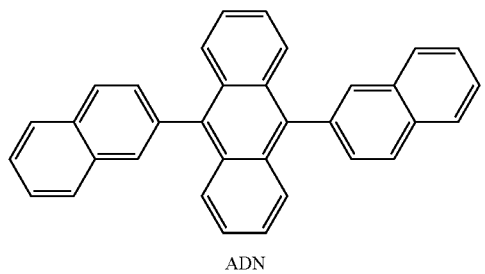

ADN

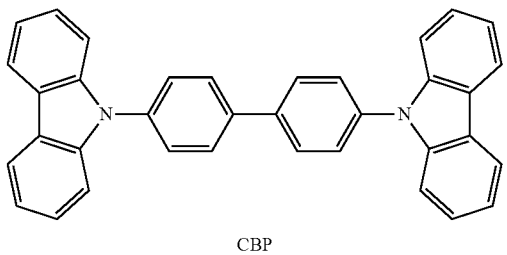

CBP

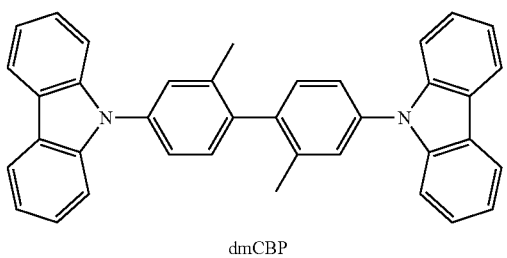

dmCBP

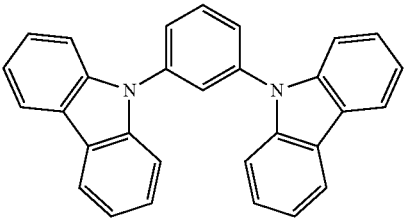

501

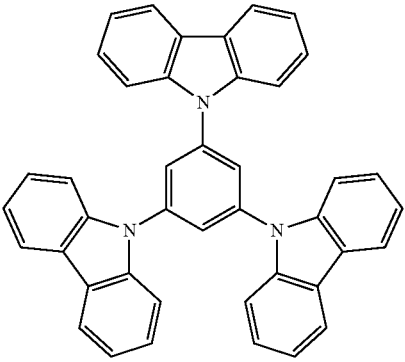

502

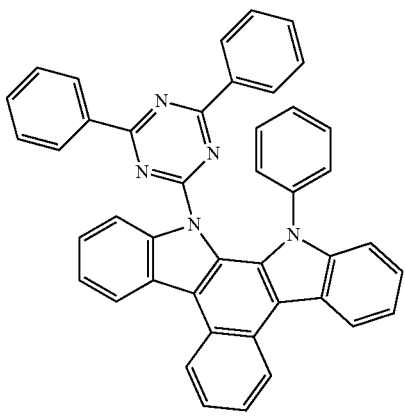
503
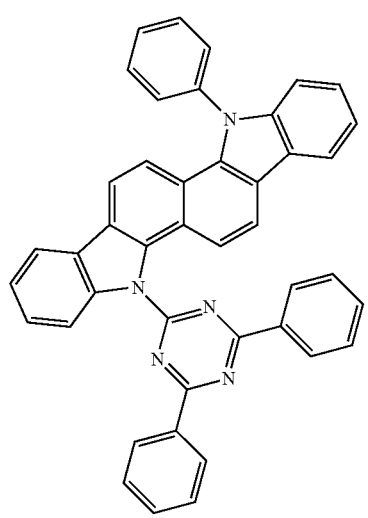
504
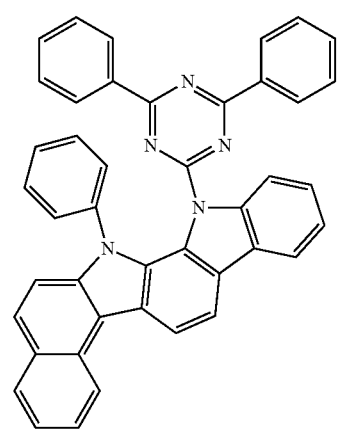
505
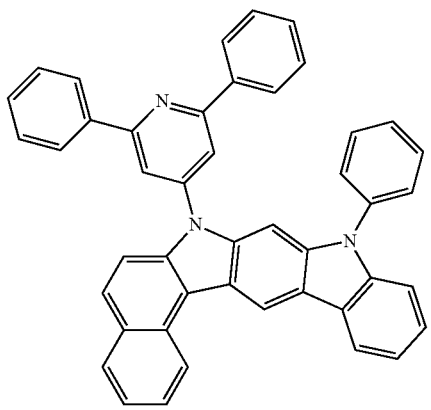
506
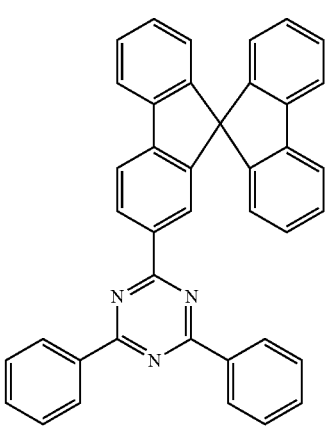
507
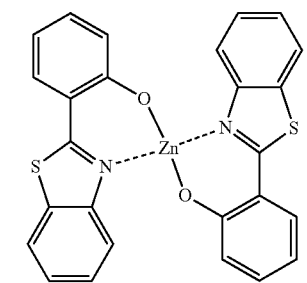
508
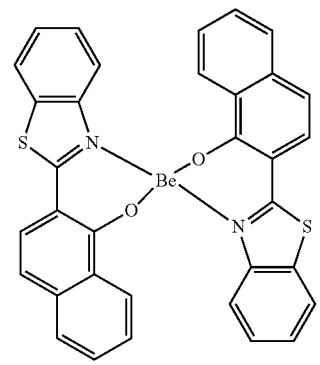
509
In some embodiments, an anthracene-based compound represented by Formula 400 below may be used as the host.

<Formula 400>

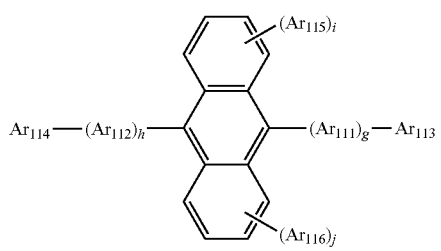

In Formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group, but are not limited thereto.

In Formula 400 above, g, h, I, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group, but are not limited thereto.

For example, the anthracene compound of Formula 400 above may be one of the compounds represented by the following formulae, but is not limited thereto:

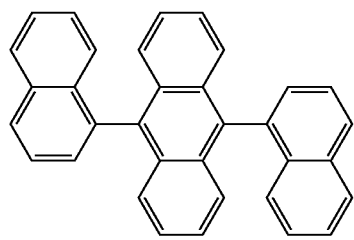

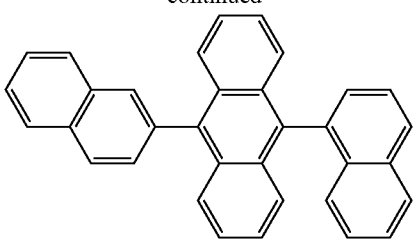

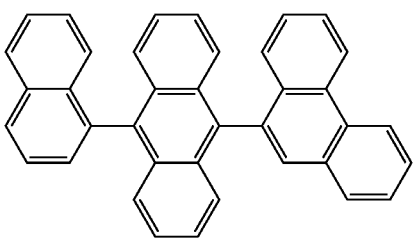

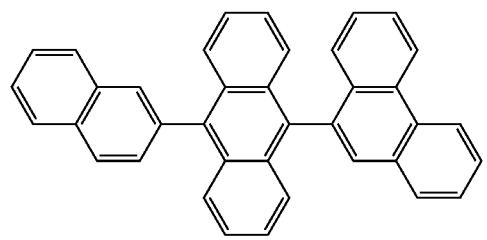

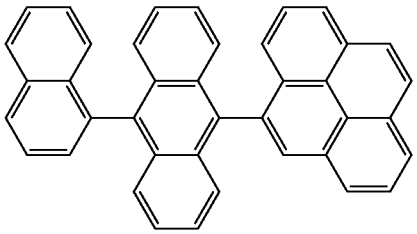

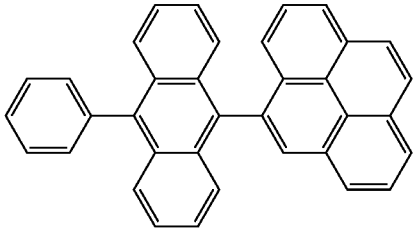

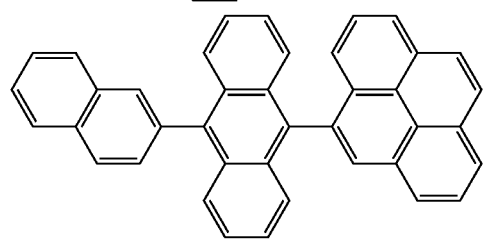

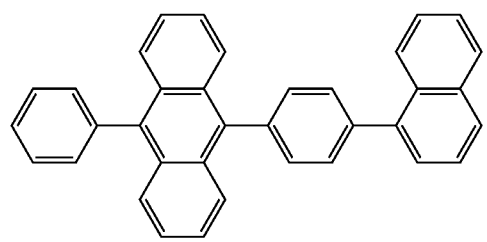

-continued
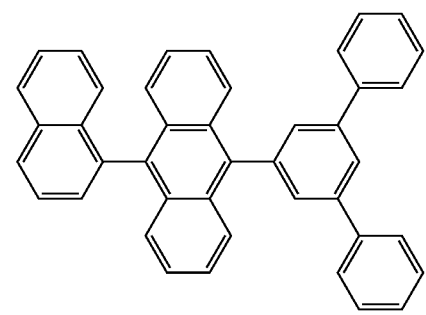
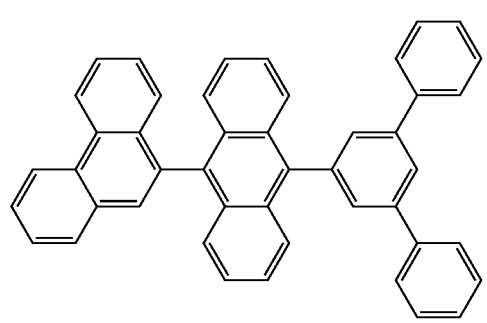
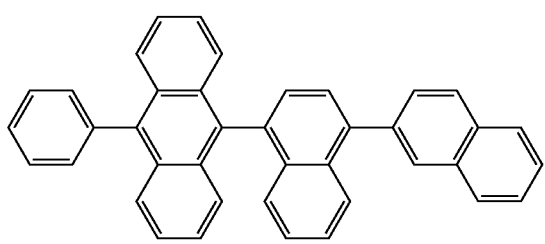
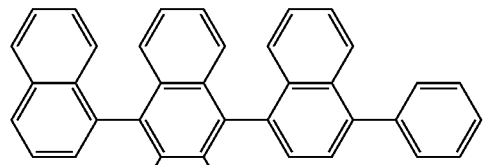
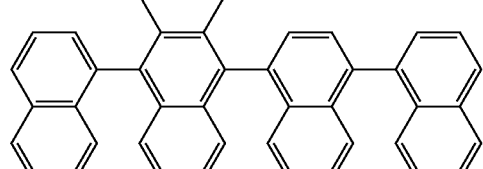
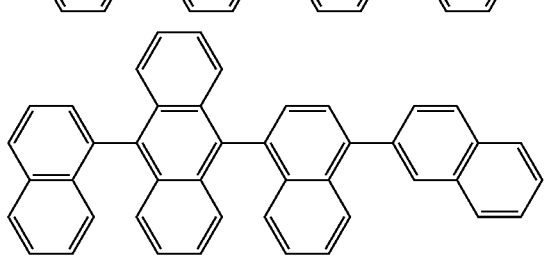
-continued
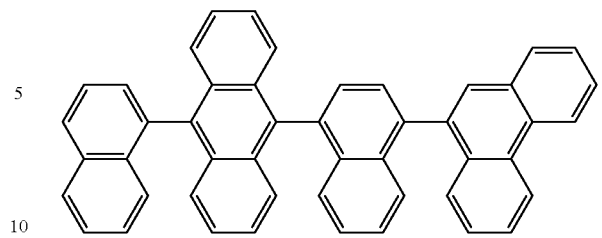
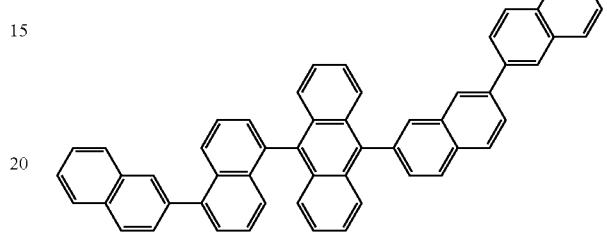
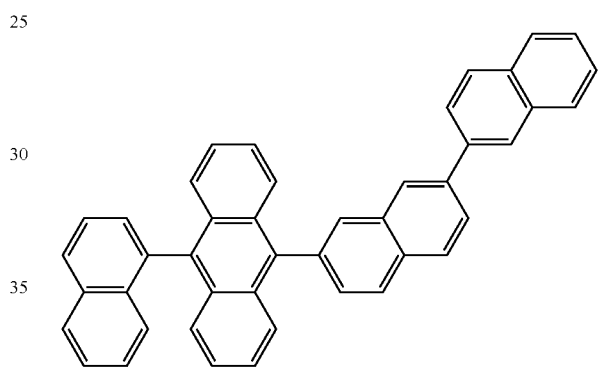
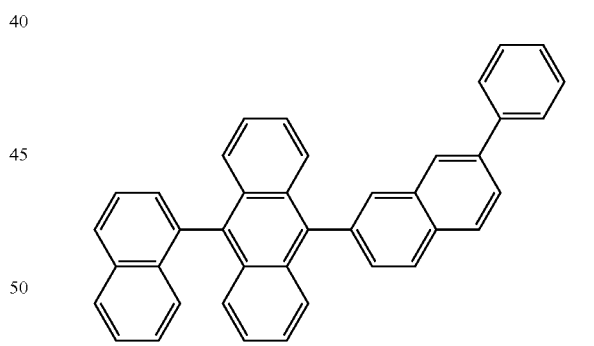
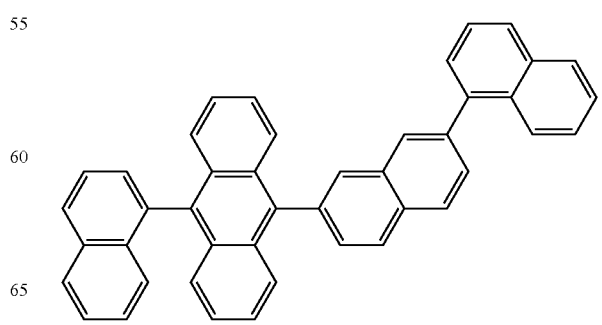

51
-continued
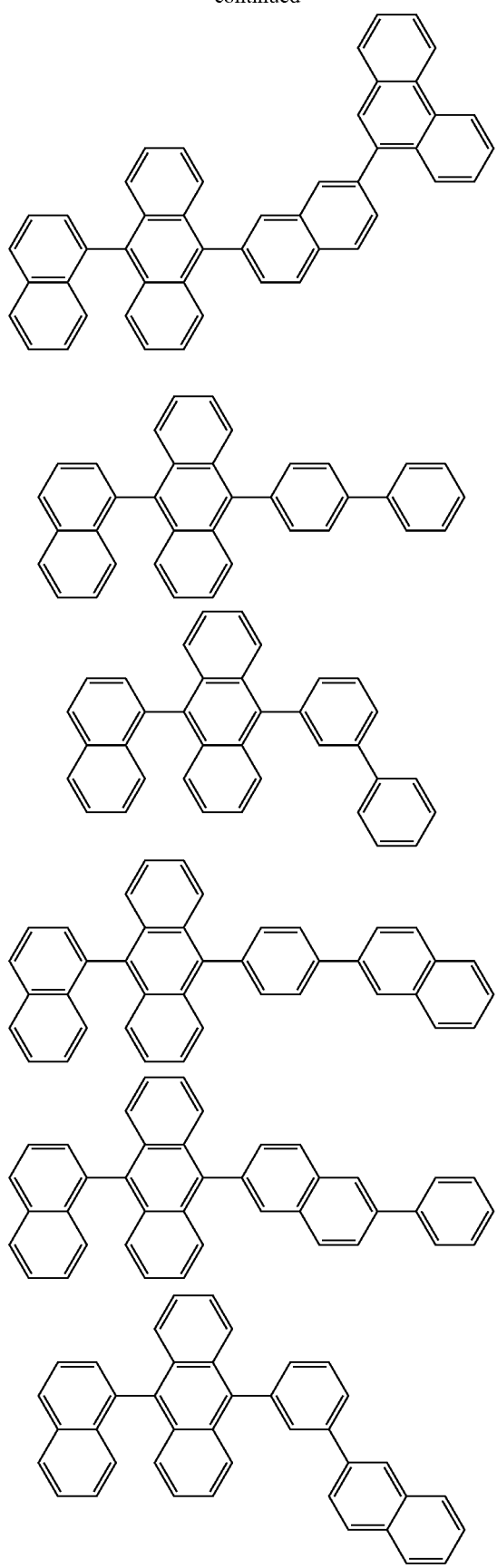
52
-continued
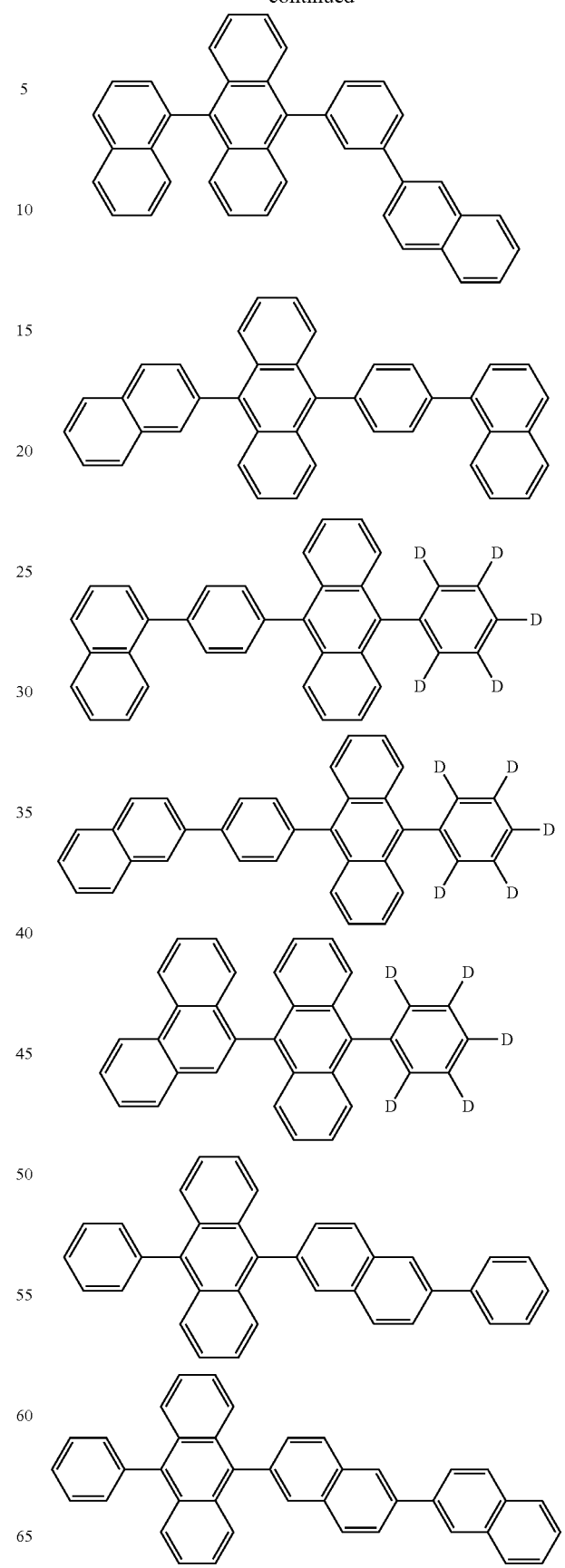

-continued
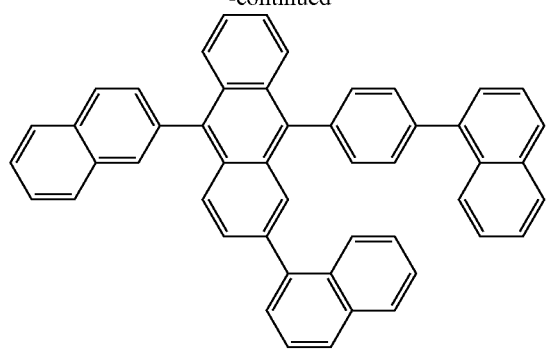
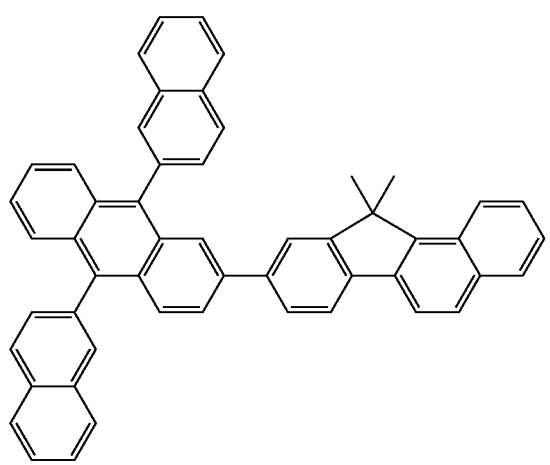
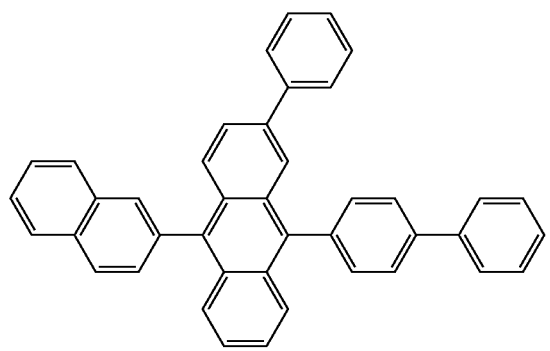
-continued
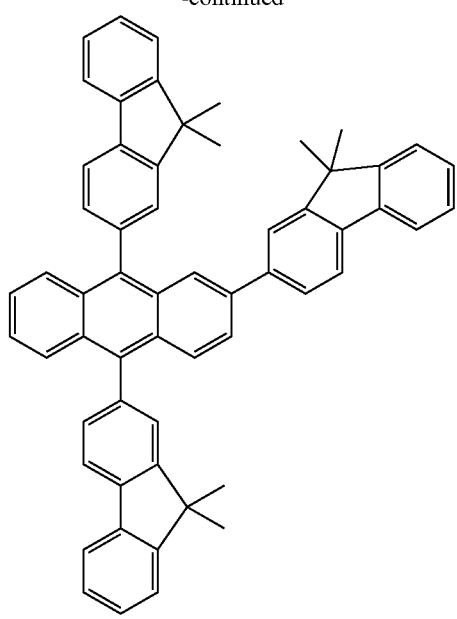
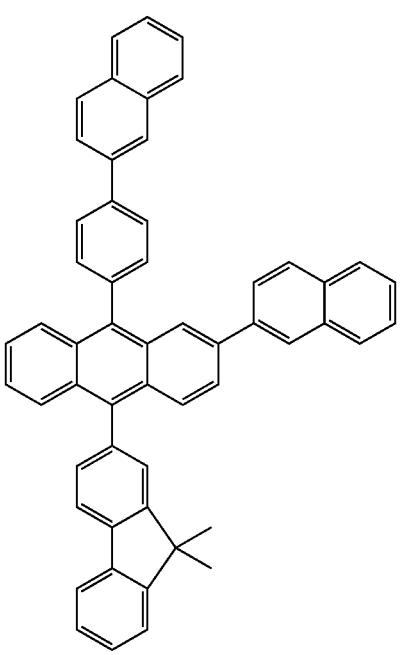
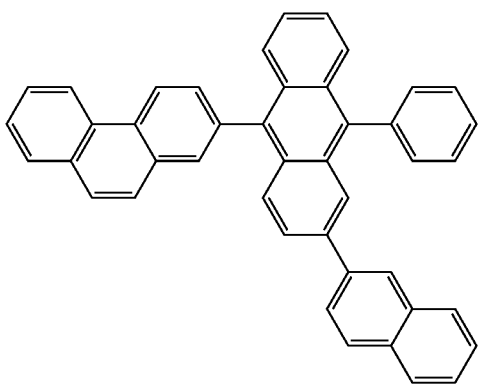
In some embodiments, an anthracene-based compound represented by Formula 401 below may be used as the host.

Formula 401

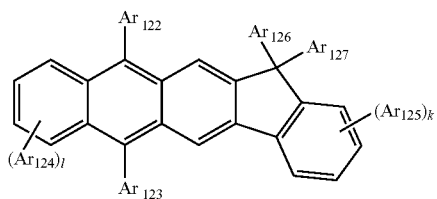

Ar$_{122}$ to Ar$_{125}$ in Formula 401 above may be as defined above in conjunction with Ar$_{113}$ of Formula 400, and thus detailed descriptions thereof will not be repeated here.

Ar$_{126}$ and Ar$_{127}$ in Formula 401 above may be each independently a C$_1$-C$_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

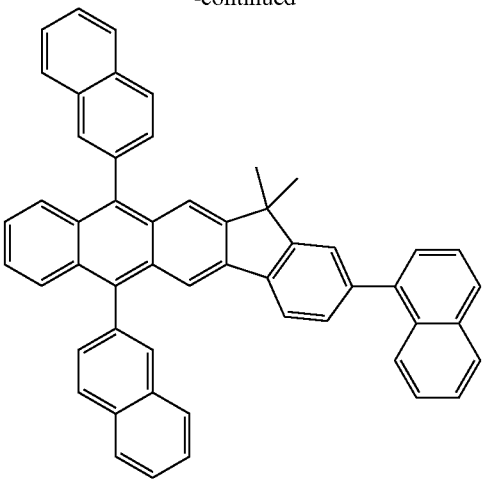

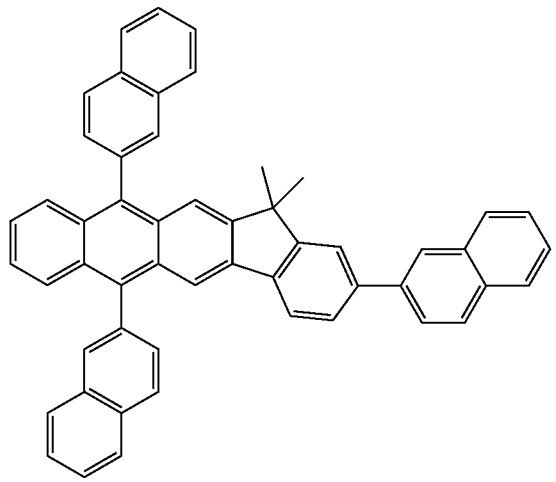

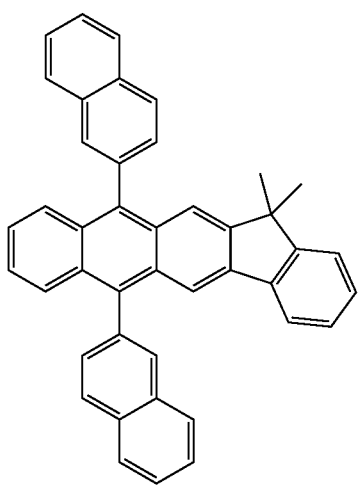

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant are compounds represented by the following formulae.

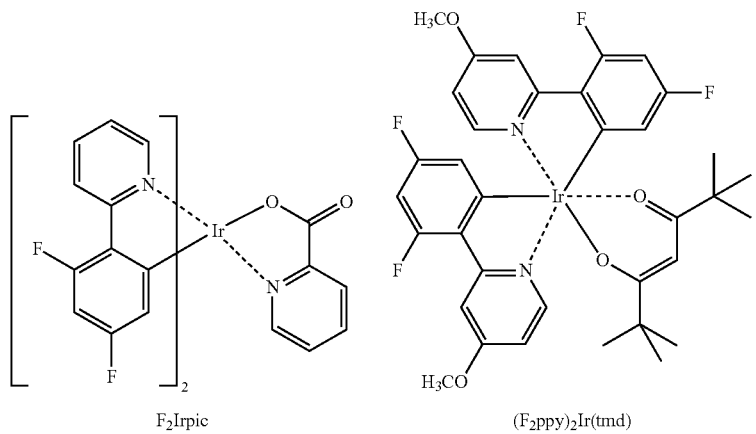
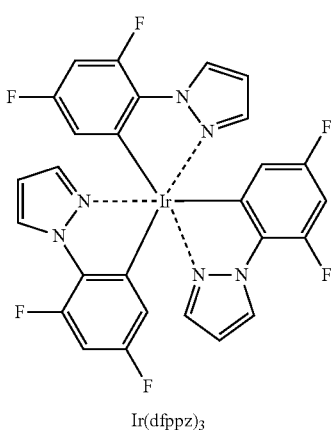
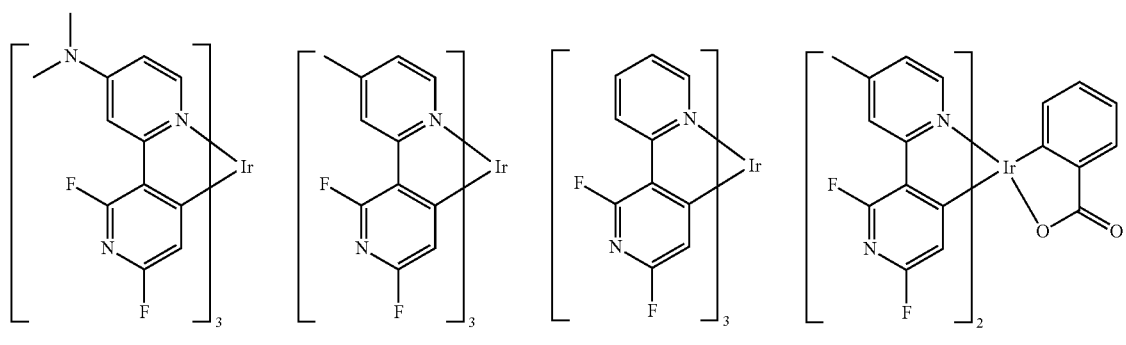
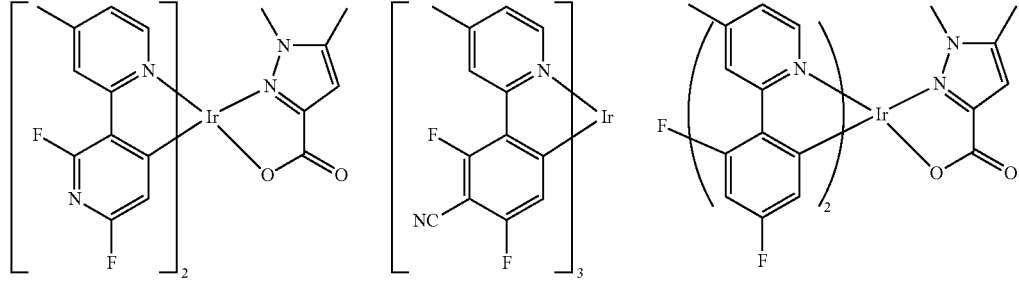
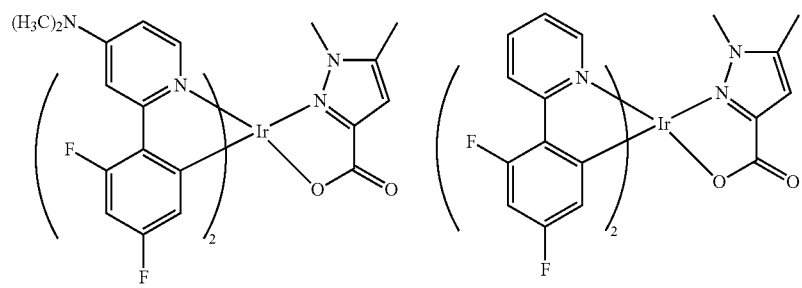
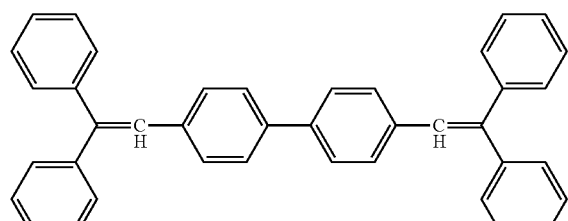

-continued
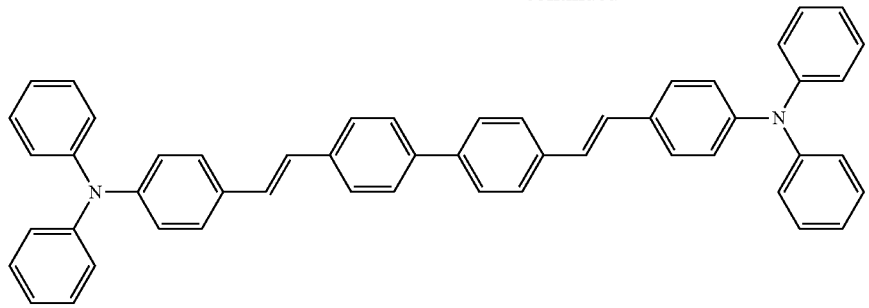
DPAVBi
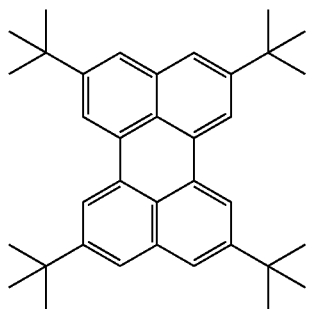
TBPe
Non-limiting examples of the red dopant are compounds represented by the following formulae.
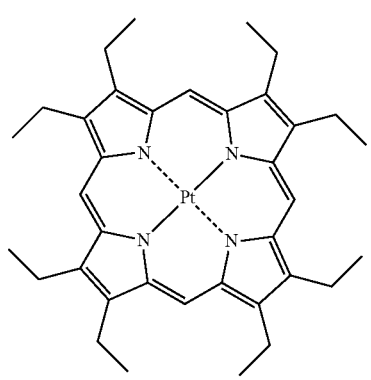
PtOEP
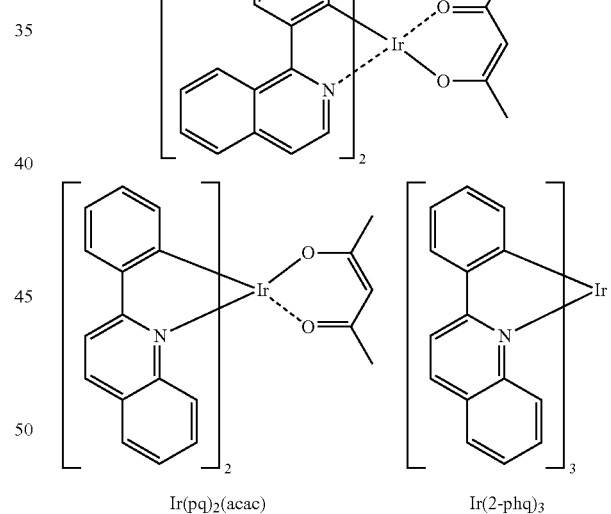
Ir(pq)₂(acac)    Ir(2-phq)₃
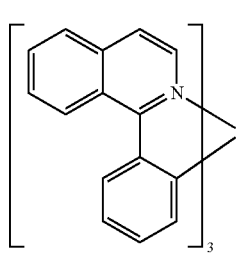
Ir(piq)₃
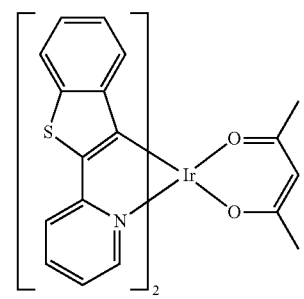
Btp₂Ir(acac)
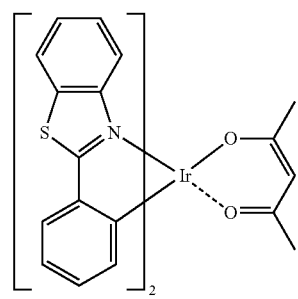
Ir(BT)₂(acac)

-continued
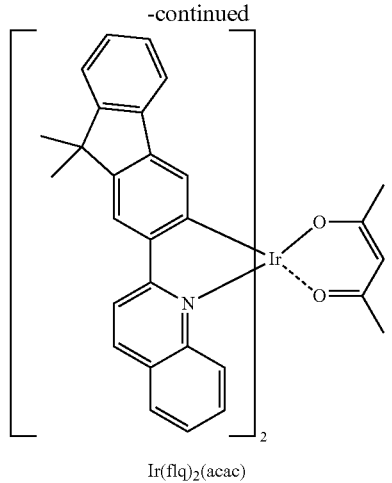
Ir(flq)₂(acac)
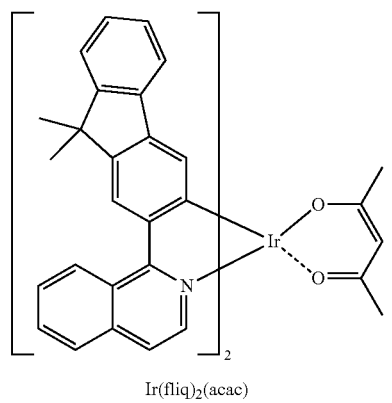
Ir(fliq)₂(acac)
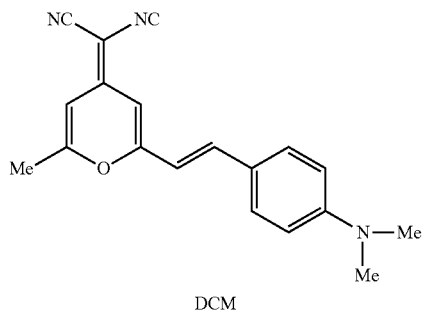
DCM
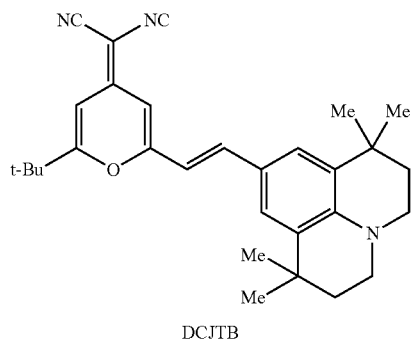
DCJTB
Non-limiting examples of the green dopant are compounds represented by the following formulae.
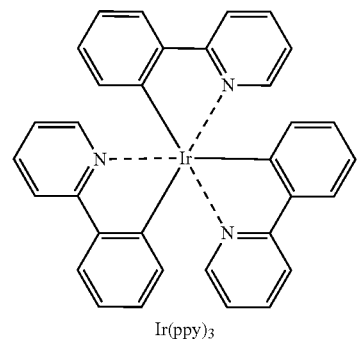
Ir(ppy)₃
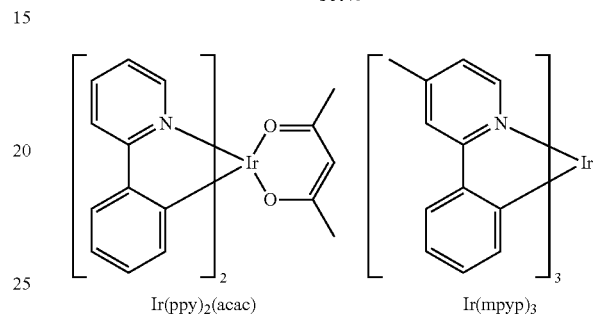
Ir(ppy)₂(acac)   Ir(mpyp)₃
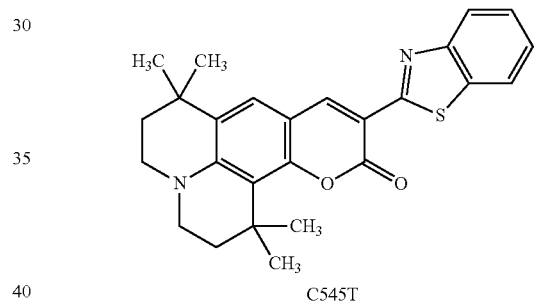
C545T
Non-limiting examples of the dopant that may be used in the EML are Pt complexes represented by the following formulae.
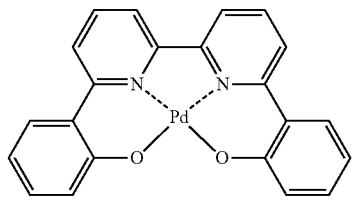
D1
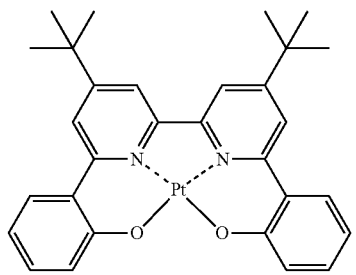
D2

-continued
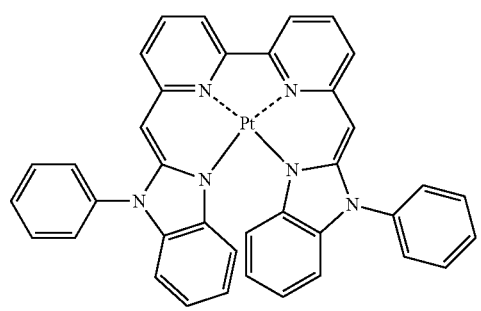
D3
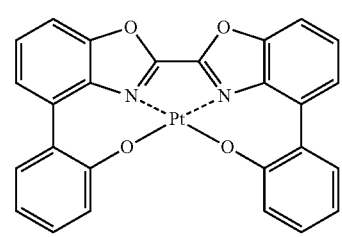
D4
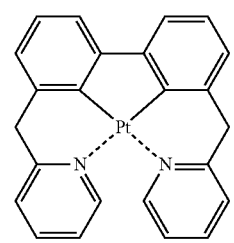
D5
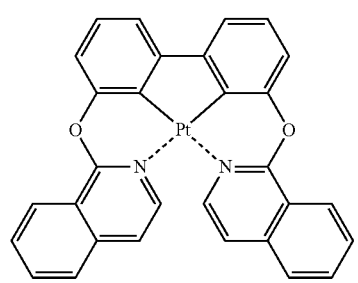
D6
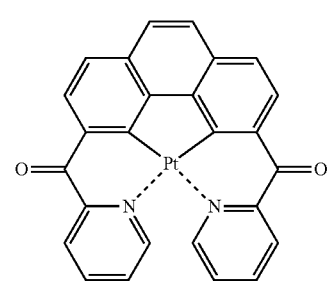
D7
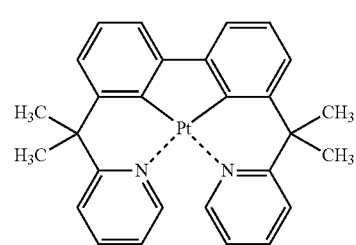
D8
-continued
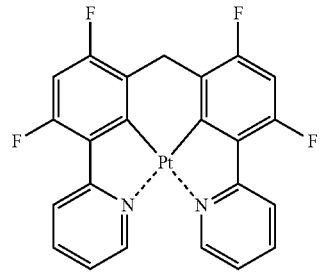
D9
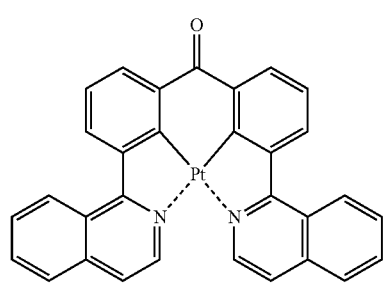
D10
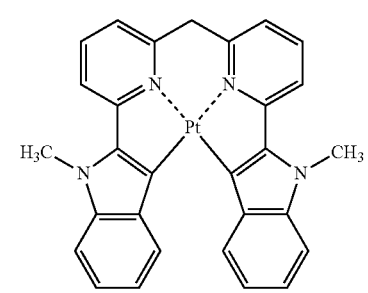
D11
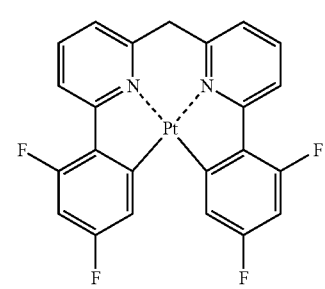
D12
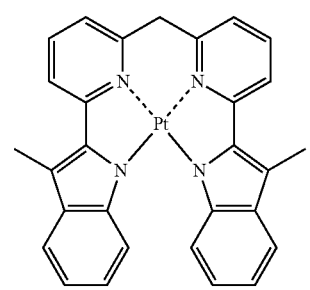
D13

D14 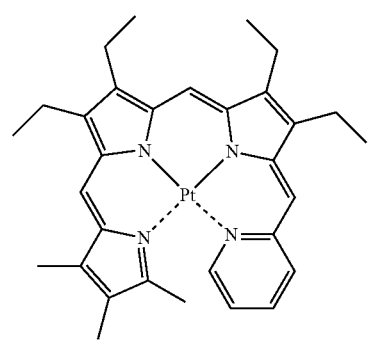
D15 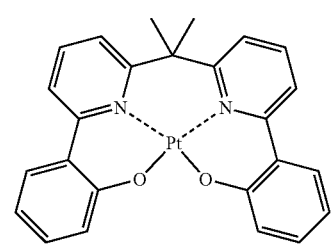
D16 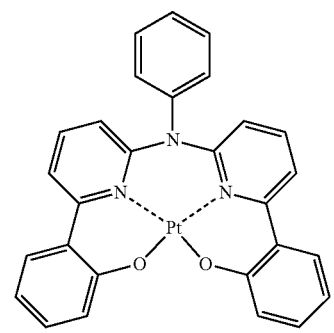
D17 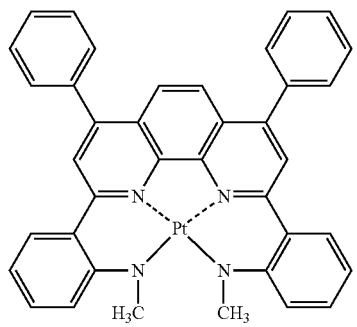
D18 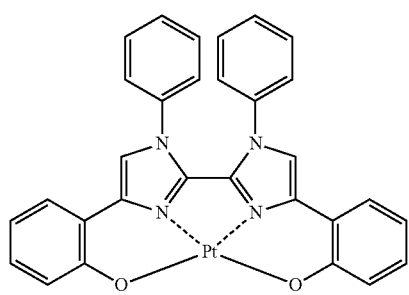
D19 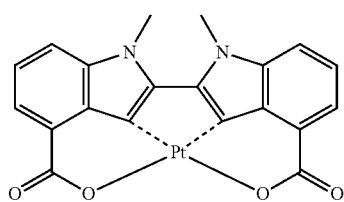
D20 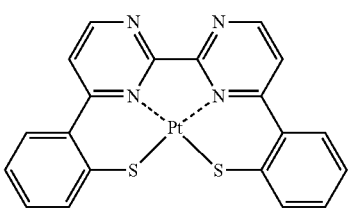
D21 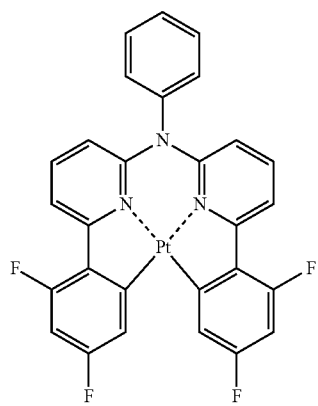
D22 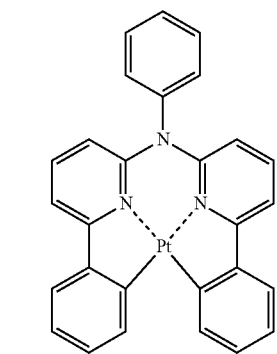
D23 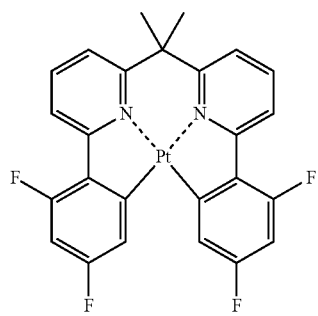

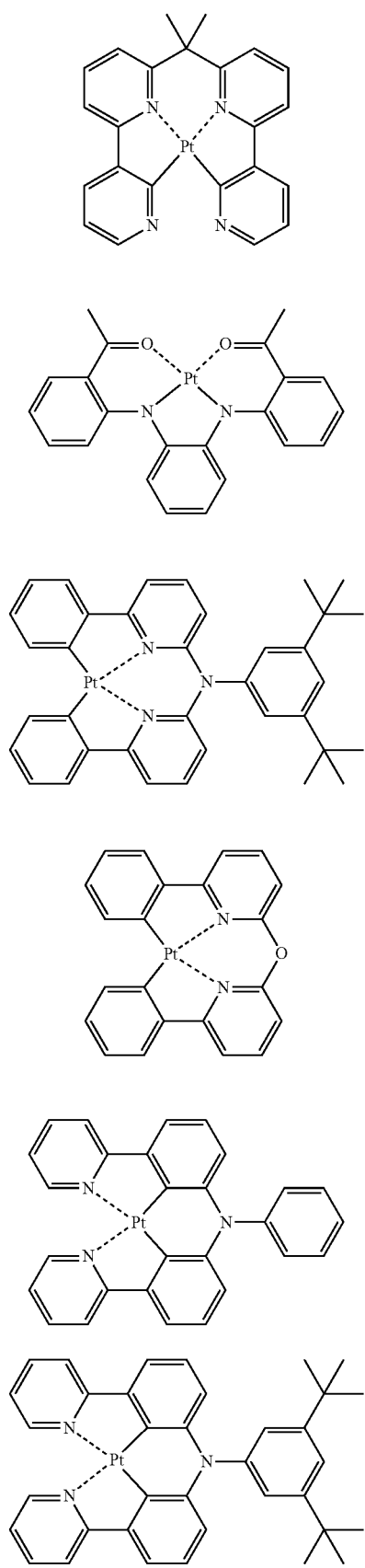
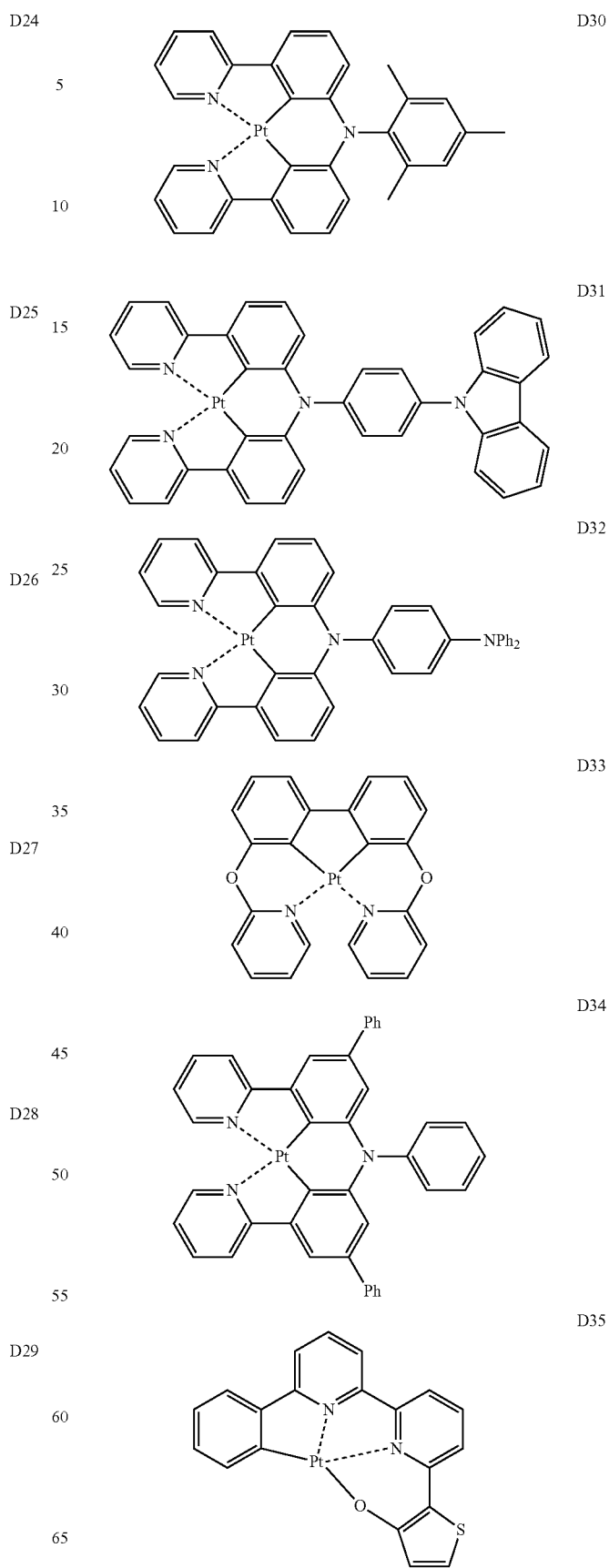

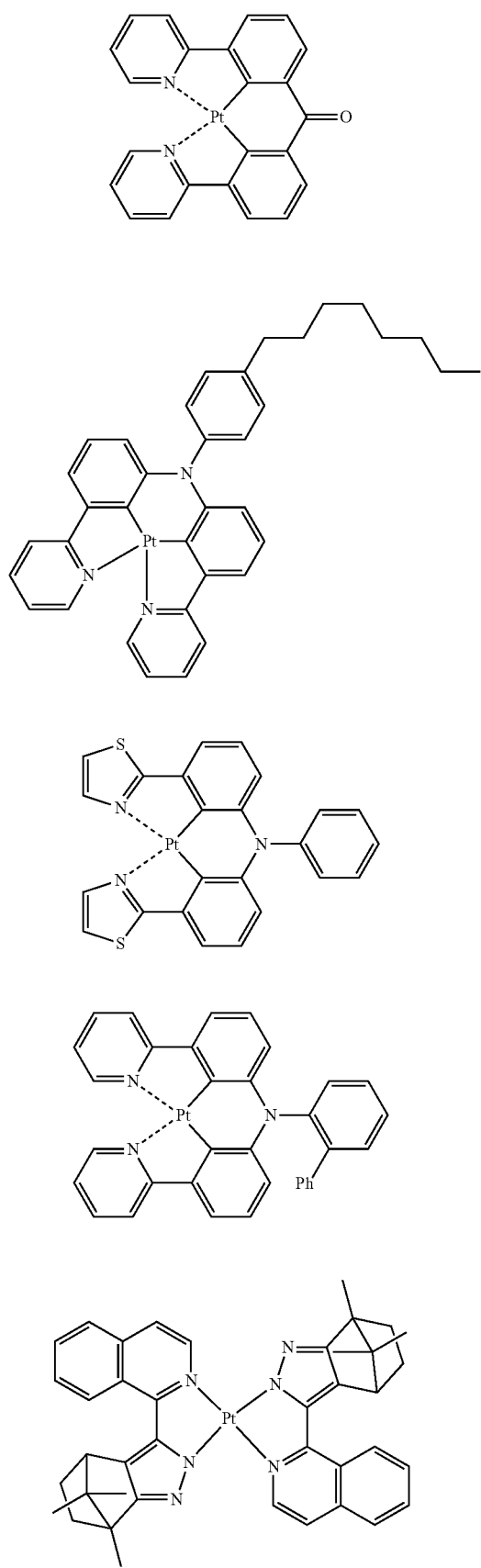
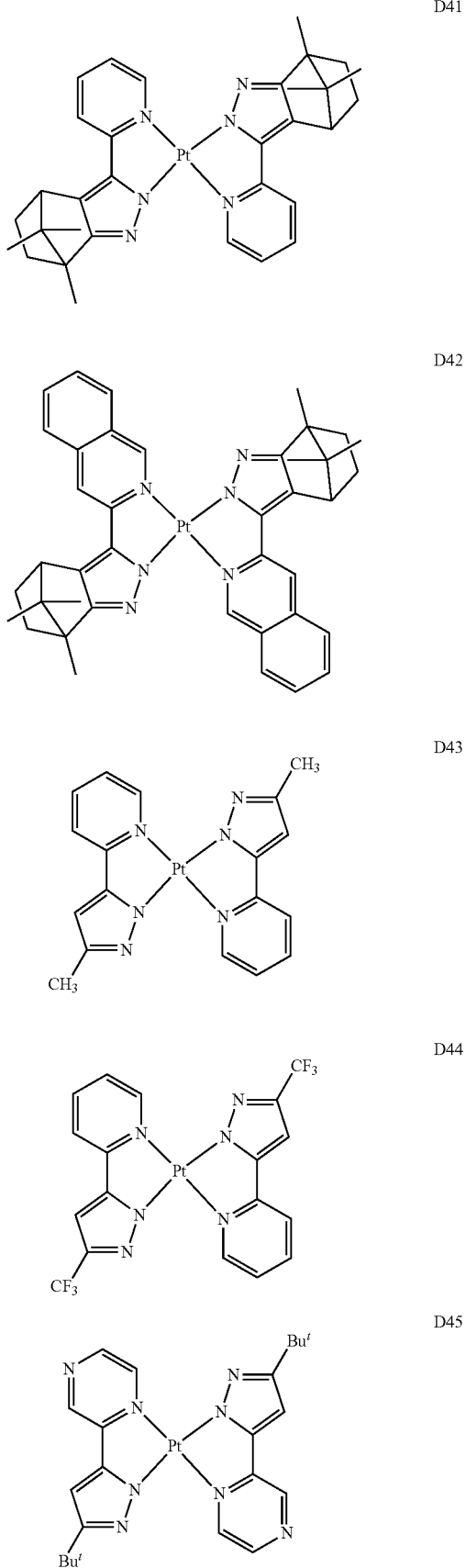

-continued
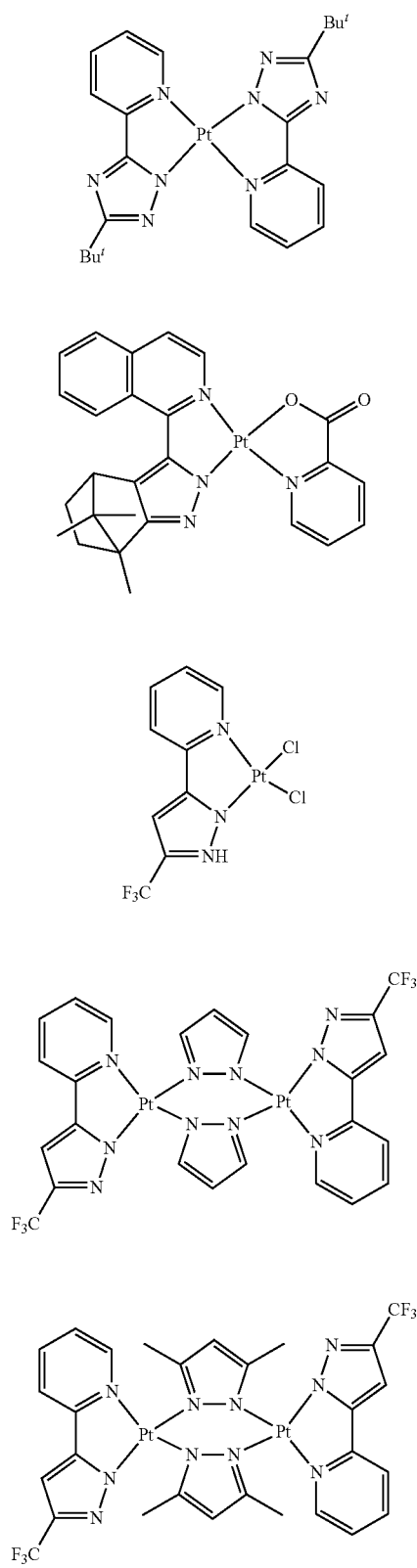
D46
D47
D48
D49
D50
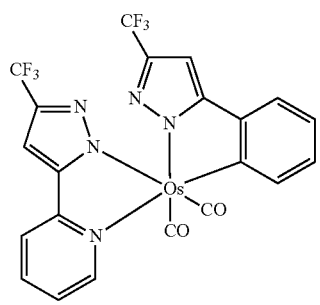
Os(fppz)₂(CO)₂
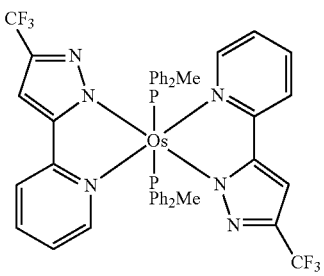
Os(fppz)₂(PPh₂Me)₂
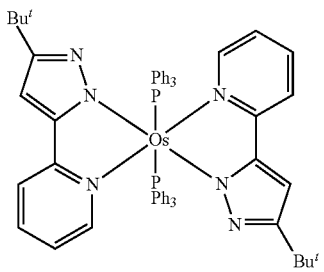
Os(bppz)₂(PPh₃)₂
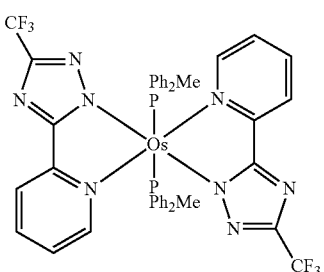
Os(fptz)₂(PPh₂Me)₂
Non-limiting examples of the dopant that may be used in the EML are Os complexes represented by the following formulae.

-continued

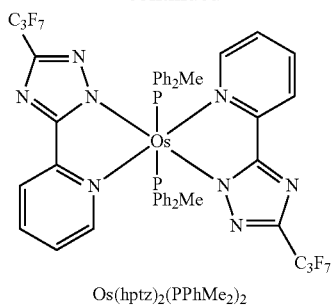

Os(hptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be the compound of Formula 1 above or a suitable material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate (Bebq₂), 9,10-di(naphthalene-2-yl)anthracene (ADN), Compound 201, and Compound 202, but are not limited thereto.

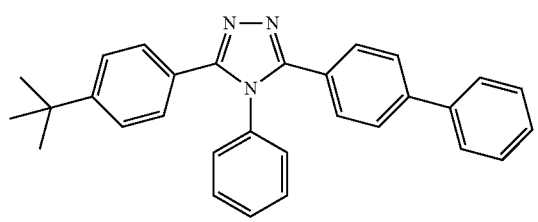

TAZ

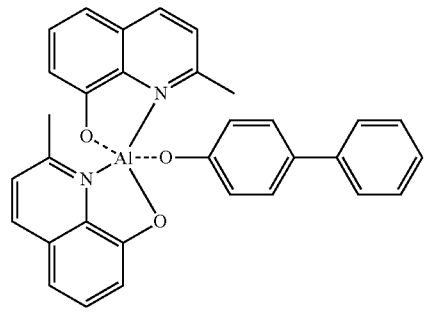

BAlq

-continued

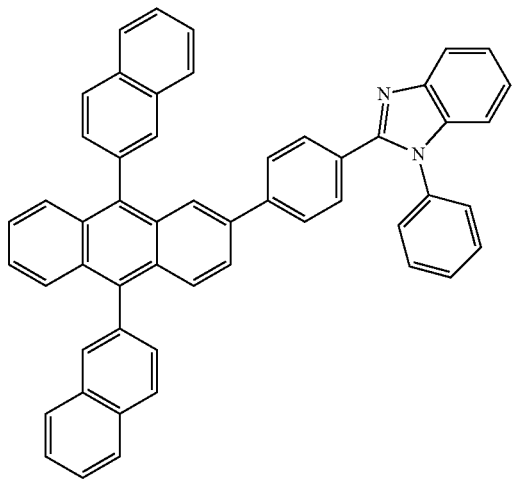

<Compound 201>

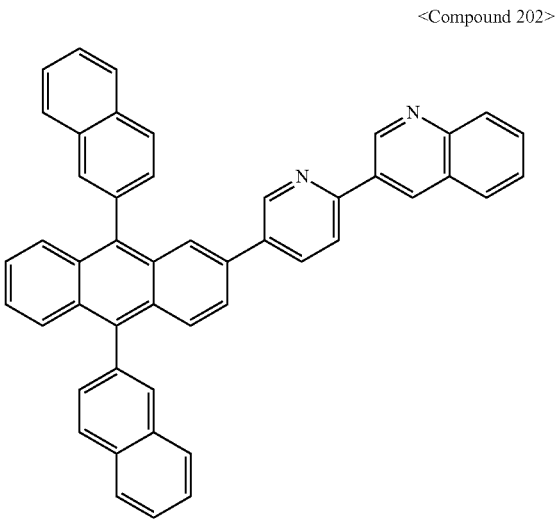

<Compound 202>

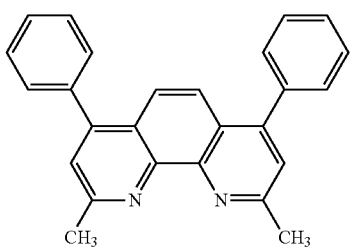

BCP

The thickness of the ETL may be from about 100 Å to about 1000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to a suitable electron-transporting organic compound.

The metal-containing material may include a lithium (Li) complex. Non-limiting examples of the Li complex are lithium quinolate (LiQ) and Compound 203 below:

<Compound 203>

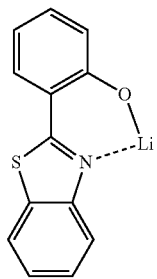

Then, an EIL, which facilitates injection of electrons from the cathode, may be formed on the ETL. A suitable electron-injecting material may be used to form the EIL.

Non-limiting examples of materials for forming the EIL are LiF, NaCl, CsF, Li$_2$O, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. Material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the embodiments are not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. A suitable hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

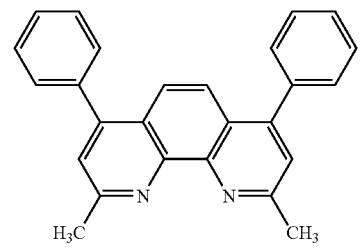

BCP

The thickness of the HBL may be from about 20 Å to about 1000 Å, and in some embodiments, from about 30 Å to about 300 Å. When the thickness of the FIBL is within these ranges, the HBL may have improved hole blocking ability without a substantial increase in driving voltage.

According to an embodiment, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may be formed of the compound of Formula 1 by using a deposition method or may be formed using a wet method of coating a solution of the compound of Formula 1.

Hereinafter, embodiments will be described in detail with reference to the following synthesis examples and other examples. However, these examples are for illustrative purposes only and are not intended to limit the scope of the embodiments.

Reaction schemes for synthesis are as follows. Detailed descriptions of synthesis methods will be provided below.

77 78
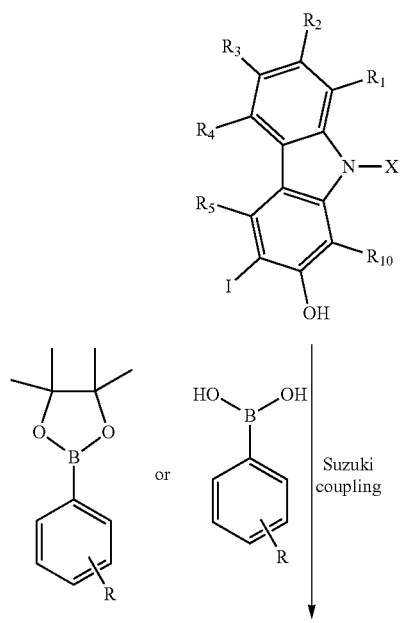 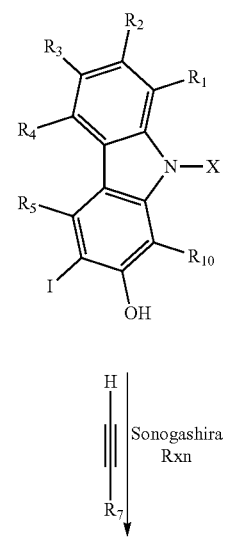
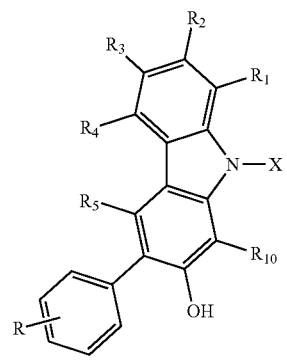 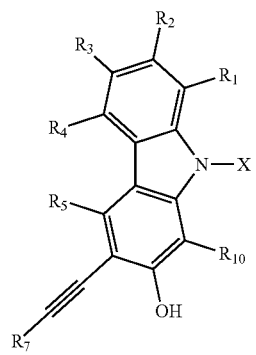
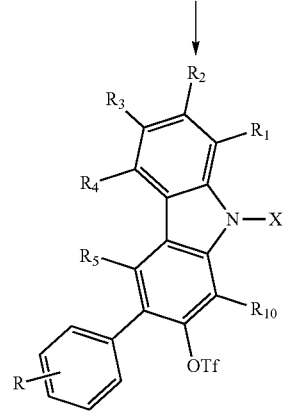 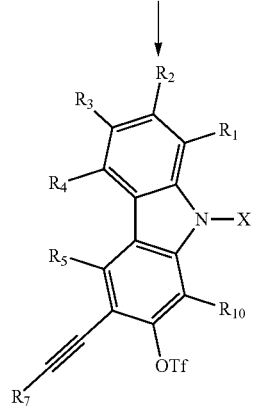

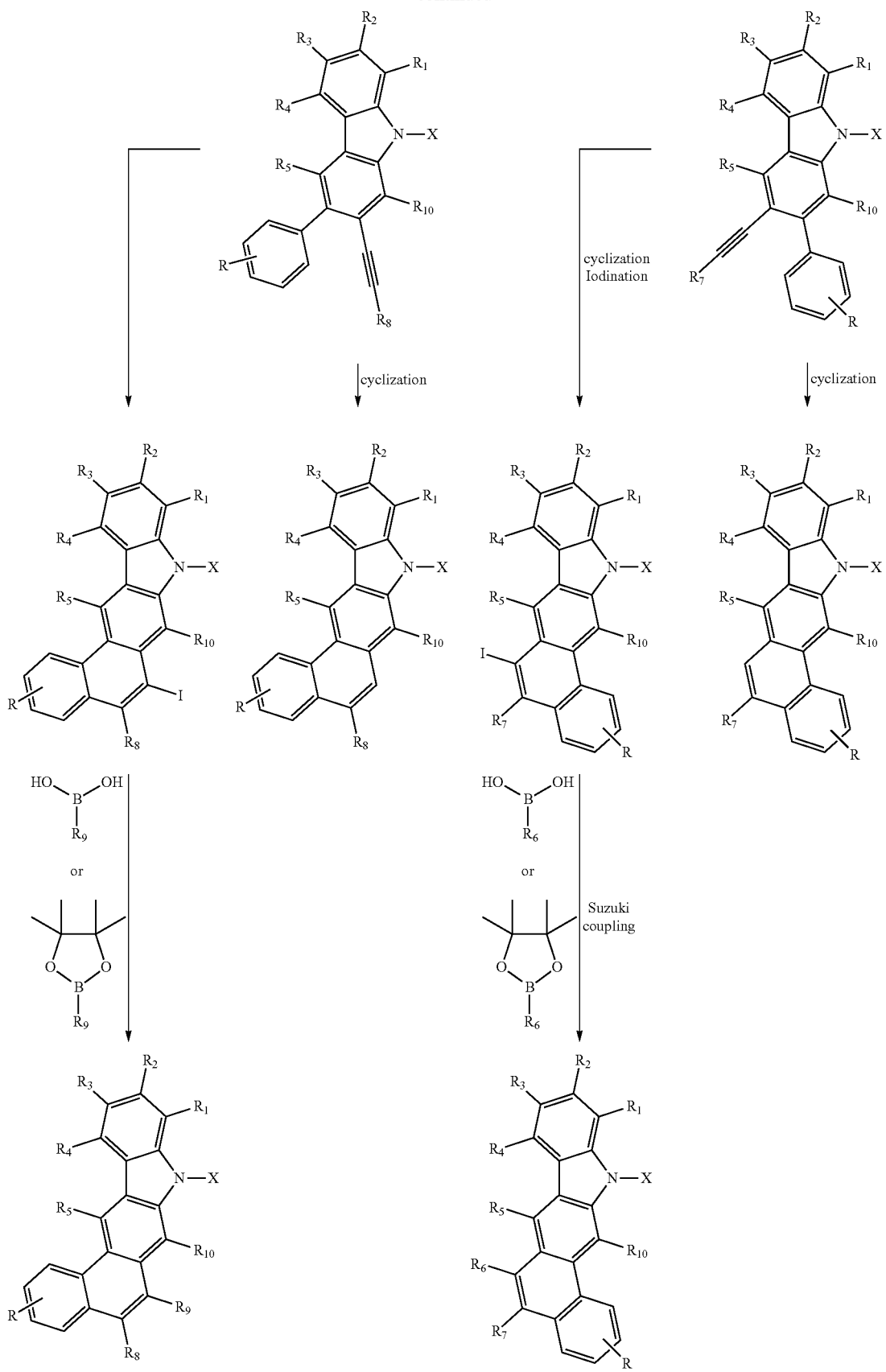

81
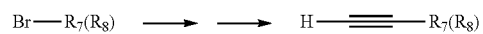
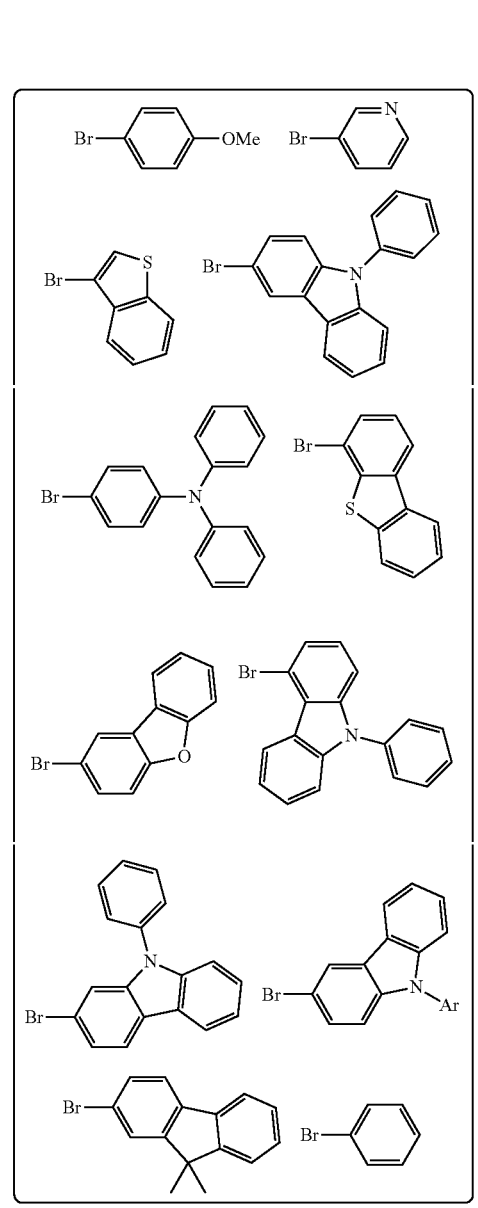
82
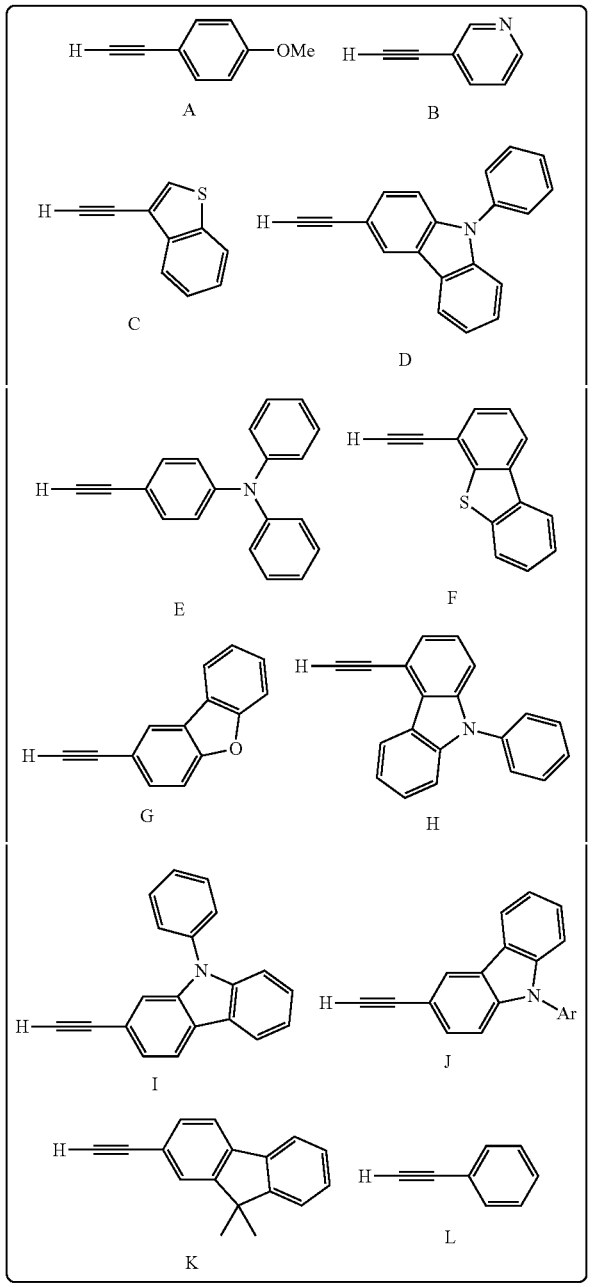
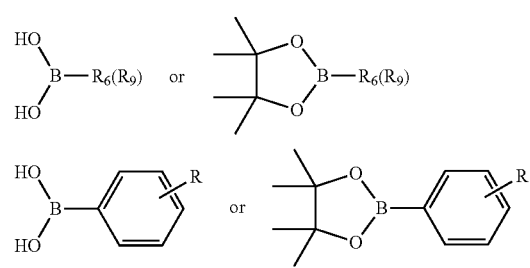

-continued
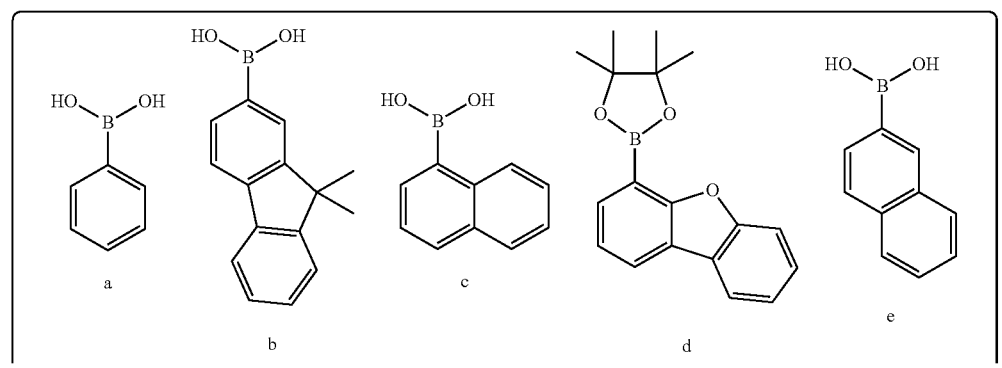
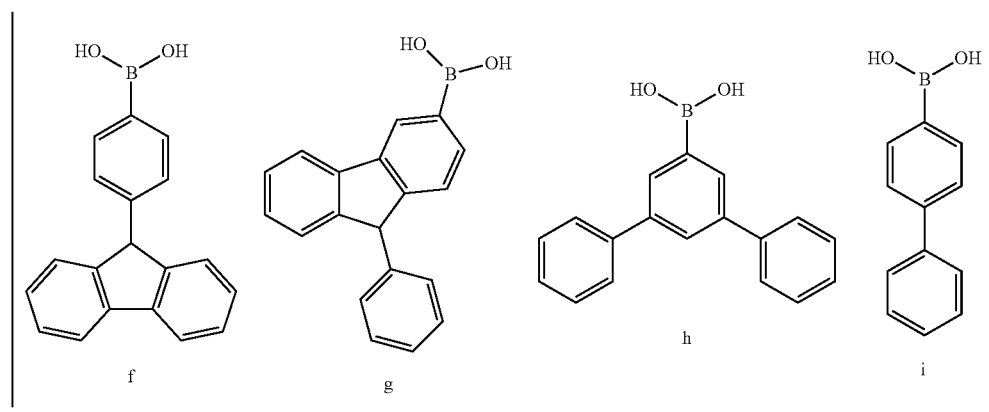
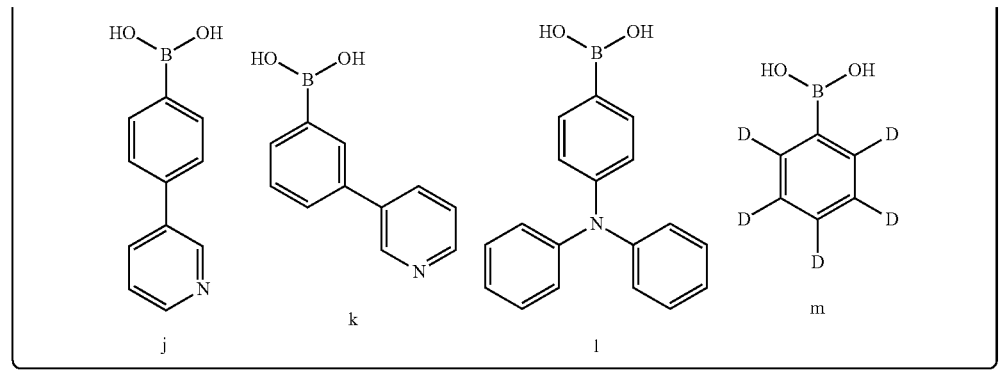

EXAMPLES
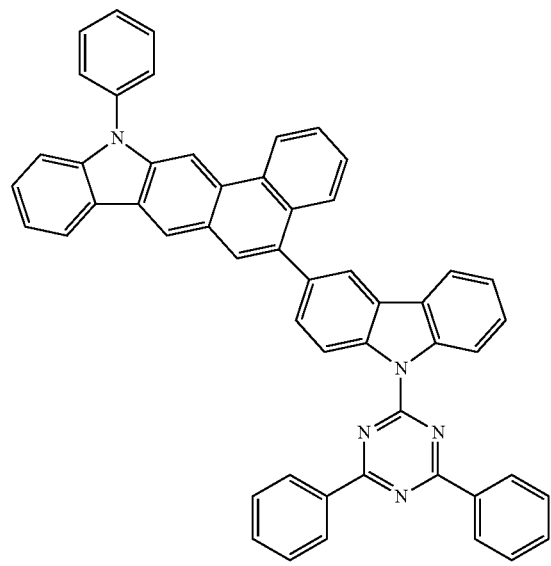
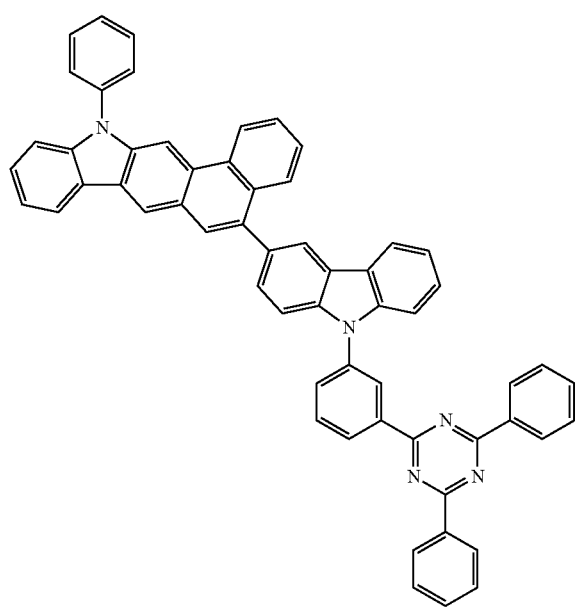
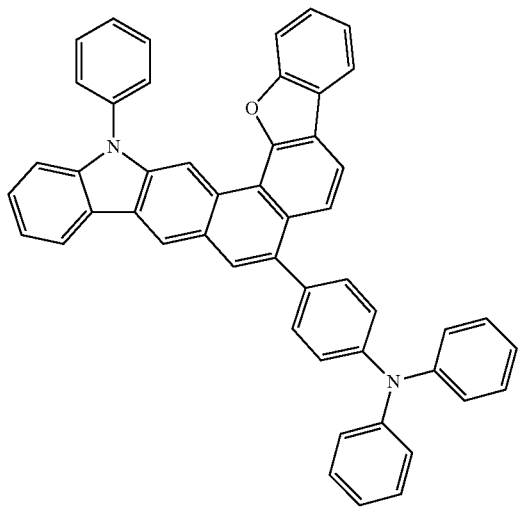

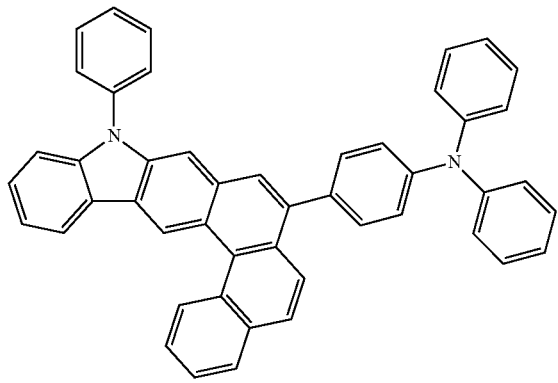

[Synthesis of Intermediate D]

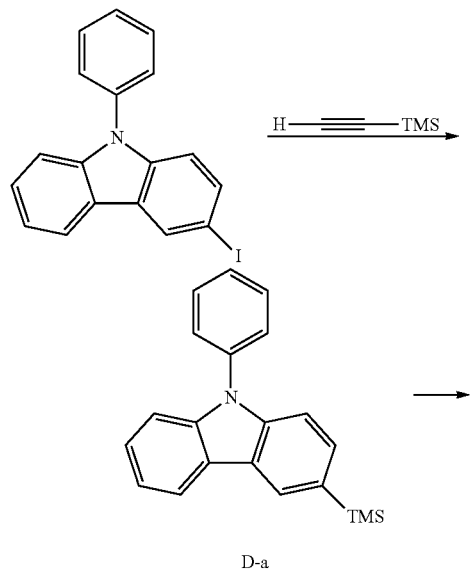

D-a

D

Reaction Example 1: Synthesis of Intermediate D-a 22 g of 3-Iodo-9-phenyl-9H-carbazole, 2.8 g (0.04 eq) of Pd(PPh$_3$)$_4$, and 914 mg (0.08 eq) of CuI were put into a flask, which was then supplied with N2 gas in a vacuum. After 200 mL of tetrahydrofuran (THF) was added into the flask and then stirred, 10 mL (1.2 eq) of triethylamine and 10.0 g (1.2 eq) of TMS-acetylene were slowly dropwise added thereinto, and then stirred at room temperature for about 2 hours in a N2 atmosphere. After removing the solvent using a rotary evaporator, the resulting reaction product was extracted two times each with 200 mL of Et2O and 150 mL of water. An organic layer was collected and dried using magnesium sulfate to evaporate the solvent. The residue was separated and purified by silica gel column chromatography to obtain 20 g of Intermediate D-a (Yield: 99%) This compound was identified using liquid chromatography-mass spectroscopy (LC-MS). C23H21N1Si1: M+339.14

Reaction Example 2: Synthesis of Intermediate D 4.2 g of Intermediate D-a was dissolved in 50 mL of THF, and 30 mL (3 eq) of tetrabutylammonium fluoride in THF (1.0M) was dropwise added thereinto and stirred for about 30 minutes. The reaction solution was extracted three times each with 50 mL of ethylether and 50 mL of ethylether. An organic layer was collected and dried using magnesium sulfate to evaporate the solvent. The residue was separated and purified by silica gel column chromatography to obtain 3.5 g of Intermediate D (Yield: 95%) This compound was identified using LC-MS. C20H13N1: M+267.10

[Synthesis of Intermediates A to L]

Intermediates A to L were synthesized in the same manner as in Reaction Examples 1 and 2 using the same equivalents of reactants.

| Intermediate | Yield (%) Reaction Example 1 | Reaction Example 2 | LC-MS |
|---|---|---|---|
| A | 98 | 95 | 132.06 |
| B | 97 | 94 | 132.04 |
| C | 98 | 96 | 158.02 |
| D | 99 | 95 | 267.10 |
| E | 98 | 97 | 269.12 |
| F | 99 | 96 | 208.03 |
| G | 97 | 97 | 192.06 |
| H | 95 | 93 | 267.10 |
| I | 96 | 96 | 267.10 |
| J(Ar = J1) | 94 | 97 | 421.16 |
| J(Ar = J2) | 95 | 95 | 422.15 |
| J(Ar = J3) | 93 | 93 | 395.14 |
| J(Ar = J4) | 95 | 93 | 419.17 |
| J(Ar = J5) | 96 | 96 | 498.18 |
| K | 94 | 94 | 218.11 |
| L | 92 | 93 | 102.05 |

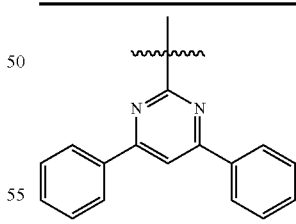

J1

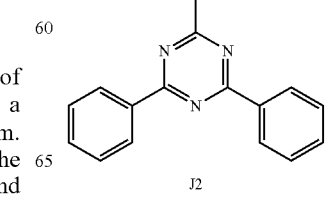

J2

-continued
| Intermediate | Reaction Example 1 | Reaction Example 2 | LC-MS |
|---|---|---|---|
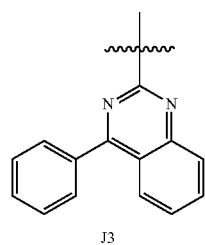 [SMILES: *c1nc(-c2ccccc2)c2ccccc2n1]
J3
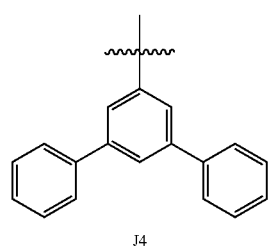 [SMILES: *c1cc(-c2ccccc2)cc(-c2ccccc2)c1]
J4
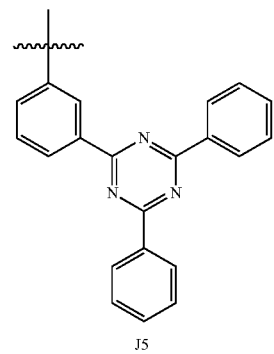 [SMILES: *c1cccc(-c2nc(-c3ccccc3)nc(-c3ccccc3)n2)c1]
J5
Representative Synthesis Example 1
Synthesis of Compound 1
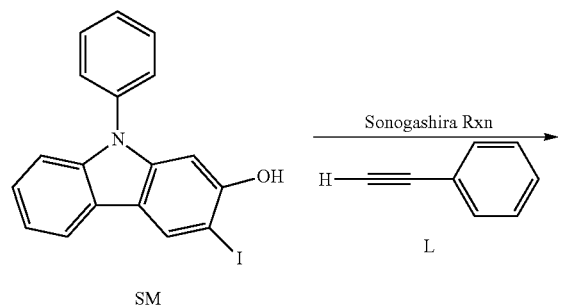
SM
-continued
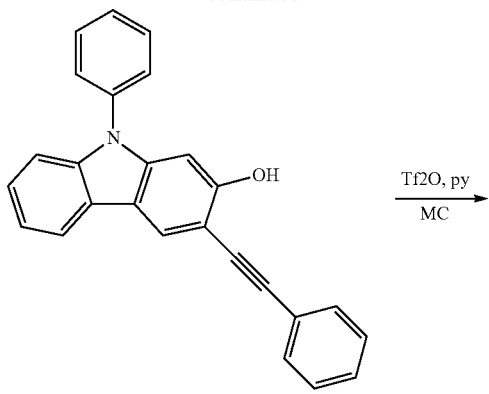
1-a
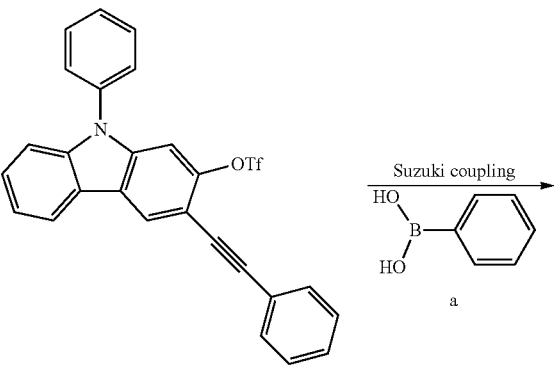
1-b
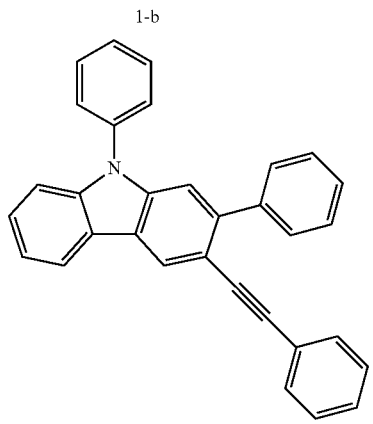
1-c
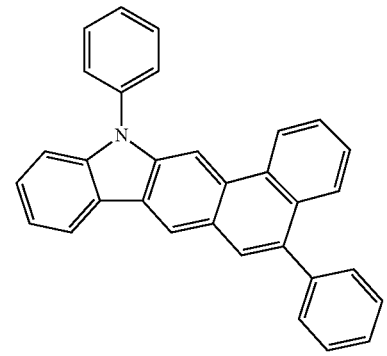
1

Reaction Example 3: Synthesis of Intermediate 1-a 13.6 g (1.2 eq) of 3-Iodo-9-phenyl-9H-carbazol-2-ol (SM), 1.36 g (0.04 eq) of Pd(PPh$_3$)$_4$, and 450 mg (0.08 eq) of CuI were put into a flask, which was then supplied with N$_2$ gas in a vacuum. After 200 mL of tetrahydrofuran (THF) was added into the flask and then stirred. 2.2 mL (1.2 eq) of triethylamine and 3 g (1 eq) of Intermediate L were slowly dropwise added thereinto, and then stirred at room temperature for about 2 hours in N2 atmosphere After removing the solvent using a rotary evaporator, the reaction solution was added with 100 mL of water, and then extracted three times with 100 mL of ethylether. An organic layer was collected and dried using magnesium sulfate to evaporate the solvent. The residue was separated and purified using silica gel column chromatography to obtain 7.74 g of Intermediate 1-a (Yield: 61%). This compound was identified using LC-MS. C$_{26}$H$_{17}$N$_1$O$_1$: M+359.13

Reaction Example 4: Synthesis of Intermediate 1-b 5 g of Intermediate 1-a was dissolved in 100 mL of methylene chloride (MC) to obtain a solution, which was cooled to about 0° C., followed by an addition of 7.84 g of Tf$_2$O and 2 mL of pyridine, and stirring at 0° C. for about 1 hour. After a temperature increase to room temperature, the reaction solution was extracted three times with 100 mL of water and 100 mL of MC. An organic layer was collected and dried using magnesium sulfate to evaporate the solvent. The residue was separated and purified using silica gel column chromatography to obtain 5.48 g of Intermediate 1-b (Yield: 94%). This compound was identified using LC-MS. C27H$_{16}$F$_3$N$_1$O$_3$S$_1$: M+491.08

Reaction Example 5: Synthesis of Intermediate 1-c 5 g of Intermediate 1-b, 1.5 g (1.2 eq) of Compound a, 590 mg (0.05 eq) of Pd(PPh$_3$)$_4$, and 7.0 g (5 eq) of K2CO3 were dissolved in 100 mL of THF and 30 mL of distilled water to obtain a mixed solution, which was stirred for about 24 hours under reflux after a temperature increase to about 120° C. The reaction solution was cooled to room temperature, and then extracted three times with 200 mL of water and 200 mL of diethylether. An organic layer was collected and dried using magnesium sulfate to evaporate the solvent. The residue was separated and purified using silica gel column chromatography to obtain 3.24 g of Intermediate 1-c (Yield: 76%). This compound was identified using LC-MS. C$_{32}$H$_{21}$N$_1$: M+419.17

Reaction Example 6: Synthesis of Compound 1

3.14 g of Intermediate 1-c was dissolved in 50 mL of methylene chloride (MC), and 12.5 mL (20 eq) of trifluoroacetic acid was slowly dropwise added thereinto and stirred at room temperature for about 1 hour. After completion of the reaction, the reaction solution was extracted three times each with 100 mL of water and 100 mL of diethylether. An organic layer was collected and dried using magnesium sulfate to evaporate the solvent. The residue was separated and purified using silica gel column chromatography to obtain 2.7 g of Compound 1 (Yield: 90%). This compound was identified using LC-MS. C$_{32}$H$_{21}$N$_1$: M+419.17

1H NMR (CDCl$_3$, 400 MHz) δ (ppm) 8.93 (s, 2H), 8.12 (s, 2H), 7.93-7.88 (t, 2H), 7.82 (t, 1H), 7.55-7.40 (m, 4H), 7.32-7.22 (m, 8H), 7.08-7.00 (m, 2H)

[Synthesis of Compounds 2 to 31]

A total of 30 compounds were synthesized in the same manner as in Reaction Schemes 3 to 6 in the above-described Representative Synthesis Example 1 using the same equivalents of reactants.

| Compound | Yield (%) | | | | LC-MS |
|---|---|---|---|---|---|
| | Reaction Example 3 | Reaction Example 4 | Reaction Example 5 | Reaction Example 6 | |
| 2 | 66 | 92 | 71 | 91 | 584.23 |
| 3 | 62 | 91 | 76 | 93 | 584.23 |
| 4 | 64 | 93 | 71 | 93 | 584.23 |
| 5 | 64 | 94 | 72 | 90 | 535.23 |
| 6 | 65 | 92 | 75 | 89 | 738.28 |
| 7 | 63 | 93 | 74 | 92 | 739.27 |
| 8 | 65 | 93 | 76 | 93 | 738.28 |
| 9 | 60 | 92 | 69 | 97 | 739.27 |
| 10 | 59 | 91 | 77 | 89 | 736.29 |
| 11 | 64 | 90 | 71 | 94 | 660.26 |
| 12 | 67 | 89 | 73 | 94 | 815.30 |
| 13 | 66 | 93 | 75 | 93 | 712.26 |
| 14 | 62 | 94 | 74 | 94 | 712.26 |
| 15 | 60 | 95 | 75 | 95 | 754.28 |
| 16 | 61 | 92 | 72 | 95 | 815.30 |
| 17 | 68 | 91 | 72 | 88 | 449.18 |
| 18 | 70 | 94 | 75 | 92 | 536.23 |
| 19 | 57 | 90 | 67 | 93 | 634.24 |
| 20 | 68 | 91 | 78 | 97 | 676.25 |
| 21 | 64 | 93 | 76 | 89 | 559.19 |
| 22 | 67 | 96 | 70 | 92 | 614.24 |
| 23 | 61 | 95 | 76 | 91 | 585.22 |
| 24 | 60 | 91 | 78 | 93 | 627.20 |
| 25 | 64 | 90 | 71 | 94 | 660.26 |
| 26 | 63 | 91 | 70 | 91 | 663.27 |
| 27 | 68 | 93 | 72 | 90 | 602.18 |
| 28 | 67 | 94 | 74 | 97 | 676.25 |
| 29 | 64 | 93 | 76 | 96 | 700.29 |
| 30 | 62 | 95 | 75 | 94 | 559.19 |
| 31 | 60 | 93 | 74 | 93 | 585.22 |

$^1$H NMR (CDCl$_3$, 400 MHz) data

| Compound | NMR data |
|---|---|
| 2 | 8.93 (d, 2H), 8.12 (d, 2H), 7.93-7.82 (m, 3H), 7.55 (d, 2H), 7.40-7.36 (m, 3H), 7.30-7.22 (m, 6H), 7.14 (t, 1H), 7.08 (m, 2H), 7.00 (m, 2H) |
| 3 | 8.93 (d, 2H), 8.12 (d, 2H), 7.93-7.88 (m, 2H), 7.82 (t, 1H), 7.77 (s, 1H), 7.55 (d, 2H), 7.46-7.40 (m, 3H), 7.30-7.28 (m, 11H), 7.08-7.00 (m, 4H) |
| 4 | 8.93 (d, 2H), 8.12 (d, 2H), 7.93-7.88 (m, 2H), 7.82 (t, 1H), 7.62-7.61 (t, 2H), 7.55 (d, 2H), 7.40 (d, 2H), 7.30-7.22 (m, 11H), 7.08-7.00 (m, 4H) |
| 5 | 8.93 (d, 2H), 8.12 (d, 2H), 7.93-7.77 (m, 6H), 7.60-7.55 (m, 3H), 7.40-7.38 (m, 2H), 7.30-7.28 (m, 6H), 7.08-7.00 (m, 2H), 1.67 (s, 6H) |
| 6 | 8.93 (d, 2H), 8.12 (d, 2H), 7.93-7.88 (m, 2H), 7.82-7.77 (m, 2H), 7.70 (s, 1H), 7.55 (d, 2H), 7.48-7.46 (m, 5H), 7.40 (d, 2H), 7.32-7.30 (m, 10H), 7.22 (t, 2H), 7.08 (t, 2H), 7.00 (t, 2H) |
| 7 | 8.93 (d, 2H), 7.12 (d, 2H), 7.93-7.88 (m, 2H), 7.82-7.77 (m, 2H), 7.55 (d, 2H), 7.48-7.46 (m, 5H), 7.40 (d, 2H), 7.32-7.22 (m, 12H), 7.08-7.00 (m, 4H) |

-continued

| Compound | NMR data |
|---|---|
| 8 | 8.93 (d, 2H), 8.12 (d, 2H), 7.93-7.88 (m, 2H), 7.82-7.77 (m, 2H), 7.70 (s, 1H), 7.55 (d, 2H), 7.48-7.46 (m, 5H), 7.40 (d, 2H), 7.32-7.22 (m, 12H), 7.08-7.00 (m, 4H) |
| 9 | 8.93 (d, 2H), 8.12 (d, 2H), 7.93-7.88 (m, 2H), 7.82-7.77 (m, 2H), 7.55 (d, 2H), 7.48-7.46 (m, 5H), 7.40 (d, 2H), 7.32-7.22 (m, 12H), 7.08-7.00 (m, 4H) |
| 10 | 8.93 (d, 2H), 8.12 (d, 2H), 7.93-7.88 (m, 2H), 7.82-7.70 (m, 3H), 7.55 (d, 2H), 7.48-7.40 (m, 9H), 7.32-7.22 (m, 12H), 7.08-7.00 (m, 4H) |
| 11 | 8.93 (d, 2H), 8.12 (d, 2H), 7.93-7.88 (m, 2H), 7.82-7.77 (m, 2H), 7.55 (d, 2H), 7.50-7.46 (m, 5H), 7.40 (d, 2H), 7.30-7.22 (m, 11H), 7.08-7.00 (m, 4H) |
| 12 | 8.93 (d, 2H), 8.12 (d, 2H), 7.93-7.88 (m, 2H), 7.82-7.77 (m, 2H), 7.55 (d, 2H), 7.50-7.46 (m, 7H), 7.40 (d, 2H), 7.32-7.22 (m, 14H), 7.08-7.00 (m, 4H) |
| 13 | 8.93 (d, 2H), 8.12 (d, 2H), 8.00 (d, 1H), 7.93 (s, 1H), 7.88-7.77 (m, 5H), 7.60-7.55 (m, 3H), 7.48-7.46 (m, 3H), 7.40 (d, 2H), 7.32-7.30 (m, 3H), 7.30-7.22 (m, 6H), 7.08-7.00 (m, 4H) |
| 14 | 8.93 (d, 2H), 8.12 (d, 2H), 8.00 (d, 1H), 7.93 (s, 1H), 7.88-7.77 (m, 5H), 7.60-7.55 (m, 3H), 7.48-7.46 (m, 3H), 7.40 (d, 2H), 7.32-7.22 (m, 9H), 7.08-7.00 (m, 4H) |
| 15 | 8.93 (d, 2H), 8.12 (d, 2H), 7.93-7.88 (m, 2H), 7.82-7.70 (m, 3H), 7.55-7.22 (m, 20H), 7.08 (m, 2H), 7.08-7.00 (m, 4H) |
| 16 | 8.93 (d, 2H), 8.12 (d, 2H), 8.93-8.77 (m, 4H), 7.55 (d, 2H), 7.55-7.46 (m, 9H), 7.32-7.22 (m, 14H), 7.08-7.00 (m, 4H) |
| 17 | 8.93 (d, 2H), 8.12 (d, 2H), 7.93-7.82 (m, 3H), 7.55 (d, 1H), 7.40-7.37 (m, 3H), 7.30 (m, 5H), 7.08-7.00 (m, 2H), 6.83 (d, 2H), 6.83 (s, 3H) |
| 18 | 8.93-8.81 (t, 3H), 8.55 (d, 1H), 8.26 (s, 1H), 8.12 (s, 1H), 8.06 (d, 1H), 7.97 (d, 1H), 7.93 (s, 1H), 7.61 (d, 1H), 7.55 (d, 1H), 7.44-7.40 (m, 3H), 7.30-7.24 (m, 6H), 7.08-7.00 (m, 2H), 1.73 (s, 6H) |
| 19 | 8.93 (d, 2H), 8.12 (m, 3H), 7.93-7.82 (m, 4H), 7.77 (s, 1H), 7.55 (d, 2H), 7.46 (d, 1H), 7.40 (d, 2H), 7.30 (m, 11H), 7.08-7.00 (m, 4H) |
| 20 | 8.93 (s, 1H), 8.12 (s, 2H), 7.93 (s, 1H), 7.82 (d, 1H), 7.55-7.49 (m, 2H), 7.42-7.40 (m, 2H), 7.30-7.00 (m, 15H), 6.62 (t, 2H), 6.52 (d, 2H), 6.46 (d, 4H) |
| 21 | 8.93 (s, 1H), 8.31 (s, 2H), 8.12 (s, 1H), 7.91 (d, 2H), 7.64-7.61 (d, 2H), 7.55 (d, 2H), 7.49 (d, 1H), 7.42-7.35 (m, 5H), 7.30 (m, 5H), 7.13 (m, 2H), 7.08-7.00 (m, 2H) |
| 22 | 8.90 (m, 2H), 8.10 (s, 2H), 7.90 (m, 2H), 7.55 (m, 3H), 7.40-7.37 (m, 5H), 7.30 (m, 5H), 7.08-7.00 (m, 6H), 6.83 (d, 2H), 3.73 (s, 3H) |
| 23 | 8.93 (s, 2H), 8.81 (s, 1H), 8.55 (d, 1H), 8.12 (s, 2H), 7.97-7.93 (m, 2H), 7.55 (m, 2H), 7.44-7.40 (m, 3H), 7.30 (m, 0H), 7.08-7.00 (m, 4H) |
| 24 | 9.11 (s, 1H), 8.93 (s, 1H), 8.26 (s, 1H), 8.12 (s, 1H), 7.93 (s, 1H), 7.90 (d, 1H), 7.80 (d, 1H), 7.65 (d, 1H), 7.48-7.40 (m, 6H), 7.32-7.22 (m, 13H), 7.08-7.00 (m, 2H) |
| 25 | 8.99-8.93 (m, 2H), 8.34 (s, 1H), 8.12-8.10 (m, 2H), 7.93 (s, 1H), 7.77 (s, 1H), 7.55 (d, 1H), 7.48-7.46 (m, 3H), 7.40 (d, 2H), 7.32-7.30 (m, 3H), 7.30-7.22 (m, 12H), 7.08-7.00 (m, 4H) |
| 26 | 8.99-8.93 (m, 2H), 8.81 (s, 1H), 7.55 (d, 1H), 8.34 (s, 1H), 8.12-8.10 (t, 2H), 7.97-7.93 (t, 2H), 7.55 (d, 1H), 7.44-7.40 (m, 2H), 7.30-7.23 (m, 7H), 7.08-7.00 (m, 6H), 6.62 (t, 2H), 6.52 (d, 2H), 6.46 (d, 4H) |
| 27 | 9.15 (s, 1H), 8.93 (s, 1H), 8.81 (s, 1H), 8.55 (d, 1H), 8.18-7.74 (m, 8H), 7.55-7.53 (m, 2H), 7.44-7.30 (m, 10H), 7.08-7.00 (m, 2H) |
| 28 | 8.93 (s, 1H), 8.68 (d, 1H), 8.12 (s, 1H), 7.93 (s, 1H), 7.64 (s, 1H), 7.55-7.00 (d, 21H), 6.62 (t, 2H), 6.46 (d, 4H) |
| 29 | 8.93 (s, 1H), 8.81 (d, 1H), 8.12 (s, 1H), 8.06-8.02 (m, 2H), 7.93 (s, 1H), 7.77 (s, 1H), 7.61 (d, 1H), 7.55 (d, 2H), 7.46-7.40 (m, 4H), 7.30-7.24 (12H), 7.08-7.00 (m, 4H), 1.80 (s, 6H) |
| 30 | 8.93 (d, 3H), 8.12 (d, 2H), 7.93 (s, 1H), 7.88-7.82 (m, 3H), 7.64 (s, 1H), 7.55 (d, 2H), 7.49 (d, 1H), 7.42-7.40 (m, 2H), 7.35 (d, 1H), 7.30 (m, 5H), 7.19-7.00 (m, 4H) |
| 31 | 8.93 (t, 2H), 8.81 (s, 1H), 8.55 (d, 1H), 8.12 (s, 1H), 7.97-7.88 (m, 3H), 8.55 (d, 2H), 7.44 (d, 1H), 7.40 (d, 2H), 7.30 (m, 10H), 7.08-7.00 (m, 4H) |

Representative Synthesis Example 2
Synthesis of Compound 45
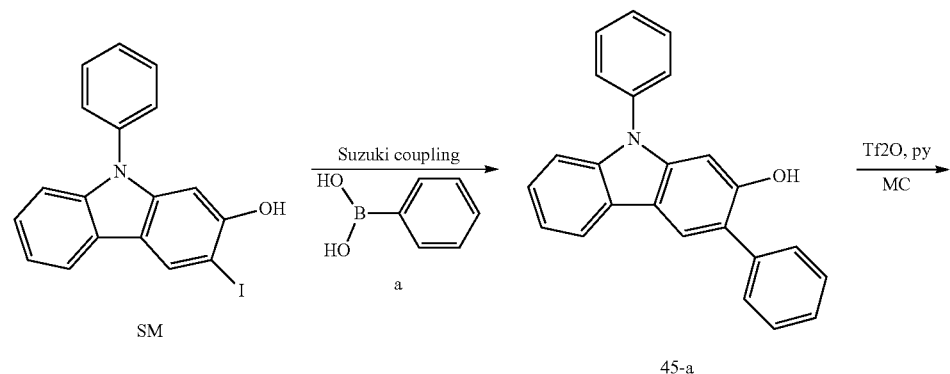
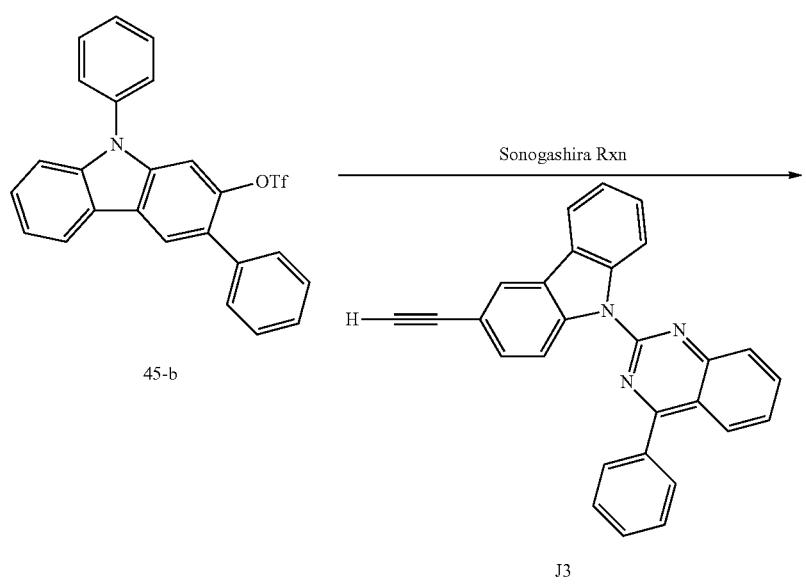
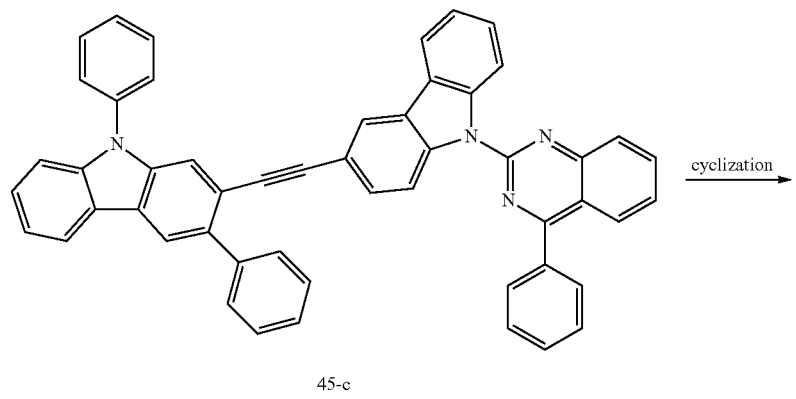

-continued

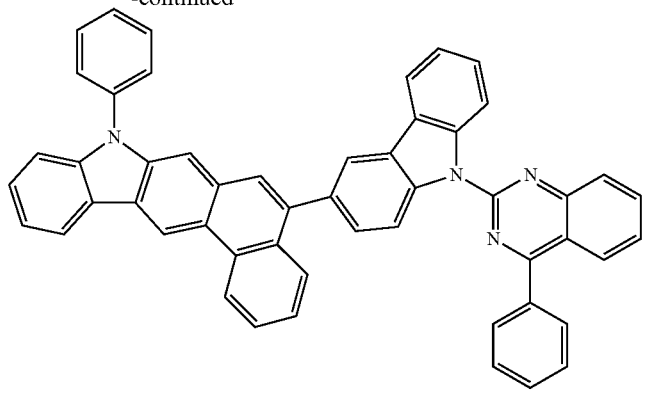

45

Reaction Example 7: Synthesis of Intermediate 45-a 10 g of 3-Iodo-9-phenyl-9H-carbazol-2-ol (SM), 3.8 g (1.2 eq) of Compound a, 1.5 mg (0.05 eq) of Pd(PPh$_3$)$_4$, and 18 g (5 eq) of K$_2$CO$_3$ were dissolved in 200 mL of THF and 60 mL of distilled water to obtain a mixed solution, which was then refluxed for about 24 hours while being stirred after a temperature increase to about 120° C. The reaction solution was cooled to room temperature, and then extracted three times with 200 mL of water and 200 mL of diethylether. An organic layer was collected and dried using magnesium sulfate to evaporate the solvent. The residue was separated and purified using silica gel column chromatography to obtain 8.2 g of Intermediate 45-a (Yield: 74%). This compound was identified using LC-MS. C$_{24}$H$_{17}$N$_1$O$_1$: M+335.13

Reaction Example 8: Synthesis of Intermediate 45-b 5 g of Intermediate 45-a was dissolved in 100 mL of MC to obtain a solution, which was cooled to about 0° C., followed by an addition of 8.4 g of Tf$_2$O and 2 mL of pyridine, and stirring at 0° C. for about 1 hour. After a temperature increase to room temperature, the reaction solution was extracted three times with 100 mL of water and 100 mL of MC. An organic layer was collected and dried using magnesium sulfate to evaporate the solvent. The residue was separated and purified using silica gel column chromatography to obtain 6.69 g of Intermediate 45-b (Yield: 96%). This compound was identified using LC-MS. C$_{25}$H$_{16}$F$_3$N$_1$O$_3$S$_1$: M+467.08

Reaction Example 9: Synthesis of Intermediate 45-c 5.67 g (1.2 eq) of Intermediate 45-b, 470 g (0.04 eq) of Pd(PPh$_3$)$_4$, and 160 mg (0.08 eq) of CuI were put into a flask, which was then supplied with N$_2$ gas in a vacuum. After 200 mL of tetrahydrofuran (THF) was added into the flask and then stirred, 0.9 mL (1.2 eq) of triethylamine and 4 g (1 eq) of Intermediate J3 were slowly dropwise added thereinto, and then stirred at room temperature for about 2 hours in N2 atmosphere. After removing the solvent using a rotary evaporator, the reaction solution was added with 100 mL of water, and then extracted three times with 100 mL of ethylether. An organic layer was collected and dried using magnesium sulfate to evaporate the solvent. The residue was separated and purified using silica gel column chromatography to obtain 5.1 g of Intermediate 45-c (Yield: 58%). This compound was identified using LC-MS. C52H$_{32}$N$_4$: M+712.26

Reaction Example 10: Synthesis of Compound 45

3 g of Intermediate 45-c was dissolved in 50 mL of methylene chloride (MC), and 7.4 mL (20 eq) of trifluoroacetic acid was slowly dropwise added thereinto and stirred at room temperature for about 1 hour. After completion of the reaction, the reaction solution was extracted three times each with 100 mL of water and 100 mL of diethylether. An organic layer was collected and was dried using magnesium sulfate to evaporate the solvent. The residue was separated and purified using silica gel column chromatography to obtain 2.76 g of Compound 45 (Yield: 92%). This compound was identified using LC-MS. C$_{52}$H$_{32}$N$_4$: M+712.26

1H NMR (CDCl3, 400 MHz) δ (ppm) 8.93 (s, 2H), 8.12 (s, 2H), 8.0 (d, 1H), 7.93-7.77 (m, 6H), 7.60-7.22 (m, 17H), 7.08 (m, 2H), 7.00 (m, 2H)

Synthesis of Compounds 32 to 44, and 46 to 64

A total of 32 compounds were synthesized in the same manner as in Reaction Schemes 7 to 10 in the above-described Representative Synthesis Example 2 using the same equivalents of reactants.

| Compound | Yield (%) | | | | LC-MS |
| | Reaction Example 7 | Reaction Example 8 | Reaction Example 9 | Reaction Example 10 | |
| --- | --- | --- | --- | --- | --- |
| 32 | 72 | 90 | 59 | 90 | 419.17 |
| 33 | 70 | 92 | 61 | 91 | 584.23 |
| 34 | 72 | 92 | 63 | 92 | 584.23 |
| 35 | 73 | 91 | 67 | 90 | 584.23 |
| 36 | 76 | 90 | 62 | 96 | 535.23 |
| 37 | 71 | 89 | 63 | 94 | 538.28 |
| 38 | 76 | 93 | 67 | 92 | 739.27 |
| 39 | 72 | 92 | 62 | 92 | 738.28 |
| 40 | 74 | 93 | 69 | 91 | 739.27 |
| 41 | 71 | 91 | 62 | 89 | 736.29 |
| 42 | 69 | 90 | 72 | 92 | 660.26 |
| 43 | 73 | 93 | 67 | 93 | 815.30 |
| 44 | 71 | 89 | 59 | 90 | 712.26 |

Yield (%)

| Compound | Reaction Example 7 | Reaction Example 8 | Reaction Example 9 | Reaction Example 10 | LC-MS |
|---|---|---|---|---|---|
| 46 | 72 | 88 | 62 | 88 | 754.28 |
| 47 | 76 | 91 | 61 | 93 | 815.30 |
| 48 | 78 | 93 | 70 | 97 | 449.18 |
| 49 | 74 | 90 | 68 | 96 | 420.16 |
| 50 | 72 | 91 | 62 | 91 | 591.20 |
| 51 | 70 | 93 | 67 | 91 | 636.26 |
| 52 | 68 | 92 | 63 | 94 | 615.17 |
| 53 | 70 | 87 | 67 | 54 | 499.19 |
| 54 | 70 | 87 | 67 | 46 | 499.19 |
| 55 | 79 | 89 | 61 | 94 | 585.22 |
| 56 | 78 | 92 | 71 | 32 | 640.20 |
| 57 | 78 | 92 | 71 | 68 | 640.20 |
| 58 | 80 | 89 | 64 | 89 | 736.29 |
| 59 | 71 | 93 | 73 | 91 | 662.27 |
| 60 | 72 | 91 | 58 | 90 | 602.18 |
| 61 | 78 | 90 | 62 | 64 | 586.20 |
| 62 | 78 | 90 | 62 | 36 | 586.20 |
| 63 | 69 | 88 | 67 | 94 | 616.25 |
| 64 | 77 | 90 | 69 | 88 | 424.19 |

$^1$H NMR (CDCl$_3$, 400 MHz) data

| Compound | NMR data |
|---|---|
| 32 | 8.93 (s, 2H), 8.12 (d, 2H), 7.93-7.82 (m, 3H), 7.55-7.22 (m, 12H), 7.08-7.00 (m, 2H) |
| 33 | 8.93 (s, 2H), 8.12 (d, 2H), 7.93-7.82 (m, 3H), 7.55 (d, 2H), 7.40-7.00 (m, 19H) |
| 34 | 8.93 (s, 2H), 8.12 (d, 2H), 7.93-7.77 (m, 4H), 7.55 (d, 2H), 7.46-7.30 (m, 14H), 7.08-7.00 (m, 4H) |
| 35 | 8.93 (s, 2H), 8.12 (d, 2H), 7.93-7.82 (m, 3H), 7.61-7.55 (m, 4H), 7.40 (d, 2H), 7.30-7.22 (m, 11H), 7.08-7.00 (m, 4H) |
| 36 | 8.93 (s, 2H), 8.12 (d, 2H), 7.90-7.77 (m, 6H), 7.60-7.55 (m, 3H), 7.40-7.38 (m, 2H), 7.30-7.28 (m, 6H), 7.08-7.00 (m, 2H), 1.67 (s, 6H) |
| 37 | 8.93 (s, 2H), 8.12 (d, 2H), 7.93-7.77 (m, 4H), 7.70 (s, 1H), 7.55-7.22 (m, 21H), 7.08-7.00 (m, 4H) |
| 38 | 8.93 (s, 2H), 8.12 (d, 2H), 7.93-7.77 (m, 4H), 7.55-7.22 (m, 21H), 7.08-7.00 (m, 4H) |
| 39 | 8.93 (s, 2H), 8.12 (d, 2H), 7.93-7.77 (m, 4H), 7.70 (s, 1H), 7.55-7.22 (m, 21H), 7.08-7.00 (m, 4H) |
| 40 | 8.93 (s, 2H), 8.12 (d, 2H), 7.93-7.77 (m, 4H), 7.55-7.22 (m, 21H), 7.08-7.00 (m, 4H) |
| 41 | 8.93 (s, 2H), 8.12 (d, 2H), 7.93-7.470 (m, 5H), 7.55-7.22 (m, 23H), 7.08-7.00 (m, 4H) |
| 42 | 8.93 (s, 2H), 8.12 (d, 2H), 7.93-7.77 (m, 4H), 7.55-7.22 (m, 20H), 7.08-7.00 (m, 4H) |
| 43 | 8.93 (s, 2H), 8.12 (d, 2H), 7.93-7.77 (m, 4H), 7.55-7.20 (m, 25H), 7.08-7.00 (m, 4H) |
| 44 | 8.93 (s, 2H), 8.12 (d, 2H), 7.80-7.77 (m, 7H), 7.60-7.22 (m, 17H), 7.08-7.00 (m, 4H) |
| 46 | 8.93 (s, 2H), 8.12 (d, 2H), 7.93-7.88 (t, 2H), 7.82-7.70 (m, 3H), 7.55-7.20 (m, 22H), 7.08 (m, 2H), 7.08-7.00 (m, 4H) |
| 47 | 8.93 (s, 2H), 8.12 (d, 2H), 7.93-7.77 (m, 4H), 7.55-7.20 (m, 26H), 7.08-7.00 (m, 4H) |
| 48 | 8.93 (s, 2H), 8.12 (d, 2H), 7.93-7.82 (m, 3H), 7.55 (d, 1H), 7.40-7.37 (m, 3H), 7.30 (m, 5H), 7.08-7.00 (m, 2H), 6.83 (d, 2H), 3.73 (s, 3H) |
| 49 | 8.93 (s, 2H), 8.81 (s, 1H), 8.55 (d, 1H), 8.12 (d, 2H), 7.97-7.82 (m, 4H), 7.55 (d, 1H), 7.44-7.40 (m, 2H), 7.30 (m, 5H), 7.08-7.00 (m, 2H) |
| 50 | 8.93 (s, 1H), 8.86 (s, 1H), 8.26 (s, 1H), 7.12 (s, 1H), 7.06 (d, 1H), 7.93 (s, 1H), 7.90 (d, 1H), 7.80 (d, 1H), 7.60 (d, 1H), 7.55 (d, 1H), 7.44 (t, 1H), 7.40 (s, 2H), 7.30-7.24 (m, 8H), 7.08-7.00 (m, 2H), 1.73 (s, 6H) |
| 51 | 8.93 (d, 2H), 8.12 (d, 3H), 7.93-7.82 (m, 4H), 7.55 (d, 1H), 7.40 (d, 1H), 7.30-7.23 (m, 7H), 7.08-7.00 (m, 6H), 7.62 (t, 2H), 6.52 (d, 2H), 6.46 (d, 4H) |
| 52 | 8.93 (s, 1H), 8.12 (d, 2H), 7.93 (s, 1H), 7.86-7.74 (m, 4H), 7.55-7.00 (m, 17H) |
| 53 | 8.93 (s, 1H), 8.31 (s, 2H), 8.12 (s, 1H), 7.91 (d, 2H), 7.61-7.55 (m, 2H), 7.40-7.37 (m, 5H), 7.30 (m, 5H), 7.08-7.00 (m, 2H), 6.83 (d, 2H), 3.73 (s, 3H) |
| 54 | 8.93 (d, 3H), 8.12 (d, 2H), 7.93 (s, 1H), 7.88 (d, 2H), 7.82 (t, 1H), 7.55 (d, 1H), 7.40-7.37 (m, 3H), 7.30 (m, 5H), 7.08-7.00 (m, 2H), 6.83 (d, 2H), 3.73 (s, 3H) |
| 55 | 8.90 (d, 2H), 8.81 (s, 1H), 7.55 (d, 1H), 8.10 (s, 2H), 7.97-7.90 (m, 3H), 7.55 (d, 3H), 7.44-7.40 (m, 4H), 7.30 (m, 5H), 7.08-7.00 (m, 6H) |
| 56 | 8.93 (s, 2H), 8.12 (s, 2H), 7.93-7.80 (m, 3H), 7.55 (d, 2H), 7.40 (m, 3H), 7.30 (m, 7H), 7.08-7.00 (m, 4H) |
| 57 | 8.93 (d, 2H), 8.12 (s, 1H), 7.93 (s, 1H), 7.90-7.88 (m, 2H), 7.80 (d, 1H), 7.55 (d, 2H), 7.40 (m, 3H), 7.3 (m, 12H), 7.08-7.00 (m, 4H) |
| 58 | 9.10 (s, 1H), 8.93 (s, 1H), 8.26 (s, 1H), 8.12 (s, 1H), 7.93 (s, 1H), 7.77 (s, 1H), 7.55-7.22 (m, 26H), 7.08-7.00 (m, 4H) |
| 59 | 8.99 (d, 1H), 8.93 (s, 1H), 8.34 (s, 1H), 8.12-8.10 (t, 2H), 7.93 (s, 1H), 7.55 (d, 1H), 7.48-7.40 (m, 3H), 7.32-7.23 (m, 10H), 7.08-7.00 (m, 6H), 6.62 (t, 2H), 6.52-6.46 (6H) |
| 60 | 8.99 (d, 1H), 8.93 (s, 1H), 8.81 (s, 1H), 8.55 (d, 1H), 8.34 (s, 1H), 8.12-8.10 (t, 2H), 7.97-7.93 (t, 2H), 7.80 (d, 1H), 7.78-7.74 (m, 2H), 7.55-7.53 (m, 2H), 7.44-7.30 (m, 10H), 7.08-7.00 (m, 2H) |

-continued

| Compound | NMR data |
|---|---|
| 61 | 9.15 (s, 1H), 8.93 (s, 1H), 8.81 (s, 1H), 8.55 (d, 1H), 8.18-8.12 (t, 2H), 8.04-7.93 (m, 3H), 7.71 (s, 1H), 7.55-7.40 (m, 7H), 7.30-7.00 (m, 9H) |
| 62 | 8.93-8.89 (t, 2H), 8.81 (s, 1H), 8.55 (d, 1H), 8.12 (s, 1H), 8.04-7.93 (m, 4H), 7.71 (s, 1H), 7.55-7.40 (m, 7H), 7.30 (m, 5H), 7.19-7.00 (m, 4H) |
| 63 | 8.93 (s, 1H), 8.68 (s, 1H), 8.12 (s, 1H), 7.93 (s, 1H), 7.55 (d, 1H), 7.40-7.37 (m, 3H), 7.32-7.30 (m, 6H), 7.08 (m, 7H), 6.83 (d, 2H), 6.62 (t, 2H), 6.46 (d, 4H), 3.73 (s, 3H) |
| 64 | 8.90 (s, 1H), 8.81 (s, 1H), 7.55 (d, 1H), 8.10 (s, 1H), 7.97 (d, 1H), 7.90 (s, 1H), 7.55 (d, 1H), 7.44-7.40 (m, 2H), 7.30 (m, 5H), 7.08-7.00 (m, 2H) |

Example 1

A green phosphorescent top-emission device and a red phosphorescent top-emission device were manufactured as follows.

To manufacture an anode, a substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a known HIL material, was vacuum-deposited on the glass substrate to form a HIL having a thickness of about 600 Å. Then, 4,4'-bis[N-(1-naphthyl)-N-phenylamino]biphenyl (NPB), which is a known hole transporting compound, was vacuum-deposited on the HIL to form a HTL having a thickness of about 1000 Å.

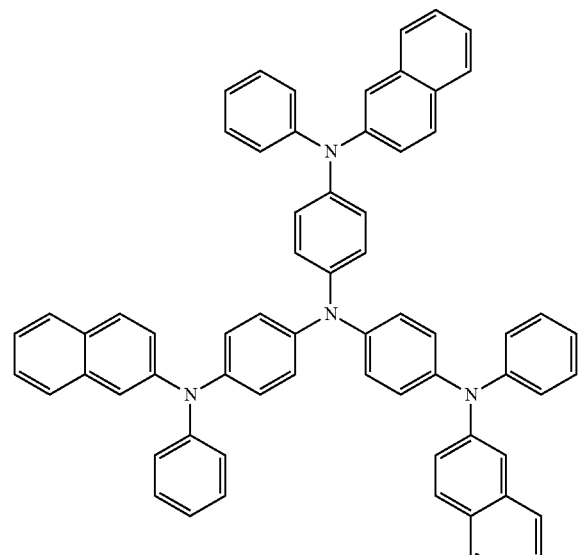

2-TNATA

-continued

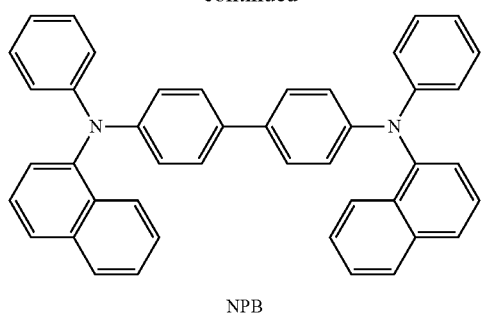

NPB

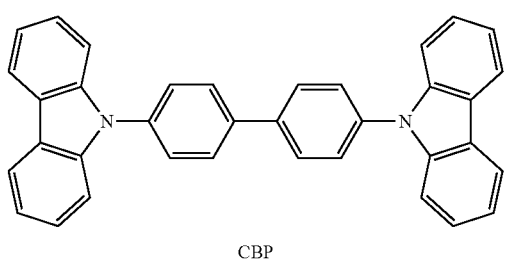

CBP

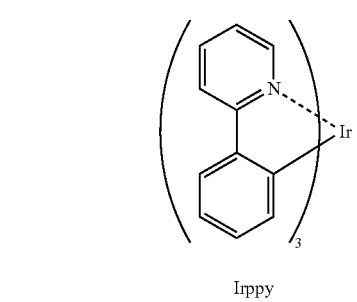

Irppy

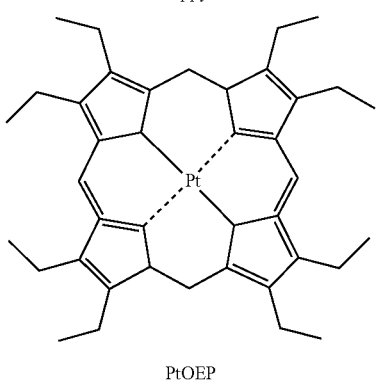

PtOEP

-continued

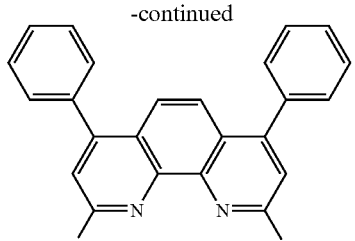

BCP

Then, Compound 9 as a green phosphorescent host and a widely known compound Irppy as a green phosphorescent dopant were co-deposited in a weight ratio of 91:9 on the HTL to form an EML having a thickness of about 250 Å.

Afterward, BCP as a hole blocking compound was vacuum-deposited on the EML to form a HBL having a thickness of about 50 Å. Then, $Alq_3$ was deposited on the EML to form an ETL having a thickness of 350 Å, and then LiF, which is a halogenated alkali metal, was deposited on the ETL to form an EIL having a thickness of 10 Å. Then, Mg and Ag were vacuum-deposited in a weight ratio of 90:10 on the EIL to form a cathode having a thickness of 120 Å, thereby completing the manufacture of an organic light-emitting device.

Example 2

An organic light-emitting device was manufactured in the same manner as in Example 1, except that Compound 16, instead of Compound 9 used as green phosphorescent host in Example 1, was used.

Example 3

An organic light-emitting device was manufactured in the same manner as in Example 1, except that Compound 21, instead of NPB used a material for the HTL in Example 1, was used, and CBP as a green phosphorescent host was used.

Example 4

An organic light-emitting device was manufactured in the same manner as in Example 1, except that Compound 30, instead of NPB used a material for the HTL in Example 1, was used, and CBP as a green phosphorescent host was used.

Example 5

An organic light-emitting device was manufactured in the same manner as in Example 1, except that Compound 51, instead of NPB used as a material for the HTL in Example 1, was used, and CBP as a green phosphorescent host was used.

Example 6

An organic light-emitting device was manufactured as a red phosphorescent top-emission device as follows.

To manufacture an anode, a substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA, which is a known material, was vacuum-deposited on the substrate to form a HIL having a thickness of 600 Å, and NPB as a hole transporting compound was vacuum-deposited on the HIL to form a HTL having a thickness of 1350 Å.

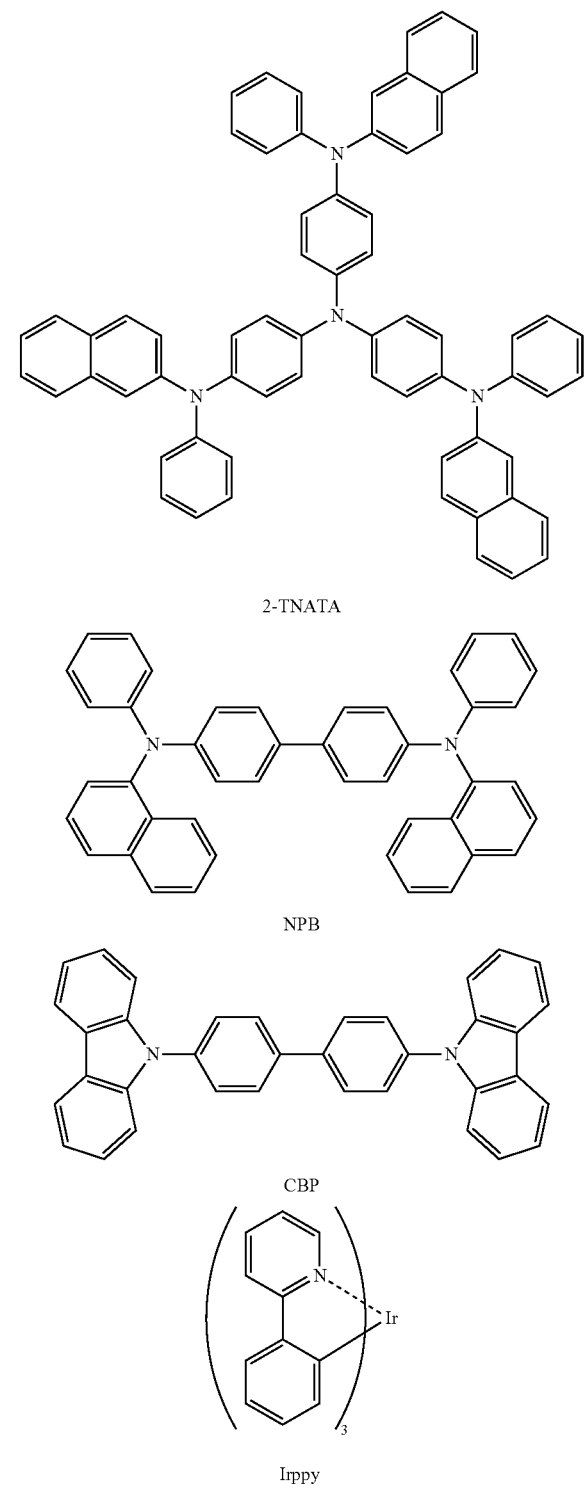

2-TNATA

NPB

CBP

Irppy

-continued

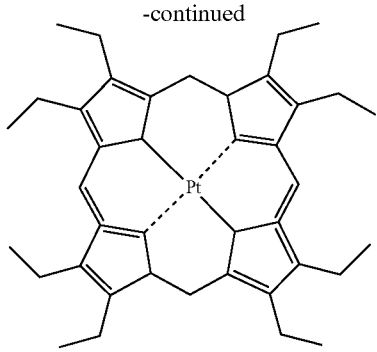

PtOEP

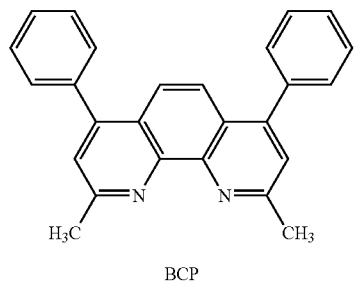 [SMILES: Cc1cc(-c2ccccc2)c2ccc3c(-c4ccccc4)cc(C)nc3c2n1 ; "BCP"]

BCP

Then, Compound 45 as a red phosphorescent host and a widely known compound PtOEP as a red phosphorescent dopant were co-deposited in a weight ratio of 91:9 on the HTL to form an EML having a thickness of about 250 Å.

Afterward, BCP as a hole blocking compound was vacuum-deposited on the EML to form a HBL having a thickness of about 50 Å. Then, $Alq_3$ was deposited on the EML to form an ETL having a thickness of 350 Å, and then LiF, which is a halogenated alkali metal, was deposited on the ETL to form an EIL having a thickness of 10 Å. Then, Mg and Ag were vacuum-deposited in a weight ratio of 90:10 on the EIL to form a cathode having a thickness of 120 Å, thereby completing the manufacture of the organic light-emitting device.

Example 7

An organic light-emitting device was manufactured in the same manner as in Example 1, except that Compound 51, instead of NPB used as a material for the HTL in Example 1, was used, and Compound 16 as a green phosphorescent host was used in forming the EML.

Comparative Example 1

An organic light-emitting device was manufactured as a green phosphorescent top-emission device having the following structure.

MgAg(120, 10%)
LiF(10 Å)
Alq3(350 Å)
BCP(50 Å)
CBP, Irppy(250 Å, 9%)
NPB(1000 Å)
2TNATA(600 Å)
ITO/Ag/ITO
(70/1000/70 Å)

Comparative Example 2

An organic light-emitting device was manufactured as an organic red phosphorescent top-emission device having the following structure.

MgAg(120, 10%)
LiF(10 Å)
Alq3(350 Å)
BCP(50 Å)
CBP, PtOEP(400 Å, 6%)
NPB(1350 Å)
2TNATA(600 Å)
ITO/Ag/ITO
(70/1000/70 Å)

Comparative Example 3

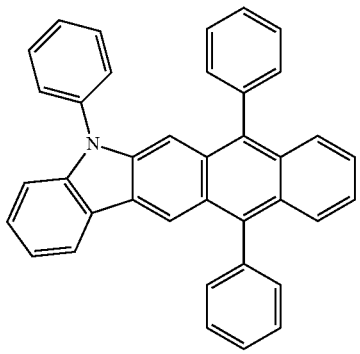

999

An organic light-emitting device was manufactured in the same manner as in Example 1, except that a comparative Compound 999, instead of Compound 9 used as a green phosphorescent host in forming the EML in Example 1, was used.

Comparative Example 4

An organic light-emitting device was manufactured in the same manner as in Example 6, except that a comparative Compound 999, instead of Compound 45 used as a red phosphorescent host in forming the EML in Example 1, was used.

Comparative Example 5

An organic light-emitting device was manufactured in the same manner as in Example 3, except that a comparative Compound 999, instead of Compound 21 used in forming the HTL in Example 3, was used.

The green phosphorescent devices manufactured using the heterocyclic compounds represented by Formula 1 according to an embodiment were found to have lower driving voltages, improved life times, and remarkable improvements in efficiency. The red phosphorescent devices including the heterocyclic compounds of Formula 1 were found to have lower driving voltages, improved efficiency, and remarkable improvements in lifetime I-V-L characteristics of each light-emitting device were evaluated.

The characteristics and lifetimes of the organic light-emitting devices of Examples 1 to 7 and Comparative Examples 1 to 5 are shown in Table 1 below.

TABLE 1

|  | EML or ETL material | Driving voltage (V) | Current density (mA/cm$^2$) | Luminance (cd/m$^2$) | Efficiency (cd/A) | Emission Color | Color coordinates | LT$_{97}$ (hr) |
|---|---|---|---|---|---|---|---|---|
| Example 1 | G phosphorescent host 9 | 5.6 | 10 | 6,342 | 63.4 | Green | 0.25, 0.71 | 73 |
| Example 2 | G phosphorescent host 16 | 5.4 | 10 | 6,571 | 65.7 | Green | 0.26, 0.72 | 75 |
| Example 3 | HTL material 21 | 5.4 | 10 | 6,479 | 64.8 | Green | 0.25, 0.70 | 74 |
| Example 4 | HTL material 30 | 5.5 | 10 | 6,537 | 65.4 | Green | 0.24, 0.72 | 78 |
| Example 5 | HTL material 51 | 5.4 | 10 | 6,610 | 66.1 | Green | 0.25, 0.70 | 73 |
| Example 6 | R phosphorescent host 45 | 7.0 | 10 | 3,079 | 30.8 | Red | 0.66, 0.31 | 127 |
| Example 7 | HTL material 51 G phosphorescent host 16 | 5.3 | 10 | 6,682 | 66.8 | Green | 0.24, 0.71 | 79 |
| Comparative Example 1 | CBP/Irppy | 6.8 | 10 | 4,766 | 47.7 | Green | 0.25, 0.70 | 61 |
| Comparative Example 2 | CBP/porphyrin | 7.3 | 10 | 2,212 | 22.1 | Red | 0.67, 0.32 | 89 |
| Comparative Example 3 | G phosphorescent host 999 | 9.1 | 10 | 1,034 | 10.3 | Green | 0.24, 0.67 | 20 |
| Comparative Example 4 | R phosphorescent host 999 | 9.7 | 10 | 517 | 5.17 | Red | 0.66, 0.32 | 24 |
| Comparative Example 5 | HTL material 999 | 7.0 | 10 | 2,101 | 21.0 | Green | 0.23, 0.70 | 17 |

As described above, according to the one or more embodiments, the novel heterocyclic compound represented by Formula 1 above has improved charge transporting capability, and thus may be used as a hole transporting material and an electron transporting material that are suitable for any color fluorescent and phosphorescent devices, such as red, green, blue, and white fluorescent and phosphorescent devices. Therefore, organic light-emitting devices having low driving voltages and high luminance may be manufactured using the heterocyclic compounds of Formula 1 above. The organic light-emitting devices may also have high efficiencies and long lifetimes.

The embodiments provide a material having improved electrical stability, high charge-transfer or emission capability, and a high glass transition temperature that is high enough to prevent crystallization.

While exemplary embodiments have been described above, it will be understood by those of ordinary skill in the art that various changes in form and details may be made therein without departing from the spirit and scope of the present invention as defined by the following claims.

What is claimed is:

1. A heterocyclic compound represented by Formula 1 below:

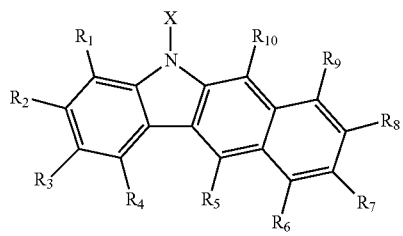

<Formula 1> wherein, in Formula 1, $R_1$ to $R_{10}$ are each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with one or two C6-C60 aryl groups, a substituted or unsubstituted C3-C60 heteroaryl group, or a substituted or unsubstituted C6-C60 condensed polycyclic group;

$R_8$ and $R_9$ are linked to each other to form a benzene ring, a naphthalene ring, or a dibenzofuran ring, or $R_6$ and $R_7$ are linked to each other to form a benzene ring, a naphthalene ring, or a dibenzofuran ring; and X is a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

2. The heterocyclic compound as claimed in claim 1, wherein the heterocyclic compound is represented by Formula 2 below:

<Formula 2>

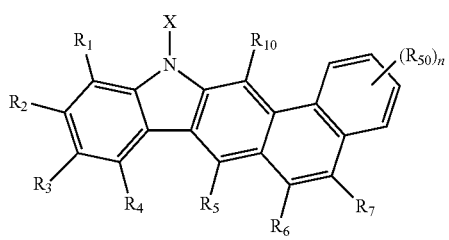

wherein, in Formula 2, $R_1$ to $R_7$, $R_{10}$, and $R_{50}$ are each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with one or two C6-C60 aryl groups, a substituted or unsubstituted C3-C60 heteroaryl group, or a substituted or unsubstituted C6-C60 condensed polycyclic group;

n is an integer from 1 to 4;

when n>1, a plurality of $(R_{50})_n$ moieties are optionally linked to each other to form a ring; and X is a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

3. The heterocyclic compound as claimed in claim 1, wherein $R_7$ in Formula 2 is a group represented by one of Formulae 2a to 2d below:

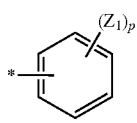
2a

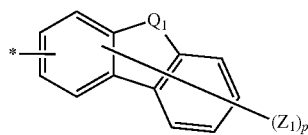
2b

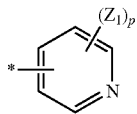
2c

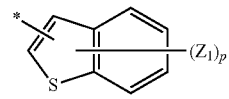
2d wherein, in Formulae 2a to 2d, $Q_1$ is a linker represented by —C($R_{30}$)($R_{31}$)—, —O—, —S—, or —N($R_{32}$)—;

$Z_1$, $R_{30}$, $R_{31}$, and $R_{32}$ are each independently a hydrogen atom, a deuterium atom, a substituted or unsubstituted C1-C20 alkyl group, a substituted or unsubstituted C6-C20 aryl group, an amino group substituted with one or two C6-C20 aryl groups, a substituted or unsubstituted C6-C20 condensed polycyclic group, a halogen group, a cyano group, a nitro group, a hydroxy group, or a carboxy group;

p is an integer from 1 to 7; and

* indicates a binding site of $R_7$ in Formula 2.

4. The heterocyclic compound as claimed in claim 2, wherein X in Formula 2 is a group represented by one of Formulae 3a to 3c below:

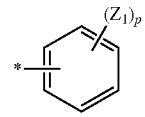
3a

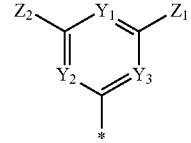
3b

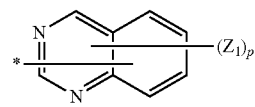
3c wherein, in Formulae 3a to 3c, $Z_1$ and $Z_2$ are each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group, a cyano group, a nitro group, a hydroxyl group, or a carboxy group;

$Y_1$ to $Y_3$ are each independently C or N;

p is an integer from 1 to 5; and

* indicates a binding site of X in Formula 2.

5. The heterocyclic compound as claimed in claim 1, wherein the heterocyclic compound is represented by Formula 3 below:

<Formula 3>

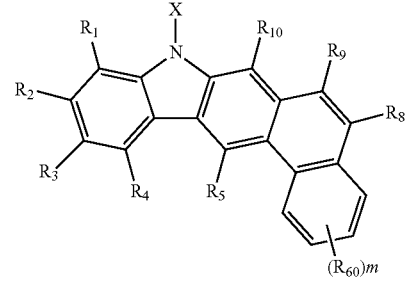

wherein, in Formula 3, $R_1$ to $R_5$, $R_8$ to $R_{10}$, and $R_{60}$ are each independently a hydrogen atom, a deuterium atom, a substituted or unsubstituted C1-C60 alkyl group, a substituted or unsubstituted C1-C60 alkenyl group, a substituted or unsubstituted C6-C60 aryl group, a substituted or unsubstituted C6-C60 aryloxy group, an amino group substituted with one or two C6-C60 aryl groups, a substituted or unsubstituted C3-C60 heteroaryl group, or a substituted or unsubstituted C6-C60 condensed polycyclic group;

m is an integer from 1 to 4;

when m>1, a plurality of $(R_{60})_m$ moieties are optionally linked together to form a ring; and X is a substituted or unsubstituted C1-C60 alkyl group, a substituted or unsubstituted C6-C60 aryl group, a substituted or unsubstituted C4-C60 heteroaryl group, or a substituted or unsubstituted C6-C60 condensed polycyclic group.

6. The heterocyclic compound as claimed in claim 5, wherein $R_8$ in Formula 3 is a group represented by one of Formulae 2a to 2d below:

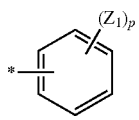

2a

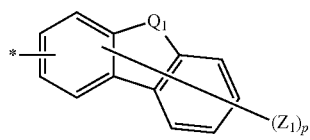

2b

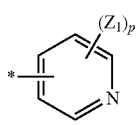

2c

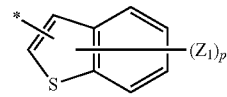

2d wherein, in Formulae 2a to 2d, $Q_1$ is a linker represented by $-C(R_{30})(R_{31})-$, $-O-$, $-S-$, or $-N(R_{32})-$;

$Z_1$, $R_{30}$, $R_{31}$, and $R_{32}$ are each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, an amino group substituted with one or two C6-C20 aryl groups, a substituted or unsubstituted C6-C20 condensed polycyclic group, a halogen group, a cyano group, a nitro group, a hydroxy group, or a carboxy group;

p is an integer from 1 to 7; and

* indicates a binding site of $R_8$ in Formula 3.

7. The heterocyclic compound as claimed in claim 5, wherein X in Formula 3 is a group represented by one of Formulae 3a to 3c:

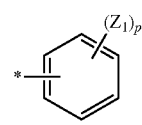

3a

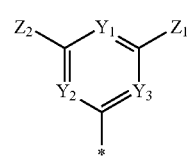

3b

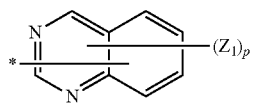

3c wherein, in Formulae 3a to 3c, $Z_1$ and $Z_2$ are each independently a hydrogen atom, a deuterium atom, a substituted or unsubstituted C1-C20 alkyl group, a substituted or unsubstituted C6-C20 aryl group, a substituted or unsubstituted C3-C20 heteroaryl group, a substituted or unsubstituted C6-C20 condensed polycyclic group, a halogen group, a cyano group, a nitro group, a hydroxyl group, or a carboxy group;

$Y_1$ to $Y_3$ are each independently C or N;

p is an integer from 1 to 5; and

* indicates a binding site of X in Formula 3.

8. The heterocyclic compound as claimed in claim 1, wherein the compound of Formula 1 is one of the compounds below:

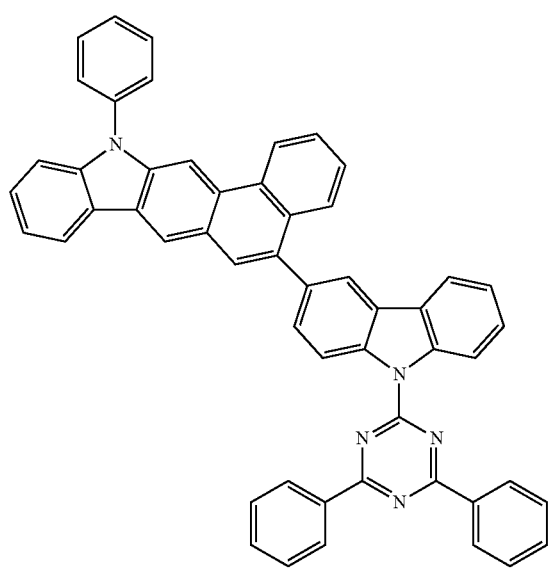

9

-continued

16
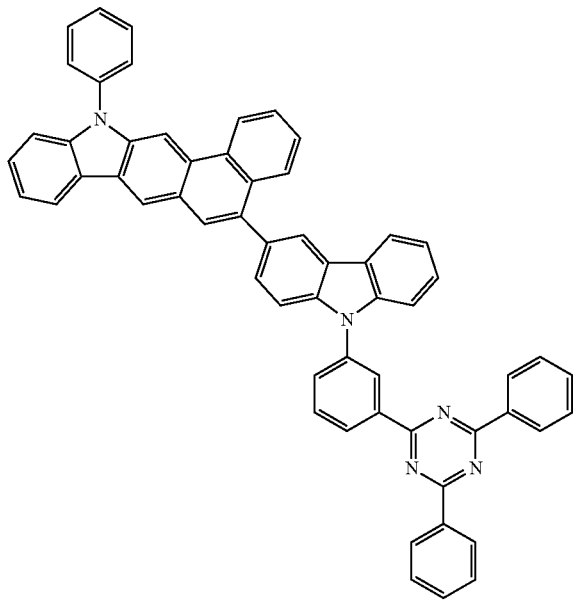

21
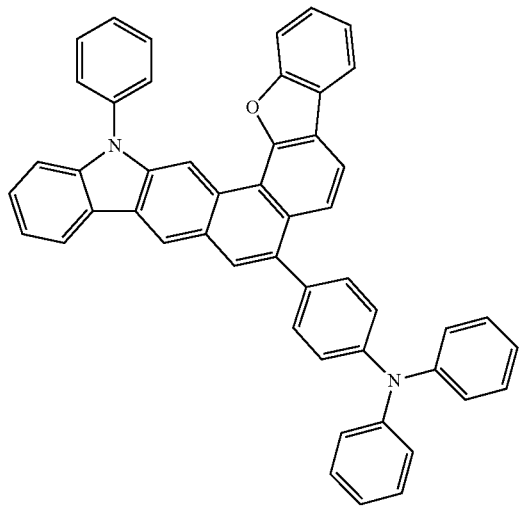

30
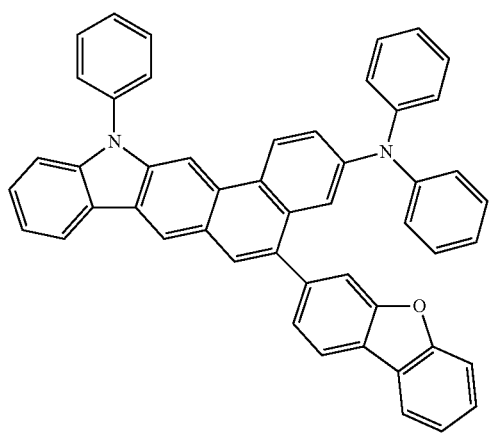

-continued

45
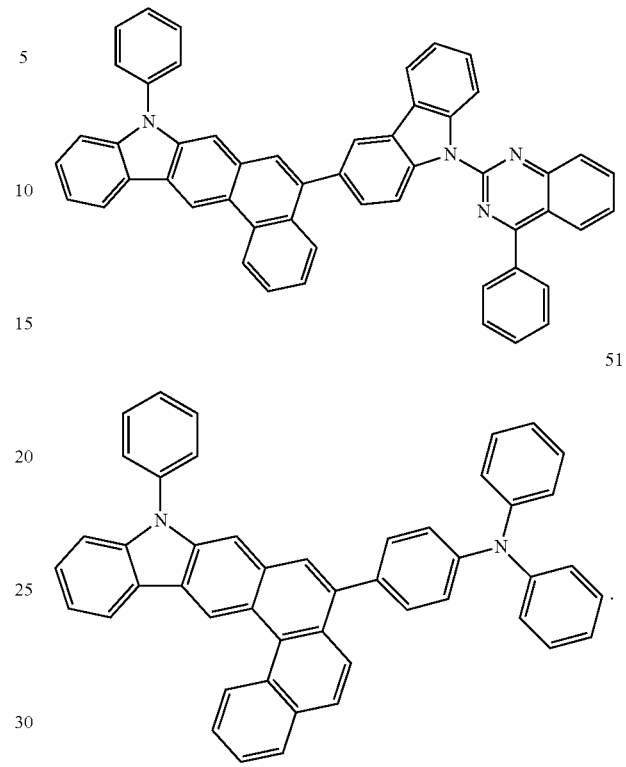

51

9. An organic light-emitting device, comprising:
a first electrode;
a second electrode; and
an organic layer between the first electrode and the second electrode, wherein the organic layer includes the heterocyclic compound as claimed in claim 1.

10. The organic light-emitting device as claimed in claim 9, wherein the organic layer includes an emission layer, and the heterocyclic compound is included as a host or a dopant for a fluorescent or phosphorescent device.

11. The organic light-emitting device as claimed in claim 9, wherein the organic layer is a hole injection layer, a hole transport layer, or a functional layer having both hole injection and hole transport capabilities.

12. The organic light-emitting device as claimed in claim 9, wherein the organic light-emitting device includes:
an emission layer,
an electron injection layer, an electron transport layer, or a functional layer having both electron injection and transport capabilities, and
a hole injection layer, a hole transport layer, or a functional layer having both hole injection and transport capabilities,
wherein the emission layer includes the heterocyclic compound; and
wherein the emission layer further includes an anthracene-based compound, an arylamine-based compound, or a styryl-based compound.

13. The organic light-emitting device as claimed in claim 9, wherein the organic light-emitting device includes:
an emission layer,
an electron injection layer, an electron transport layer, or a functional layer having both electron injection and transport capabilities, and a hole injection layer, a hole transport layer, or a functional layer having both hole injection and transport capabilities;

at least one of the hole injection layer, the hole transport layer, and the functional layer having both hole injection and hole transport capabilities includes the heterocyclic compound; and the emission layer includes at least one of a red, green, blue, or white emission layer, one of which includes a phosphorescent compound.

14. The organic light-emitting device as claimed in claim 13, wherein the at least one of the hole injection layer, the hole transport layer, and the functional layer having both hole injection and hole transport capabilities further includes a charge-generating material.

15. The organic light-emitting device as claimed in claim 14, wherein the charge-generating material is a p-dopant.

16. The organic light-emitting device as claimed in claim 15, wherein the p-dopant is a quinine derivative, a metal oxide, or a cyano group-containing compound.

17. The organic light-emitting device as claimed in claim 9, wherein the organic layer includes an electron transport layer, and the electron transport layer includes a metal complex.

18. The organic light-emitting device as claimed in claim 17, wherein the metal complex is a Li complex.

19. The organic light-emitting device as claimed in claim 9, wherein the organic layer is formed from the heterocyclic compound using a wet process.

20. A flat panel display device comprising the organic light-emitting device as claimed in claim 9, wherein the first electrode of the organic light-emitting device is electrically connected to a source electrode or a drain electrode of a thin-film transistor.

* * * * *